United States Patent
Farchione et al.

(10) Patent No.: US 11,403,756 B2
(45) Date of Patent: *Aug. 2, 2022

(54) FUNDUS IMAGE CAPTURING

(71) Applicant: Welch Allyn, Inc., Skaneateles Falls, NY (US)

(72) Inventors: Richard M. Farchione, Camillus, NY (US); Kristen L. Stebbins, Baldwinsville, NY (US); Corrie A. Baum, Skaneateles, NY (US); Thomas A. Myers, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/906,057

(22) Filed: Jun. 19, 2020

(65) Prior Publication Data

US 2020/0320703 A1 Oct. 8, 2020

Related U.S. Application Data

(63) Continuation of application No. 15/981,129, filed on May 16, 2018, now Pat. No. 10,726,547.

(Continued)

(51) Int. Cl.
*G06K 9/00* (2022.01)
*G06T 7/00* (2017.01)
(Continued)

(52) U.S. Cl.
CPC .......... *G06T 7/0012* (2013.01); *A61B 3/0033* (2013.01); *A61B 3/0041* (2013.01);
(Continued)

(58) Field of Classification Search
CPC ........ G06T 7/0012; G06T 2207/30041; G06T 2210/41; G16H 40/60; G16H 30/20;
(Continued)

(56) References Cited

U.S. PATENT DOCUMENTS

| 4,953,969 A | 9/1990 | Fedorov |
| D396,487 S | 7/1998 | Kunkler |

(Continued)

FOREIGN PATENT DOCUMENTS

| EP | 2 491 854 A2 | 8/2012 |
| JP | 2016-123467 A | 7/2016 |

OTHER PUBLICATIONS

8 Retro Camera Icons, by Creative VIP, creativemarket.com [online], published on Apr. 13, 2015, [retrieved on Mar. 15, 2018], retrieved from the Internet <URL: https://creativemarket.com/creativevip/239422-8-Retro-Camera-Icons>.

(Continued)

*Primary Examiner* — Shervin K Nakhjavan
(74) *Attorney, Agent, or Firm* — Merchant & Gould P.C.

(57) ABSTRACT

An apparatus for producing a fundus image includes: a processor and a memory; an illumination component including a light source and operatively coupled to the processor; a camera including a lens and operatively coupled to the processor, wherein the memory stores instructions that, when executed by the processor, cause the apparatus to capture fundus images and provide controls for re-imaging the fundus.

20 Claims, 38 Drawing Sheets

Related U.S. Application Data

(60) Provisional application No. 62/507,872, filed on May 18, 2017.

(51) Int. Cl.

| | | |
|---|---|---|
| *G06F 3/01* | (2006.01) | |
| *G16H 10/60* | (2018.01) | |
| *G16H 30/20* | (2018.01) | |
| *G16H 40/60* | (2018.01) | |
| *A61B 3/12* | (2006.01) | |
| *A61B 3/00* | (2006.01) | |
| *G16H 30/40* | (2018.01) | |
| *A61B 5/1455* | (2006.01) | |

(52) U.S. Cl.
CPC ........... *A61B 3/1208* (2013.01); *G06F 3/013* (2013.01); *G16H 10/60* (2018.01); *G16H 30/20* (2018.01); *G16H 30/40* (2018.01); *G16H 40/60* (2018.01); *A61B 3/00* (2013.01); *A61B 5/14555* (2013.01); *G06T 2207/30041* (2013.01)

(58) Field of Classification Search
CPC .... G16H 10/60; A61B 3/1208; A61B 3/0041; A61B 3/00; A61B 5/14555; A61B 3/0058; A61B 5/0066; A61B 5/7445; G02B 7/09; G06F 19/321
See application file for complete search history.

(56) References Cited

U.S. PATENT DOCUMENTS

| | | | |
|---|---|---|---|
| D425,934 S | 5/2000 | Kunkler | |
| 6,133,915 A | 10/2000 | Arcuri et al. | |
| D438,874 S | 3/2001 | Flamini | |
| D453,767 S | 2/2002 | Istvan et al. | |
| D456,981 S | 5/2002 | Connell | |
| D463,446 S | 9/2002 | Hoxie et al. | |
| 6,583,799 B1 | 6/2003 | Manolis et al. | |
| D552,623 S | 10/2007 | Vong et al. | |
| 7,386,535 B1 | 6/2008 | Kalucha et al. | |
| D572,726 S | 7/2008 | Guimaraes et al. | |
| D590,415 S | 4/2009 | Ball et al. | |
| 8,095,866 B2 | 1/2012 | Folting et al. | |
| D675,220 S | 1/2013 | McManigal | |
| D675,221 S | 1/2013 | Impas et al. | |
| 8,373,875 B2 | 2/2013 | Ferlitsch et al. | |
| D681,052 S | 4/2013 | Woo | |
| D685,814 S | 7/2013 | Bork et al. | |
| 8,503,609 B2* | 8/2013 | Gertner | A61N 5/1049 378/65 |
| D697,932 S | 1/2014 | Lee et al. | |
| D704,221 S | 5/2014 | Ma et al. | |
| D705,260 S | 5/2014 | Gerssen et al. | |
| D710,884 S | 8/2014 | Winther et al. | |
| 8,879,813 B1* | 11/2014 | Solanki | G06T 5/008 382/128 |
| D719,189 S | 12/2014 | Brinda et al. | |
| 8,915,592 B2 | 12/2014 | Korb et al. | |
| 8,970,847 B2* | 3/2015 | Ono | G01B 9/02063 356/497 |
| D729,275 S | 5/2015 | Kang | |
| D729,836 S | 5/2015 | Lee | |
| D730,405 S | 5/2015 | Yu et al. | |
| D730,937 S | 6/2015 | Kim et al. | |
| D731,540 S | 6/2015 | Kadosh et al. | |
| D731,547 S | 6/2015 | Kim et al. | |
| D739,421 S | 9/2015 | Brinda et al. | |
| D739,430 S | 9/2015 | Gerssen et al. | |
| D741,349 S | 10/2015 | Danielyan et al. | |
| D741,368 S | 10/2015 | Supino et al. | |
| D742,920 S | 11/2015 | Yu et al. | |
| 9,237,847 B2 | 1/2016 | Wang et al. | |
| D751,594 S | 3/2016 | Fedorov | |
| D753,139 S | 4/2016 | Bovet | |
| D754,747 S | 4/2016 | Jou | |
| D755,245 S | 5/2016 | Kim et al. | |
| D757,032 S | 5/2016 | Sabia et al. | |
| D757,070 S | 5/2016 | Dziuba | |
| D761,320 S | 7/2016 | Kim et al. | |
| D762,655 S | 8/2016 | Kai | |
| D762,717 S | 8/2016 | Kim et al. | |
| D768,144 S | 10/2016 | Kim et al. | |
| D771,094 S | 11/2016 | Yin et al. | |
| D772,942 S | 11/2016 | Kim et al. | |
| 9,492,079 B2* | 11/2016 | Walsh | A61B 3/132 |
| D773,528 S | 12/2016 | Kim et al. | |
| D774,543 S | 12/2016 | Yun et al. | |
| D774,573 S | 12/2016 | Sharivker et al. | |
| D775,143 S | 12/2016 | Vazquez et al. | |
| D783,649 S | 4/2017 | Wu et al. | |
| D785,010 S | 4/2017 | Bachman et al. | |
| D785,045 S | 4/2017 | Coffman et al. | |
| D789,383 S | 6/2017 | Bawazeer et al. | |
| D789,953 S | 6/2017 | Thompson et al. | |
| D789,987 S | 6/2017 | Rolfes | |
| D791,173 S | 7/2017 | Hart et al. | |
| 9,704,276 B1 | 7/2017 | Wilson | |
| D796,551 S | 9/2017 | Park et al. | |
| D797,145 S | 9/2017 | Bae et al. | |
| D800,171 S | 10/2017 | Hemsley | |
| D801,385 S | 10/2017 | Bradley et al. | |
| D801,391 S | 10/2017 | Jewitt | |
| D803,881 S | 11/2017 | Hurley et al. | |
| D810,782 S | 2/2018 | Park et al. | |
| D812,071 S | 3/2018 | Riedel | |
| D812,080 S | 3/2018 | Saneii | |
| D822,034 S | 7/2018 | Clymer et al. | |
| D822,050 S | 7/2018 | Gandhi et al. | |
| D831,068 S | 10/2018 | Khandelwal et al. | |
| D835,138 S | 12/2018 | Edgington, Jr. | |
| D852,815 S | 7/2019 | Gavenman et al. | |
| D864,996 S | 10/2019 | Jeon | |
| D866,598 S | 11/2019 | Arora et al. | |
| D870,130 S | 12/2019 | Jang et al. | |
| 2002/0052551 A1* | 5/2002 | Sinclair | A61B 3/0025 600/476 |
| 2003/0007124 A1* | 1/2003 | Levine | A61B 3/103 351/206 |
| 2003/0160825 A1 | 8/2003 | Weber | |
| 2004/0073868 A1 | 4/2004 | Easter et al. | |
| 2004/0254477 A1 | 12/2004 | Sekiguchi | |
| 2005/0071773 A1 | 3/2005 | Ivanovic et al. | |
| 2005/0080770 A1 | 4/2005 | Lueder et al. | |
| 2006/0025658 A1* | 2/2006 | Newman | A61B 3/0091 600/301 |
| 2006/0059437 A1 | 3/2006 | Conklin, III | |
| 2006/0077344 A1* | 4/2006 | Kashiwagi | A61B 3/15 351/206 |
| 2006/0174054 A1 | 8/2006 | Matsuki | |
| 2007/0168425 A1 | 7/2007 | Morotomi | |
| 2008/0100612 A1* | 5/2008 | Dastmalchi | A61B 5/7445 345/418 |
| 2008/0229988 A1 | 9/2008 | Kishi | |
| 2008/0288301 A1 | 11/2008 | Emling et al. | |
| 2008/0294479 A1 | 11/2008 | Emling et al. | |
| 2009/0009479 A1 | 1/2009 | Sawyer | |
| 2011/0246944 A1 | 10/2011 | Byrne et al. | |
| 2011/0271197 A1 | 11/2011 | Jones et al. | |
| 2012/0249956 A1* | 10/2012 | Narasimha-Iyer | A61B 3/113 351/206 |
| 2013/0063698 A1* | 3/2013 | Akiba | G06T 5/004 351/206 |
| 2013/0125057 A1 | 5/2013 | Kashik et al. | |
| 2014/0028976 A1 | 1/2014 | Tanassi et al. | |
| 2014/0063460 A1* | 3/2014 | Borycki | G06T 7/337 351/208 |
| 2014/0223347 A1 | 8/2014 | Seo et al. | |
| 2014/0282016 A1 | 9/2014 | Hosier, Jr. | |
| 2014/0282077 A1 | 9/2014 | Wilson et al. | |

(56) References Cited

U.S. PATENT DOCUMENTS

| | | | |
|---|---|---|---|
| 2014/0320810 A1* | 10/2014 | Fukuma | A61B 3/102 351/206 |
| 2015/0279238 A1* | 10/2015 | Forte | G09B 7/02 434/271 |
| 2015/0342452 A1* | 12/2015 | Hara | A61B 3/024 351/224 |
| 2016/0120405 A1 | 5/2016 | Tokuda et al. | |
| 2016/0166142 A1* | 6/2016 | Kobayashi | G06T 3/0018 351/206 |
| 2016/0247542 A1 | 8/2016 | Tanaka | |
| 2016/0249804 A1* | 9/2016 | Wang | A61B 3/152 351/208 |
| 2016/0270656 A1* | 9/2016 | Samec | G02B 21/0032 |
| 2017/0075528 A1 | 3/2017 | Kothari et al. | |
| 2017/0116373 A1 | 4/2017 | Ginsburg et al. | |
| 2017/0119241 A1 | 5/2017 | Farchione et al. | |
| 2017/0164830 A1* | 6/2017 | Huang | G06T 7/0014 |
| 2017/0273557 A1* | 9/2017 | Nakazawa | G06T 7/62 |
| 2017/0286419 A1 | 10/2017 | Tang et al. | |
| 2018/0263486 A1 | 9/2018 | Farchione et al. | |
| 2018/0336355 A1 | 11/2018 | Agarwal | |
| 2019/0117064 A1* | 4/2019 | Fletcher | A61B 3/0025 |
| 2019/0343381 A1* | 11/2019 | Dastmalchi | G06T 15/08 |

OTHER PUBLICATIONS

Collection of Simple Eye Icon or Logo Isolated, iconswebsite.com [online], published on Feb. 19, 2017, [retrieved on Mar. 15, 2018], retrieved from the Internet <URL: http://iconswebsite.com/shutterstock-image/collection-of-simple-eye-icon-or-logo-isolated-582438643.html>.
International Search Report and Written Opinion for Application No. PCT/US2018/033004 dated Sep. 5, 2018.
Install and Run IIS Web Server in Windows, by LK, techjourney.net [online], published on Dec. 9, 2016, [retrieved on Mar. 9, 2018], retrieved from the Internet <URL: https ://techjourney.net/install-run-iis-internet-information-services-web-server-in-windows-10-8-1-8 -7-vista/>.
Miscellaneous I—Outline Style, by Ruiz, iconfinder.com [online], published on Jan. 19, 2017, [retrieved on Mar. 13, 2018], retrieved from the Internet <URL: https://www.iconfinder.com/iconsets/miscellaneous-i-line-style> (Year: 2017).
Photo Site Icons, iconswebsite.com [online], published on Dec. 2, 2016, [retrieved on Mar. 13, 2018], retrieved from the Internet <URL: http://iconswebsite.com/shutterstock-image/photo-site-icons-527985820.html> (Year: 2016).
Photography, Video , Music Set1, by HowColour, iconfinder.com [online], published on Sep. 19, 2016, [retrieved on Mar. 13, 2018], retrieved from the Internet <URL: https://www.iconfinder.com/iconsets/photography-video-music-set1 > (Year: 2016).
Trademark Registration Serial No. 85858513, Feb. 24, 2013 (first use date), (REGISTRANT) Rankins, Kenneth V. Individual, California, Trademark Electronic Service System (TESS).
Trademark Registration Serial No. 86310940, Jan. 1, 2013 (first use date), (REGISTRANT) VisionsOutdoor LLC., Limited Liability Company, New Jersey, Trademark Electronic Service System (TESS).
Typicons, iconfinder.com [online], published on Nov. 12, 2013, [retrieved on Mar. 15, 2018], retrieved from the Internet <URL: https:// www. iconfinder.com/iconsets/typicons-2 >.
Ui Kit, by Sargin, iconfinder.com [online], published on Sep. 12, 2014, [retrieved on Mar. 13, 2018], retrieved from the internet <URL: https://www.iconfinder.com/iconsets/ui-kit> (Year: 2014).
Vector Black Confirm Icons Set, iconswebsite.com [online], published on Oct. 27, 2017, [retrieved on Mar. 9, 2018], retrieved from the Internet <URL: http://iconswebsite.com/shutterstock-image/vector-black-confirm-icons-set-226227700.html>.
Vectory Bonus 1, by Icojam, iconfinder.com [online], published on May 10, 2013, [retrieved on Mar. 13, 2018], retrieved from the Internet <URL: https://www.iconfinder.com/iconsets/vectory-bonus-1 > (Year: 2013).
Welch Allyn RetinaVue 100 Guide, by Total Advertising Video Samples, YouTube [online], published on Dec. 12, 2016, [retrieved on Mar. 9, 2018], retrieved from the Internet <URL: https://www.youtube.com/watch?v=gPvZtpdgUzE (Year: 2016).
U.S. Appl. No. 29/604,517, filed May 18, 2017 entitled "Electronic Display Screen of a Medical Device With an Icon".
U.S. Appl. No. 29/604,521, filed May 18, 2017 entitled "Electronic Display Screen of a Medical Device With an Icon".
U.S. Appl. No. 29/604,529, filed May 18, 2017 entitled "Electronic Display Screen of a Medical Device With an Icon".
Material Multimedia vol. 1, by IcoJam, iconfinder.com [online], published on Jun. 26, 2016, [retrieved on Nov. 20, 2018], retrieved from the Internet <URL: https://www.iconfinder.com/iconsets/materia-multimedia> (Year: 2016).
Trademark Registration U.S. Appl. No. 75/214,977, filed Sep. 16, 1997 (publication date), (Applicant) Molecules to Market Limited, Company, Ireland, Trademark Electronic Service System (TESS), (Year: 1997).
Welch Allyn RetinaVue 100 Imager, fccid.io [online], published on Dec. 31, 2015, [retrieved on Nov. 20, 2018], retrieved from the Internet <URL: https://fccid.io/pdf.php?id=2860975> (Year: 2015).
Excel 2013: Filtering Data, by GFCLearnFree.org, YouTube [online], published on Nov. 26, 2013, [retrieved from the Internet <URL:https:// www. you tube .com/watch?ti me_conti nue=228&v=9JxcQbSci_ c> (Year: 2013).
Tri-State Tree View, by Lockwood, codeproject.com [online], published on May 30, 2011, [retrieved on Mar. 28, 2019], retrieved from the Internet <URL: https ://www .codeproject.com/ Articles/202435/ Tri-State-Tree-View> (Year: 2011).
Tree View, docs.oracle.com [online], published on or before Mar. 28, 2014, [retrieved on Mar. 28, 2019], retrieved from the Internet<URL: https ://docs.oracle .com/javase/8/javafx/user-interface-tutorial/tree-view. htm> (Year: 2014).
Treeview Checkbox, by Wolf, planet-source-code.com [online], published on Jan. 26, 2015, [retrieved on Mar. 28, 2019], retrieved from the Internet <URL: https://www.planet-source-code.com/vb/scripts/ShowCode.asp?txtCodeId=37037&IngWld=1 > (Year: 2015).
Extended European Search Report for Application No. 18801356.9 dated Feb. 1, 2021.

* cited by examiner

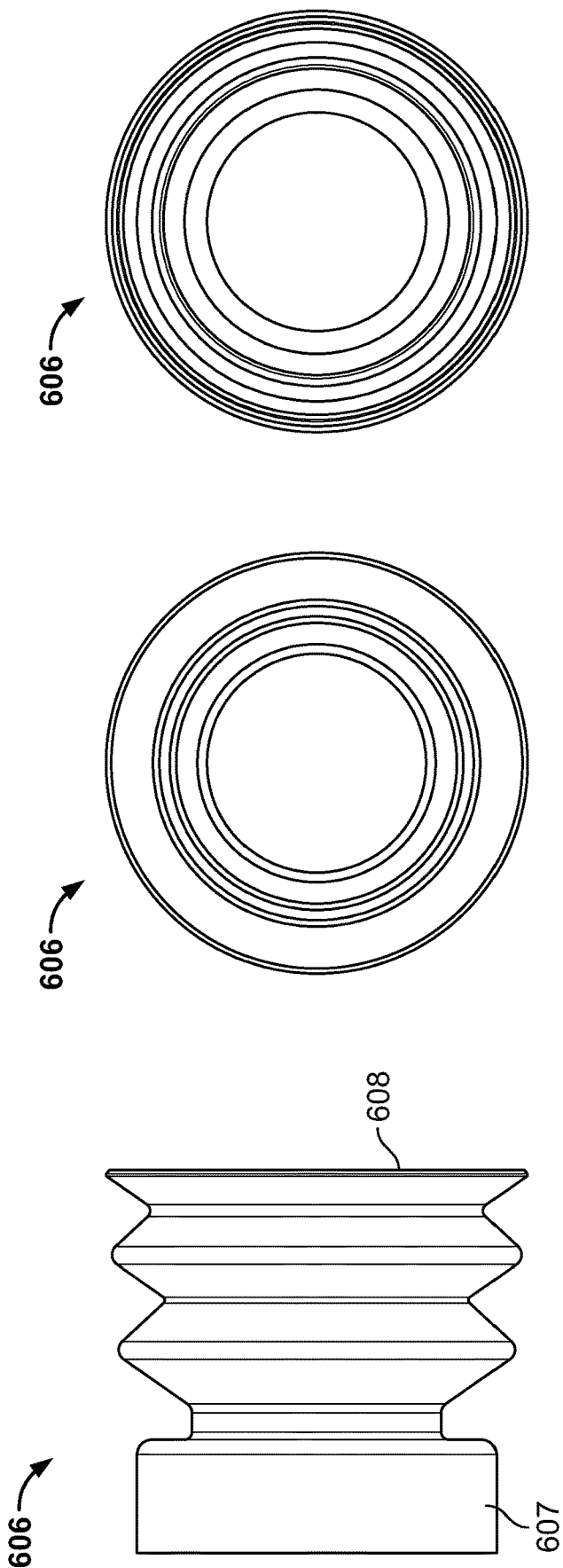

FUNDUS IMAGE CAPTURING

CROSS REFERENCE TO RELATED APPLICATIONS

This patent application is related to U.S. patent application Ser. No. 14/633,601, filed on Feb. 27, 2015, U.S. patent application Ser. No. 15/009,988, filed on Jan. 29, 2016, U.S. patent application Ser. No. 14/177,594 filed on Feb. 11, 2014, and U.S. patent application Ser. No. 15/054,558 filed on Feb. 26, 2016, the entireties of which are hereby incorporated by reference.

INTRODUCTION

People with type 1 or type 2 diabetes can develop eye disease as a result of having diabetes. One of the most common diabetic eye diseases is diabetic retinopathy, which is damage to the blood vessels of the light-sensitive tissue at the back of the eye, known as the retina. Trained medical professionals use cameras during eye examinations for diabetic retinopathy screening. The cameras can produce images of the back of the eye and trained medical professionals use those images to diagnose and treat diabetic retinopathy.

These images are produced either with pharmacological pupil dilation, known as mydriatic fundus imaging, or without pharmacological pupil dilation, known as non-mydriatic fundus imaging. Because pupil dilation is inversely related, in part, to the amount of ambient light, non-mydriatic fundus imaging usually occurs in low lighting environments. Medical professionals can also use fundus imaging apparatus to detect or monitor other diseases, such as hypertension, glaucoma, and papilledema.

SUMMARY

In one aspect, a method for imaging a fundus of a patient includes: receiving an eye input, the eye input including an indication of a given eye of the patient to image; receiving a focus input, the focus input indicating an image point focus of a portion of the given eye; capturing a first image of the given eye at the image point focus; presenting a control on a graphical user interface, the control configured to initiate an image acquisition sequence of the given eye; after receiving selection of the control, capturing a second image of the given eye at the image point focus; and storing both the first image and the second image.

In another aspect, a method for capturing one or more images of a fundus of a patient includes: providing a summary interface on a display, where the summary interface includes: an indication of the number of images captured for each eye, an indication of a focus type for each eye; and for each captured image, an indication of the quality of the image. The method also includes: if only one image has been captured for a given eye at an image point focus, provide a control to initiate an additional image capture; initiating a retinal image capture workflow, the retinal image capture workflow resulting in image capture of the selected eye with the selected focus type; and displaying to the summary interface after capturing the second image.

In another aspect, a method for imaging a fundus of a patient includes: selecting a first prescriptive workflow for capturing a first image of an eye, including: receiving a first eye input, the first eye input indicating a given eye of the patient to image; receiving a first focus input, the first focus input indicating a first image point focus of a first portion of the given eye; and capturing a first image of the given eye at the first image point focus. The method additionally includes: selecting a second prescriptive workflow for capturing a second image of the eye, including: receiving a second eye input, the second eye input indicating the given eye of the patient to image; receiving a second focus input, the second focus input indicating a second image point focus of a second portion of the given eye; and capturing a second image of the given eye at the second image point focus, and storing both the first image and the second image.

DESCRIPTION OF THE FIGURES

The following figures, which form a part of this application, are illustrative of described technology and are not meant to limit the scope of the claims in any manner, which scope shall be based on the claims appended hereto.

FIG. 30 is another view of the eye cup of FIG. 28;

FIG. 31 is another view of the eye cup of FIG. 28;

FIG. 32 is another view of the eye cup of FIG. 28;

DETAILED DESCRIPTION

Figure 1:
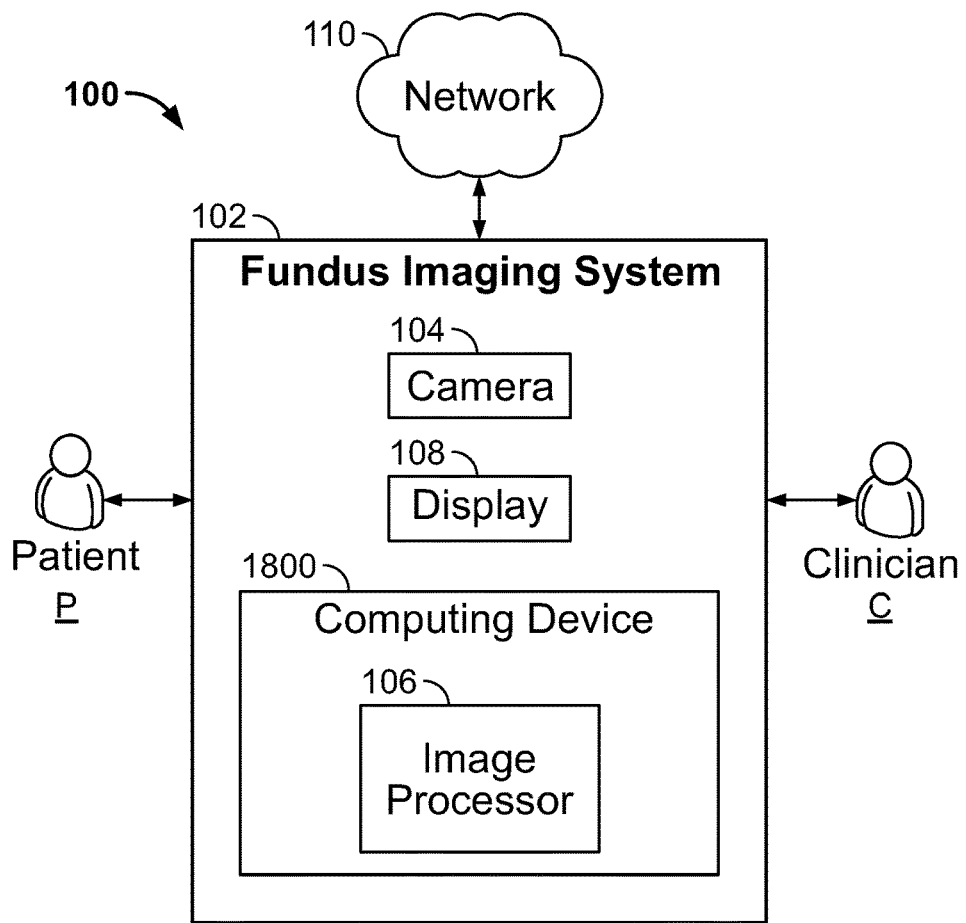
FIG. 1 is an embodiment of an example system for recording and viewing an image of a patient's fundus.

FIG. 1 is a schematic block diagram illustrating an example system 100 for recording and viewing an image of a patient's fundus. In this example, the system 100 includes a patient P, a fundus imaging system 102, a computing device 1800 including an image processor 106, a camera 104 in communication with the computing device 1800, a display 108 in communication with the computing device 1800 and used by clinician C, and a network 110. An embodiment of the example fundus imaging system 102 is shown and described in more detail below with reference to FIG. 4.

The fundus imaging system 102 functions to create a set of digital images of a patient's P eye fundus. As used herein, "fundus" refers to the eye fundus and includes the retina, optic nerve, macula, vitreous, choroid and posterior pole.

In this example, one or more images of the eye are desired. For instance, the patient P is being screened for an eye disease, such as diabetic retinopathy. The fundus imaging system 102 can also be used to provide images of the eye for other purposes, such as to diagnose or monitor the progression of a disease such as diabetic retinopathy.

The fundus imaging system 102 includes a handheld housing that supports the system's components. The housing supports one or two apertures for imaging one or two eyes at a time. In embodiments, the housing supports positional guides for the patient P, such as an optional adjustable chin rest. The positional guide or guides help to align the patient's P eye or eyes with the one or two apertures. In embodiments, the housing supports means for raising and lowering the one or more apertures to align them with the patient's P eye or eyes. Once the patient's P eyes are aligned, the clinician C then initiates the image captures by the fundus imaging system 102.

One technique for fundus imaging requires mydriasis, or the dilation of the patient's pupil, which can be painful and/or inconvenient to the patient P. Example system 100 does not require a mydriatic drug to be administered to the patient P before imaging, although the system 100 can image the fundus if a mydriatic drug has been administered.

The system 100 can be used to assist the clinician C in screening for, monitoring, or diagnosing various eye diseases, such as hypertension, diabetic retinopathy, glaucoma and papilledema. It will be appreciated that the clinician C that operates the fundus imaging system 102 can be different from the clinician C evaluating the resulting image.

In the example embodiment 100, the fundus imaging system 102 includes a camera 104 in communication with an image processor 106. In this embodiment, the camera 104 is a digital camera including a lens, an aperture, and a sensor array. The camera 104 lens is a variable focus lens, such as a lens moved by a step motor, or a fluid lens, also known as a liquid lens in the art. The camera 104 is configured to record images of the fundus one eye at a time. In other embodiments, the camera 104 is configured to record an image of both eyes substantially simultaneously. In those embodiments, the fundus imaging system 102 can include two separate cameras, one for each eye.

In example system 100, the image processor 106 is operatively coupled to the camera 104 and configured to communicate with the network 110 and display 108.

The image processor 106 regulates the operation of the camera 104. Components of an example computing device, including an image processor, are shown in more detail in FIG. 7, which is described further below.

The display 108 is in communication with the image processor 106. In the example embodiment, the housing supports the display 108. In other embodiments, the display connects to the image processor, such as a smart phone, tablet computer, or external monitor. The display 108 functions to reproduce the images produced by the fundus imaging system 102 in a size and format readable by the clinician C. For example, the display 108 can be a liquid crystal display (LCD) and active matrix organic light emitting diode (AMOLED) display. The display can be touch sensitive.

The example fundus imaging system 102 is connected to a network 110. The network 110 may include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging system 102 and an external display using one or more wired or wireless protocols, such as Bluetooth, Wi-Fi Direct, radio-frequency identification (RFID), or Zigbee. Other configurations are possible.

Figure 2:
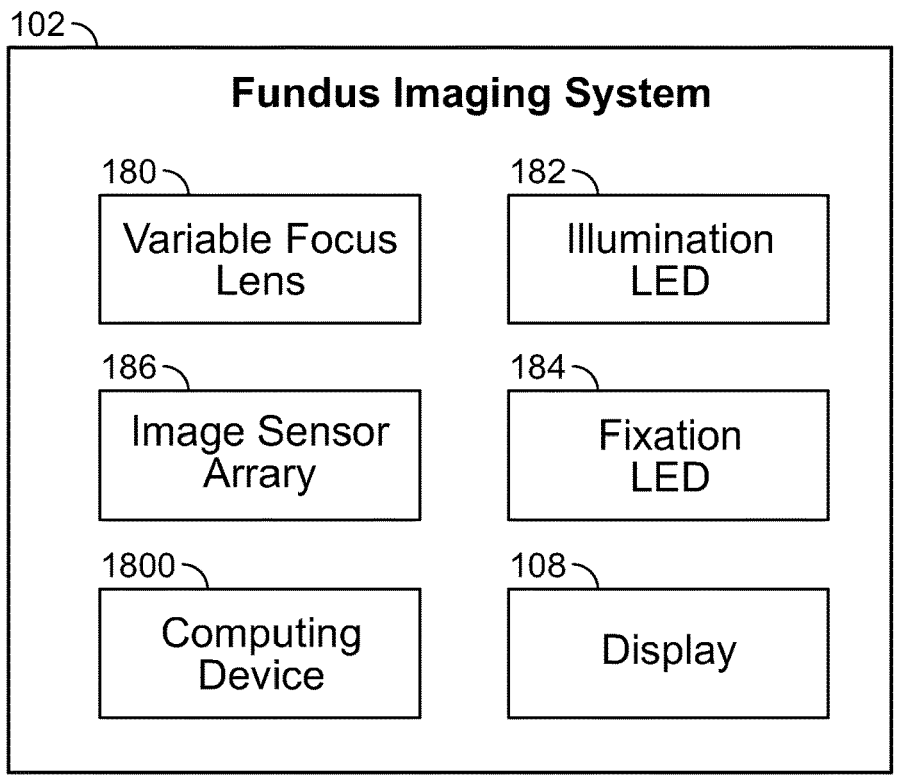
FIG. 2 is an embodiment of an example fundus imaging system.

FIG. 2 illustrates components of an example fundus imaging system 102. The example fundus imaging system 102 includes a variable focus lens 180, an illumination LED 182, an image sensor array 186, a fixation LED 184, a computing device 1800, and a display 108. Each component is in electrical communication with, at least, the computing device 1800. Other embodiments can include more or fewer components.

In one of the embodiments, the variable focus lens 180 is a liquid lens. A liquid lens is an optical lens whose focal length can be controlled by the application of an external force, such as a voltage. The lens includes a transparent fluid, such as water or water and oil, sealed within a cell and a transparent membrane. By applying a force to the fluid, the curvature of the fluid changes, thereby changing the focal length. This effect is known as electrowetting.

Generally, a liquid lens can focus between about −10 diopters to about +30 diopters. The focus of a liquid lens can be made quickly, even with large changes in focus. For instance, some liquid lenses can autofocus in tens of milliseconds or faster. Liquid lenses can focus from about 10 cm to infinity and can have an effective focal length of about 16 mm or shorter.

In another embodiment of example fundus imaging system 102, the variable focus lens 180 is one or more movable lenses that are controlled by a stepping motor, a voice coil, an ultrasonic motor, or a piezoelectric actuator. Additionally, a stepping motor can also move the image sensor array 186. In those embodiments, the variable focus lens 180 and/or the image sensor array 186 are oriented normal to an optical axis of the fundus imaging system 102 and move along the optical axis. An example stepping motor is shown and described below with reference to FIG. 4.

The example fundus imaging system 102 also includes an illumination light-emitting diode (LED) 182. The illumination LED 182 can be single color or multi-color. For example, the illumination LED 182 can be a three-channel RGB LED, where each die is capable of independent and tandem operation.

Optionally, the illumination LED 182 is an assembly including one or more visible light LEDs and a near-infrared LED. The optional near-infrared LED can be used in a preview mode, for example, for the clinician C to determine or estimate the patient's P eye focus without illuminating visible light that could cause the pupil to contract or irritate the patient P.

The illumination LED 182 is in electrical communication with the computing device 1800. Thus, the illumination of illumination LED 182 is coordinated with the adjustment of the variable focus lens 180 and image capture. The illumination LED 182 can be overdriven to draw more than the maximum standard current draw rating. In other embodiments, the illumination LED 182 can also include a near-infrared LED. The near-infrared LED is illuminated during a preview mode.

The example fundus imaging system 102 also optionally includes a fixation LED 184. The fixation LED 184 is in communication with the computing device 1800 and produces a light to guide the patient's P eye for alignment. The fixation LED 184 can be a single color or multicolor LED. For example, the fixation LED 184 can produce a beam of green light that appears as a green dot when the patient P looks into the fundus imaging system 102. Other colors and designs, such as a cross, "x" and circle are possible.

The example fundus imaging system 102 also includes an image sensor array 186 that receives and processes light reflected by the patient's fundus. The image sensor array 186 is, for example, a complementary metal-oxide semiconductor (CMOS) sensor array, also known as an active pixel sensor (APS), or a charge coupled device (CCD) sensor.

The image sensor array 186 has a plurality of rows of pixels and a plurality of columns of pixels. In some embodiments, the image sensor array has about 1280 by 1024 pixels, about 640 by 480 pixels, about 1500 by 1152 pixels, about 2048 by 1536 pixels, or about 2560 by 1920 pixels.

In some embodiments, the pixel size in the image sensor array 186 is from about four micrometers by about four micrometers; from about two micrometers by about two micrometers; from about six micrometers by about six micrometers; or from about one micrometer by about one micrometer.

The example image sensor array 186 includes photodiodes that have a light-receiving surface and have substantially uniform length and width. During exposure, the photodiodes convert the incident light to a charge. The image sensor array 186 can be operated as a global reset, that is, substantially all of the photodiodes are exposed simultaneously and for substantially identical lengths of time.

The example fundus imaging system 102 also includes a display 108, discussed in more detail above with reference to FIG. 1. Additionally, the example fundus imaging system 102 includes a computing device 1800, discussed in more detail below with reference to FIG. 7.

Figure 3:
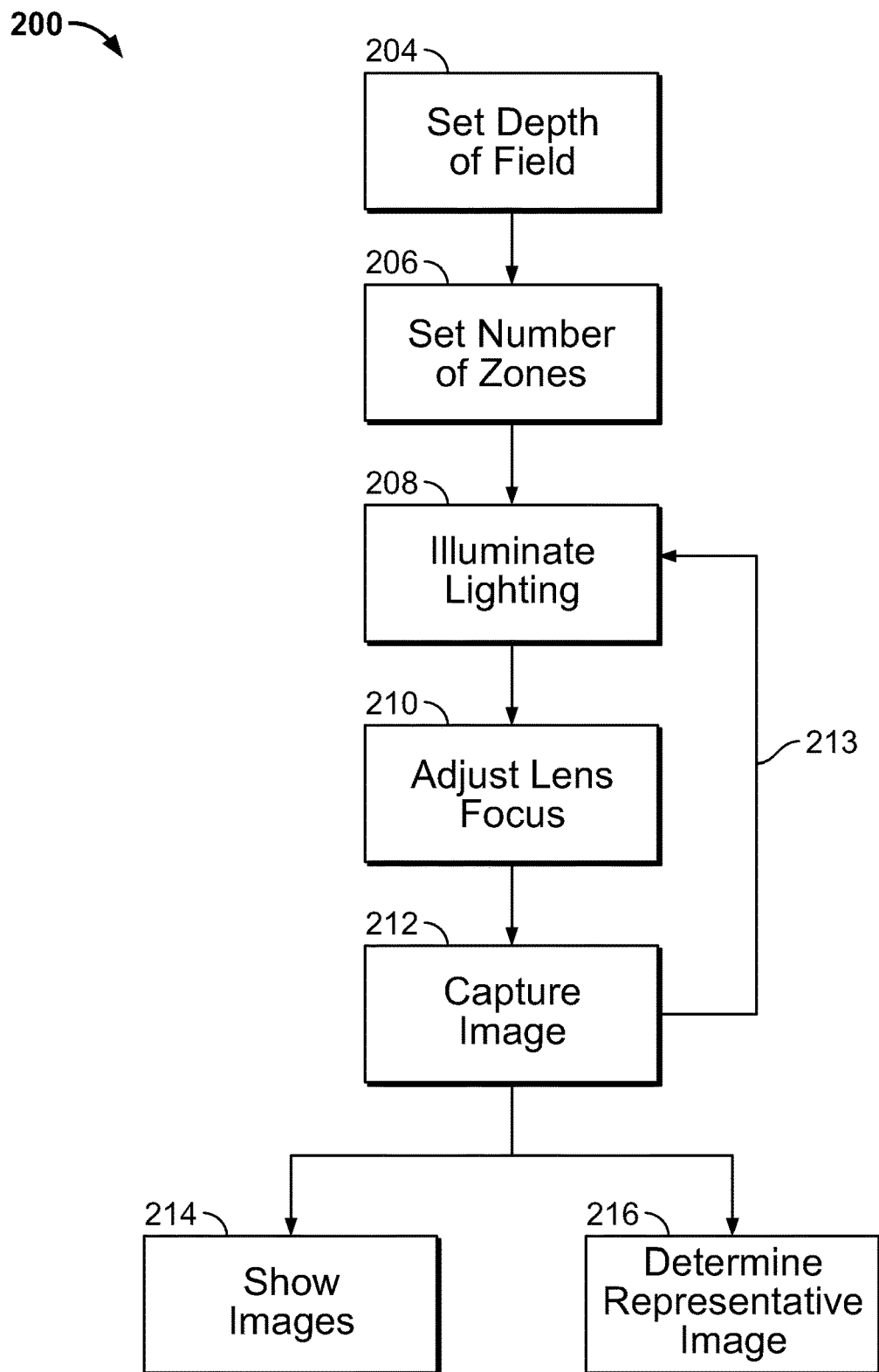
FIG. 3 is an embodiment of an example method for imaging a patient's fundus using a fundus imaging system.

FIG. 3 is an embodiment of a method 200 for imaging a patient's fundus using a fundus imaging system. In the embodiment shown, the lighting is optimally dimmed prior to execution, although lowering the lighting is optional. The embodiment shown includes a set depth of field operation 204, a set number of zones operation 206, an illuminate lighting operation 208, an adjust lens focus operation 210, a capture image operation 212, repeat operation(s) 213, a show images operation 214 and a determine representative image operation 216. Other embodiments can include more or fewer steps.

The embodiment of method 200 begins with setting a depth of field operation 204. In embodiments, the variable focus lens 180 is capable of focusing from about −20 diopters to about +20 diopters. Set depth of field operation 204 defines the lower and upper bounds in terms of diopters. For example, the depth of field range could be set to about −10 to +10 diopters; about −5 to about +5 diopters; about −10 to about +20 diopters; about −5 to about +20 diopters; about −20 to about +0 diopters; or about −5 to about +5 diopters. Other settings are possible. The depth of field can be preprogrammed by the manufacturer. Alternatively, the end user, such as the clinician C, can set the depth of field.

As shown in FIG. 3, the next operation in embodiment of method 200 is setting the number of zones operation 206. However, zones operation 206 can occur before or concurrent with field operation 204. In zones operation 206, the depth of field is divided into equal parts, where each part is called a zone. In other embodiments, the zones are not all equal. The number of zones is equal to the number of images captured in capture image operation 212.

For example, when the depth of field is from −10 to +10 diopters, the focus of the variable focus lens can be changed by 4 diopters before each image capture. Thus, in this example, images would be captured at −10, −6, −2, +2, +6 and +10 diopters. Or, images could be captured at −8, −4, 0, +4 and +8 diopters, thereby capturing an image in zones −10 to −6 diopters, −6 to −2 diopters, −2 to +2 diopters, +2 to +6 diopters and +6 to +10 diopters, respectively. In that instance, the depth of focus is about +/−2 diopters. Of course, the number of zones and the depth of field can vary, resulting in different ranges of depth of field image capture.

In embodiments, both depth of field and number of zones are predetermined. For example, −10D to +10D and 5 zones. Both can be changed by a user.

After the depth of field and number of zones are set, the next operation in embodiment of method 200 is the image capture process, which includes illuminate lighting operation 208, adjust lens focus operation 210 and capture image operation 212. As shown in FIG. 3, the lighting component is illuminated (lighting operation 208) before the lens focus is adjusted (lens focus operation 210). However, lens focus operation 210 can occur before or concurrent with lighting operation 208.

The illumination LED 182 is illuminated in lighting operation 208. The illumination LED 182 can remain illuminated throughout the duration of each image capture. Alternatively, the illumination LED 182 can be turned on and off for each image capture. In embodiments, the illumination LED 182 only turns on for the same period of time as the image sensor array 186 exposure time period.

Optionally, lighting operation 208 can additionally include illuminating a near-infrared LED. The clinician C can use the illumination of the near-infrared LED as a way to preview the position of the patient's P pupil.

The focus of variable focus lens 180 is adjusted in lens focus operation 210. Autofocusing is not used in embodiment of method 200. That is, the diopter setting is provided to the lens without regard to the quality of the focus of the image. Indeed, traditional autofocusing fails in the low-lighting non-mydriatic image capturing environment. The embodiment of method 200 results in a plurality of images at least one of which, or a combination of which, yields an in-focus view of the patient's P fundus.

Additionally, the lack of autofocusing enables the fundus imaging system 102 to rapidly capture multiple images in capture image operation 212 at different diopter ranges. That is, variable focus lens 180 can be set to a particular diopter range and an image captured without the system verifying that the particular focus level will produce an in-focus image, as is found in autofocusing systems. Because the system does not attempt to autofocus, and the focus of the variable focus lens 180 can be altered in roughly tens of milliseconds, images can be captured throughout the depth of field in well under a second, in embodiments. Thus, in the embodiment of method 200, the fundus imaging system 102 can capture images of the entire depth of field before the patient's P eye can react to the illuminated light. Without being bound to a particular theory, depending on the patient P, the eye might react to the light from illumination LED 182 in about 150 milliseconds.

The image sensor array 186 captures an image of the fundus in capture image operation 212. As discussed above, the embodiment of method 200 includes multiple image captures of the same fundus at different diopter foci. The example fundus imaging system 102 uses a global reset or global shutter array, although other types of shutter arrays, such as a rolling shutter, can be used. The entire image capture method 200 can also be triggered by passive eye tracking and automatically capture, for example, 5 frames of images. An embodiment of example method for passive eye tracking is shown and described in more detail with reference to FIG. 5, below.

After the fundus imaging system 102 captures an image of the fundus, the embodiment of method 200 returns in loop 213 to either the illuminate lighting operation 208 or the adjust lens focus operation 210. That is, operations 208, 210 and 212 are repeated until an image is captured in each of the preset zones from zones operation 206. It is noted that the image capture does not need to be sequential through the depth of field. Additionally, each of the images does not need to be captured in a single loop; a patient could have one or more fundus images captured and then one or more after a pause or break.

After an image is captured in each of the zones (capture image operation 212) in embodiment of method 200, either the images are displayed in show images operation 214 or a representative image is determined in operation 216 and then the image is displayed. Show images operation 214 can include showing all images simultaneously or sequentially on display 108. A user interface shown on display 108 can then enable the clinician C or other reviewing medical professional to select or identify the best or a representative image of the patient's P fundus.

In addition to, or in place of, show images operation 214, the computing device can determine a representative fundus image in operation 216. Operation 216 can also produce a single image by compiling aspects of one or more of the images captured. This can be accomplished by, for example, using a wavelet feature reconstruction method to select, interpolate, and/or synthesize the most representative frequency or location components.

The fundus imaging system 102 can also produce a three-dimensional image of the fundus by compiling the multiple captured images. Because the images are taken at different focus ranges of the fundus, the compilation of the pictures can contain three-dimensional information about the fundus.

In turn, the image or images from operation 214 or 216 can be sent to a patient's electronic medical record or to a different medical professional via network 110.

Figure 4:
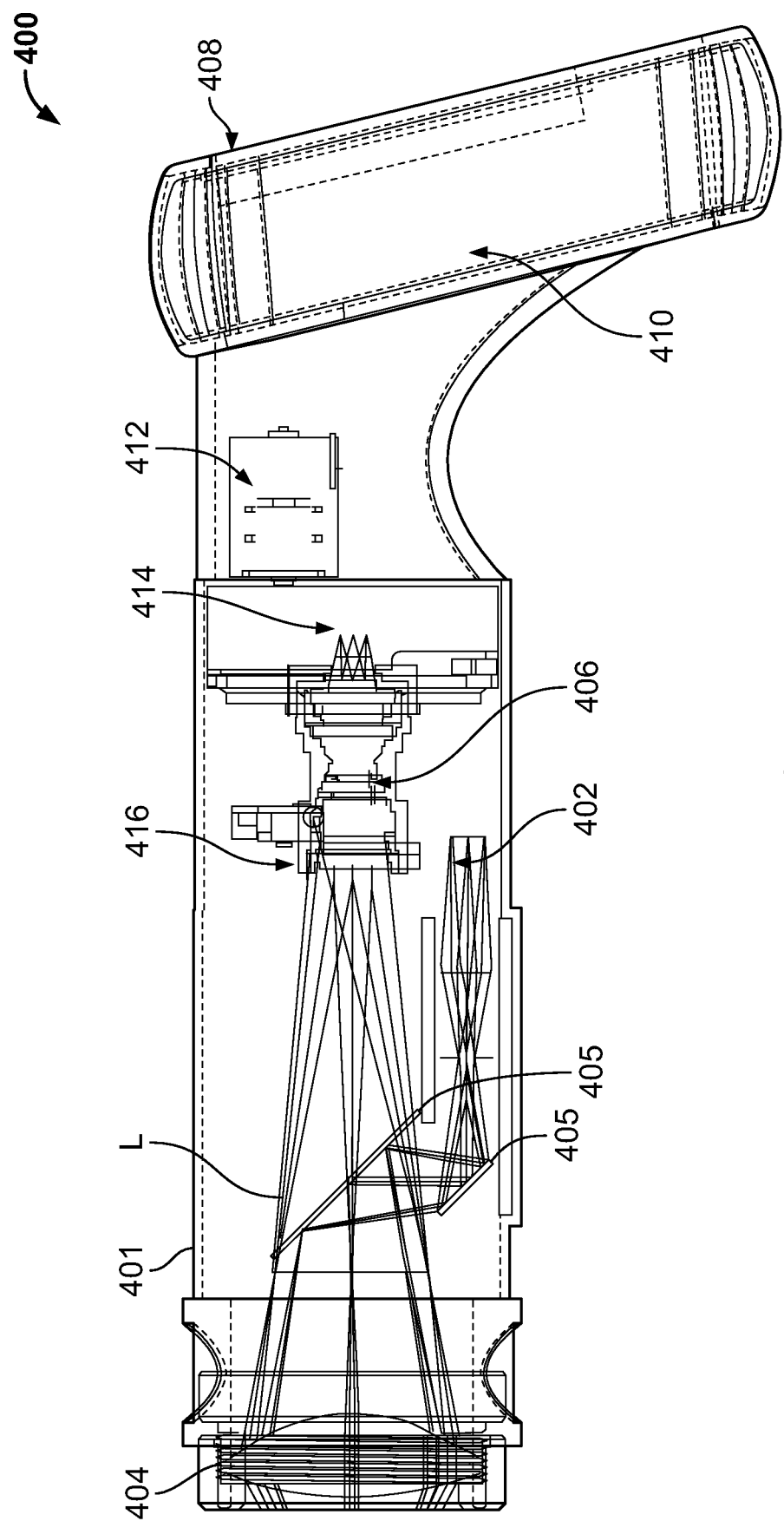
FIG. 4 is an embodiment of an example fundus imaging system.

FIG. 4 illustrates an embodiment of example fundus imaging system 400. The embodiment 400 includes a housing 401 that supports an optional fixation LED 402, an objective lens 404, fixation LED mirrors 405, variable focus lens assembly 406, display 408, printed circuit board 410, step motor 412, image sensor array 414, and illumination LED 416. Also shown in FIG. 4 are light paths L that include potential light paths from optional fixation LED 402 and incoming light paths from outside the fundus imaging system 400. The illustrated components have the same or similar functionality to the corresponding components discussed above with reference to FIGS. 1-3 above. Other embodiments can include more or fewer components.

The housing 401 of example fundus imaging system 400 is sized to be hand held. In embodiments, the housing 401 additionally supports one or more user input buttons near display 408, not shown in FIG. 4. The user input button can initiate the image capture sequence, at least a portion of which is shown and discussed with reference to FIG. 3, above. Thus, the fundus imaging system 400 is capable of being configured such that the clinician C does not need to adjust the lens focus.

Fixation LED 402 is an optional component of the fundus imaging system 400. The fixation LED 402 is a single or multi-colored LED. Fixation LED 402 can be more than one LED.

As shown in FIG. 4, pivoting mirrors 405 can be used to direct light from the fixation LED 402 towards the patient's pupil. Additionally, an overlay or filter can be used to project a particular shape or image, such as an "X", to direct the patient's focus. The pivoting mirrors 405 can control where the fixation image appears in the patient's view. The pivoting mirrors 405 do not affect the light reflected from the patient's fundus.

The embodiment of example fundus imaging system 400 also includes a variable focus lens assembly 406. As shown in FIG. 4, the variable focus lens assembly 406 is substantially aligned with the longitudinal axis of the housing 401. Additionally, the variable focus lens assembly 406 is positioned between the objective lens 404 and the image sensor array 414 such that it can control the focus of the incident light L onto the image sensor array.

The example printed circuit board 410 is shown positioned within one distal end of the housing 401 near the display 408. However, the printed circuit board 410 can be positioned in a different location. The printed circuit board 410 supports the components of the example computing device 1800. A power supply can also be positioned near printed circuit board 410 and configured to power the components of the embodiment of example fundus imaging system 400.

Step motor 412 is an optional component in the example embodiment 400. Step motor 412 can also be, for example, a voice coil, an ultrasonic motor, or a piezoelectric actuator. In the example embodiment 400, step motor 412 moves the variable focus lens assembly 406 and/or the sensor array 414 to achieve variable focus. The step motor 412 moves the variable focus lens assembly 406 or the sensor array 414 in a direction parallel to a longitudinal axis of the housing 401 (the optical axis). The movement of step motor 412 is actuated by computing device 1800.

The example image sensor array 414 is positioned normal to the longitudinal axis of the housing 401. As discussed above, the image sensor array 414 is in electrical communication with the computing device. Also, as discussed above, the image sensor array can be a CMOS (APS) or CCD sensor.

An illumination LED 416 is positioned near the variable focus lens assembly 406. However, the illumination LED 416 can be positioned in other locations, such as near or with the fixation LED 402.

Figure 5:
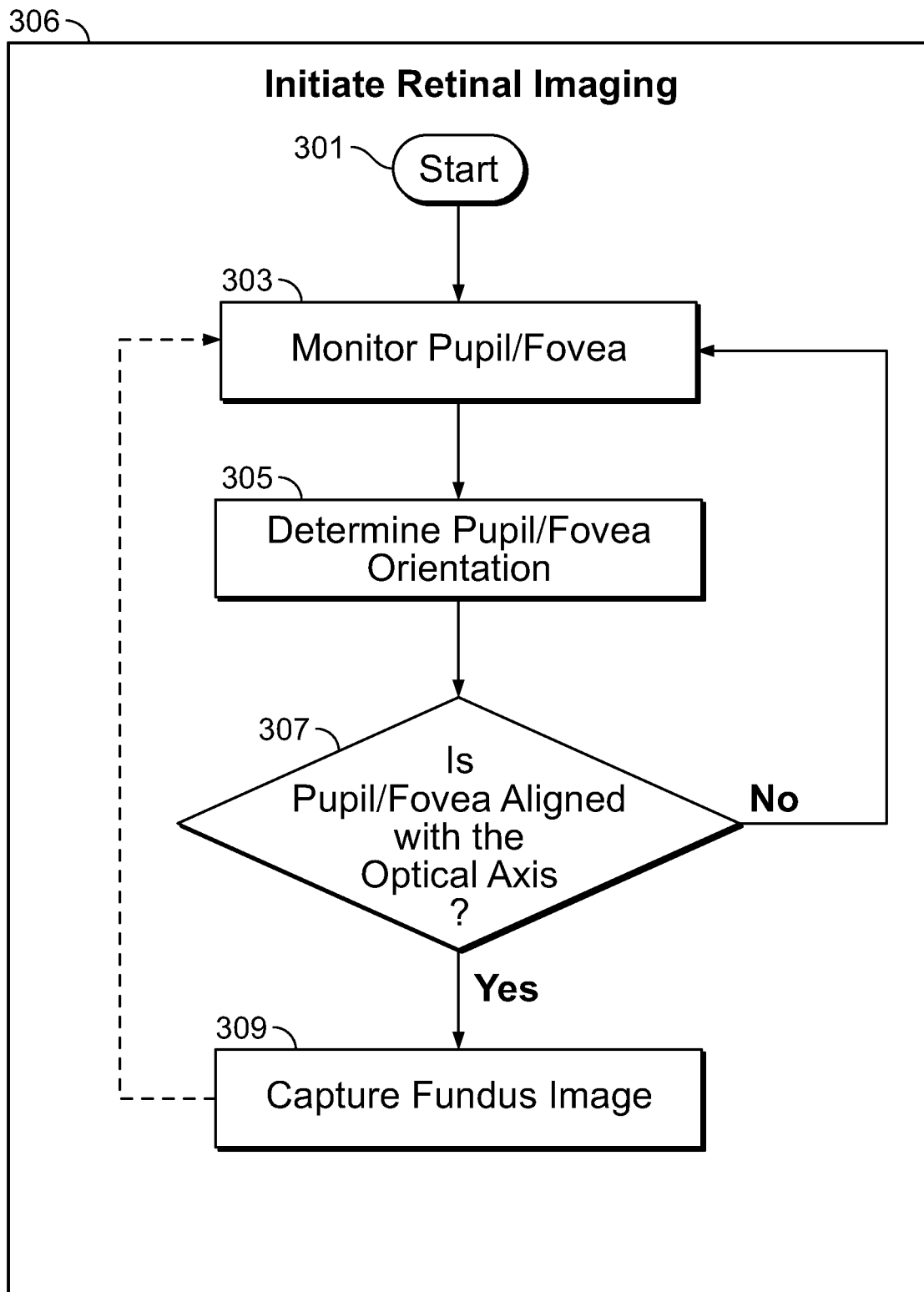
FIG. 5 illustrates an example method of initiating a fundus imaging using passive eye tracking.

FIG. 5 illustrates an alternate embodiment of initiate retinal imaging step 306 using passive eye tracking. The initiate retinal imaging step 306 operates to image the fundus of the patient P using passive eye tracking. In the initiate retinal imaging step 306, the fundus imaging system 102 monitors the pupil/fovea orientation of the patient P. Although the initiate retinal imaging step 306 is described with respect to fundus imaging system 102, the initiate retinal imaging step 306 may be performed using a wearable or nonwearable fundus imaging system, such as a handheld digital fundus imaging system.

Initially, at step 303, the pupil or fovea or both of the patient P are monitored. The fundus imaging system 102 captures images in a first image capture mode. In the first image capture mode, the fundus imaging system 102 captures images at a higher frame rate. In some embodiments, in the first image capture mode, the fundus imaging system 102 captures images with infra-red illumination and at lower resolutions. In some embodiments, the infra-red illumination is created by the illumination LED 182 operating to generate and direct light of a lower intensity towards the subject. The first image capture mode may minimize discomfort to the patient P, allow the patient P to relax, and allow for a larger pupil size without dilation (non-mydriatic).

Next, at step 305, the computing device 1800 processes at least a portion of the images captured by the fundus imaging system 102. The computing device 1800 processes the images to identify the location of the pupil or fovea or both of the patient P. Using the location of the pupil or fovea or both in one of the images, a vector corresponding to the pupil/fovea orientation is calculated. In some embodiments, the pupil/fovea orientation is approximated based on the distance between the pupil and fovea in the image. In other embodiments, the pupil/fovea orientation is calculated by approximating the position of the fovea relative to the pupil in three dimensions using estimates of the distance to the pupil and the distance between the pupil and the fovea. In other embodiments, the pupil/fovea orientation is approximated from the position of the pupil alone. In yet other embodiments, other methods of approximating the pupil/fovea orientation are used.

Next, at step 307, the pupil/fovea orientation is compared to the optical axis of the fundus imaging system 102. If the pupil/fovea orientation is substantially aligned with the optical axis of the fundus imaging system 102, the process proceeds to step 309 to capture a fundus image. If not, the process returns to step 303 to continue to monitor the pupil or fovea. In some embodiments, the pupil/fovea orientation is substantially aligned with the optical axis when the angle between them is less than two to fifteen degrees.

Next, at step 309, fundus images are captured by triggering the embodiment of example thru focusing image capturing method 200. In embodiments, five images are captured at step 309. In some embodiments, the fundus image is captured in a second image capture mode. In some embodiments, in the second image capture mode, the fundus imaging system 102 captures images with visible illumination and at higher resolutions. In some embodiments, the visible illumination is created by the illumination LED 182 operating to generate and direct light of a higher intensity towards the subject. In other embodiments, the higher illumination is created by an external light source or ambient light. The second image capture mode may facilitate capturing a clear, well-illuminated, and detailed fundus image.

Figure 6:
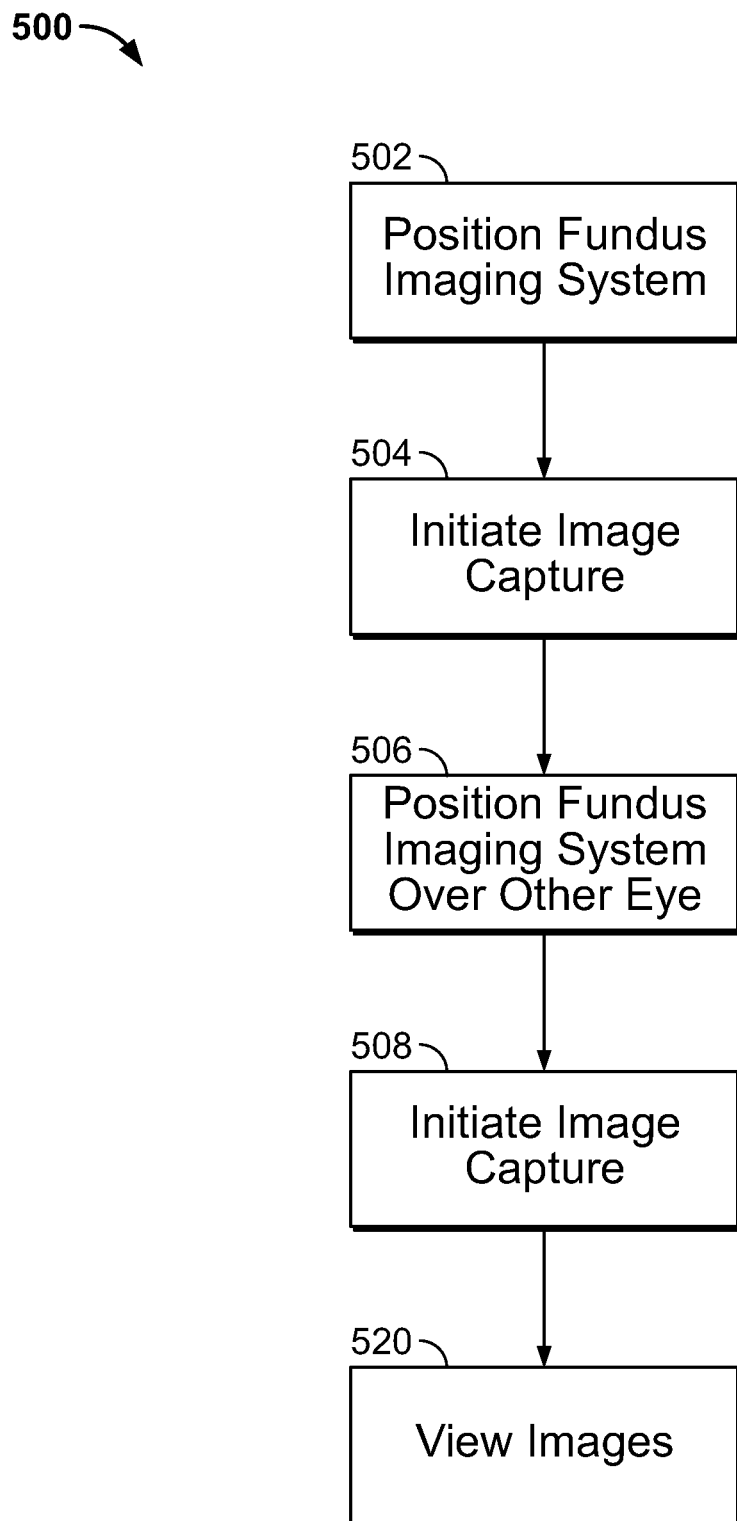
FIG. 6 is an embodiment of an example use of a fundus imaging system.

In some embodiments, after step 309, the initiate retinal imaging step 306 returns to step 303 to continue to monitor the pupil/fovea orientation. The initiate retinal imaging step 306 may continue to collect fundus images indefinitely or until a specified number of images have been collected. Further information regarding passive eye tracking can be found in U.S. patent application Ser. No. 14/177,594 filed on Feb. 11, 2014, titled Ophthalmoscope Device, which is hereby incorporated by reference in its entirety FIG. 6 is an embodiment of example use 500 of fundus imaging system 102. In the embodiment of example use 500, a clinician positions the fundus imaging system (operation 502), initiates image capture (operation 504), positions the fundus imaging system over the other eye (operation 506), initiates image capture (operation 508), and views images (operation 520). Although the example use 500 is conducted without first administering mydriatic pharmaceuticals, the example use 500 can also be performed for a patient who has taken a pupil-dilating compound. The embodiment of example use 500 can also include lowering the lighting. The embodiment of example use 500 is conducted using the same or similar components as those described above with reference to FIGS. 1-3. Other embodiments can include more or fewer operations.

The embodiment of example use 500 begins by positioning the fundus imaging system (operation 502). In embodiments, the clinician first initiates an image capture sequence via a button on the housing or a graphical user interface shown by the display. The graphical user interface can instruct the clinician to position the fundus imaging system over a particular eye of the patient. Alternatively, the clinician can use the graphical user interface to indicate which eye fundus is being imaged first.

In operation 502, the clinician positions the fundus imaging system near the patient's eye socket. The clinician positions the aperture of the system flush against the patient's eye socket such that the aperture, or a soft material eye cup extending from the aperture, seals out most of the ambient light. Of course, the example use 500 does not require positioning the aperture flush against the patient's eye socket.

When the fundus imaging system is in position, the system captures more than one image of the fundus in operation 504. As discussed above, the system does not require the clinician to manually focus the lens. Additionally, the system does not attempt to autofocus on the fundus. Rather, the clinician simply initiates the image capture, via a button or the GUI, and the fundus imaging system controls when to capture the images and the focus of the variable focus lens. Also, as discussed above at least with reference to FIG. 5, the system can initiate image capture using passive eye tracking.

The patient may require the fundus imaging system to be moved away from the eye socket during image capture operation 504. The clinician can re-initiate the image capture sequence of the same eye using the button or the GUI on the display.

After capturing an image in each of the specified zones, the fundus imaging system notifies the clinician that the housing should be positioned over the other eye (operation 506). The notification can be audible, such as a beep, and/or the display can show a notification. In embodiments, the system is configured to capture a set of images of only one eye, wherein the example method 500 proceeds to view images operation 520 after image capture operation 504.

Similar to operation 502, the clinician then positions the fundus imaging system near or flush with the patient's other eye socket in operation 506. Again, when the system is in place, an image is captured in every zone in operation 508.

After images have been captured of the fundus in each pre-set zone, the clinician can view the resulting images in operation 520. As noted above with reference to FIG. 3, the images can be post-processed before the clinician views the images to select or synthesize a representative image. Additionally, the fundus images can be sent to a remote location for viewing by a different medical professional.

Figure 7:
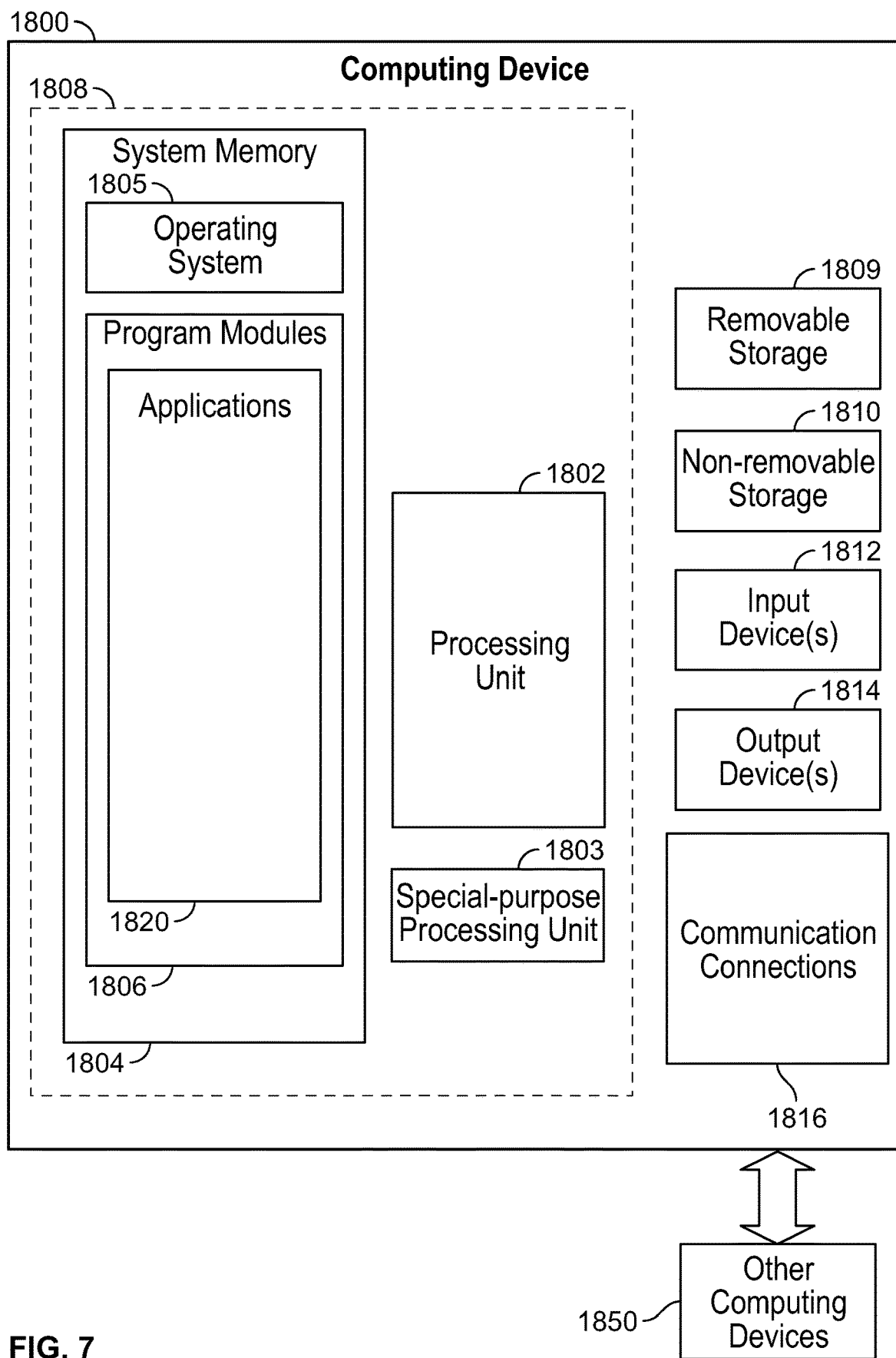
FIG. 7 is an example computing device used within the fundus imaging system.
Figure 8:
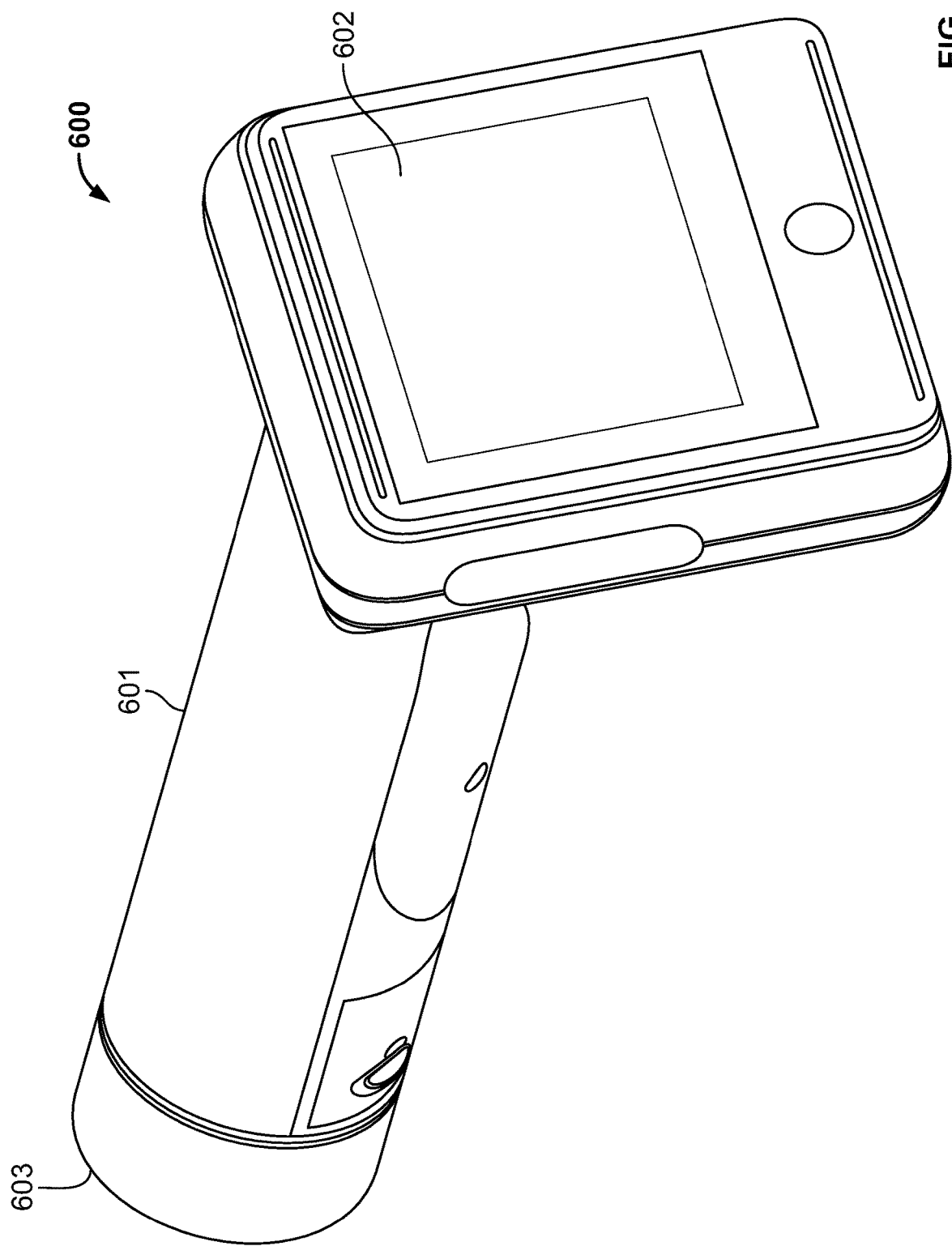
FIG. 8 is another embodiment of an example fundus imaging system.
Figure 9:
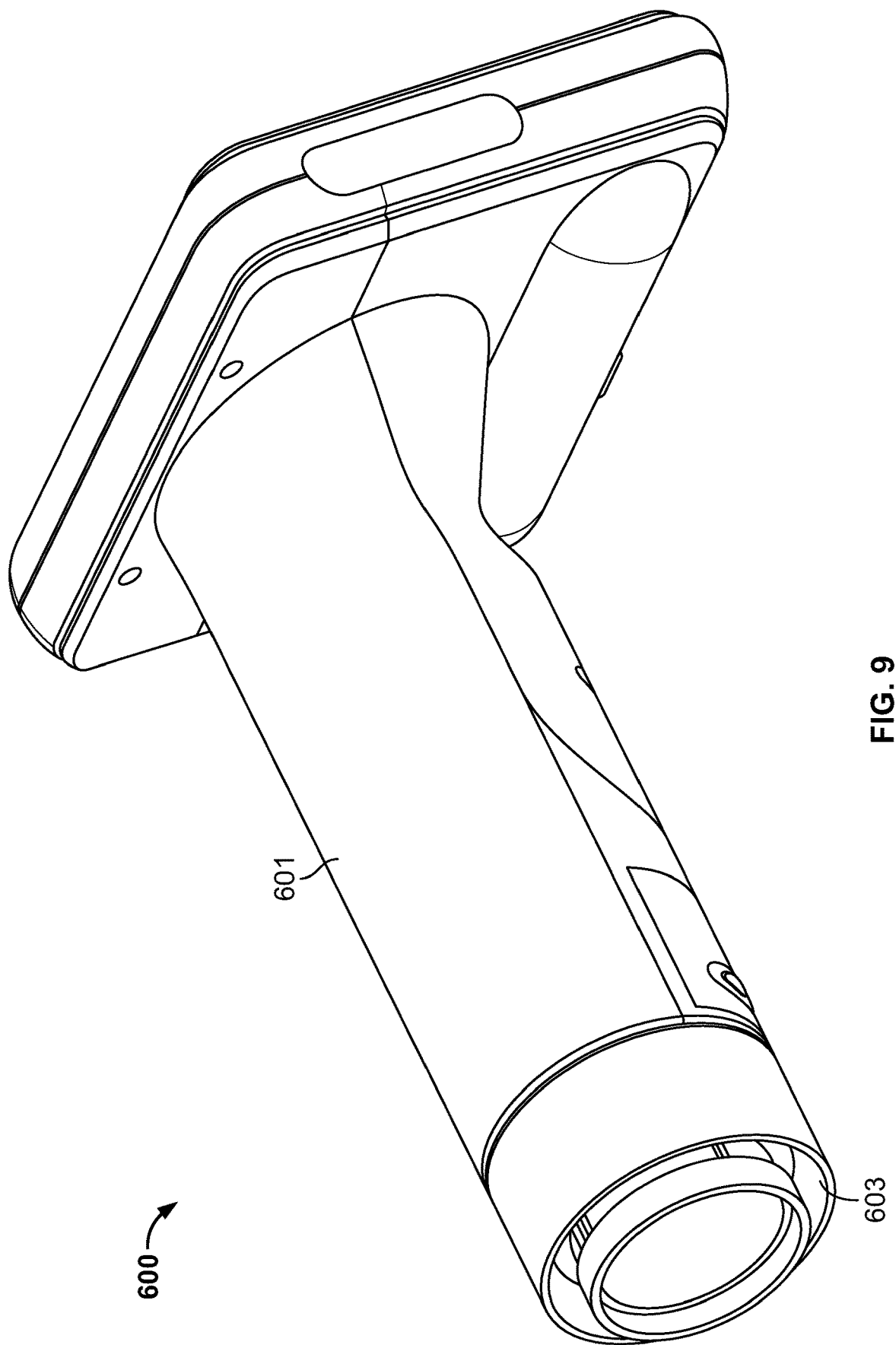
FIG. 9 is another view of the fundus imaging system of FIG. 8.
Figure 10:
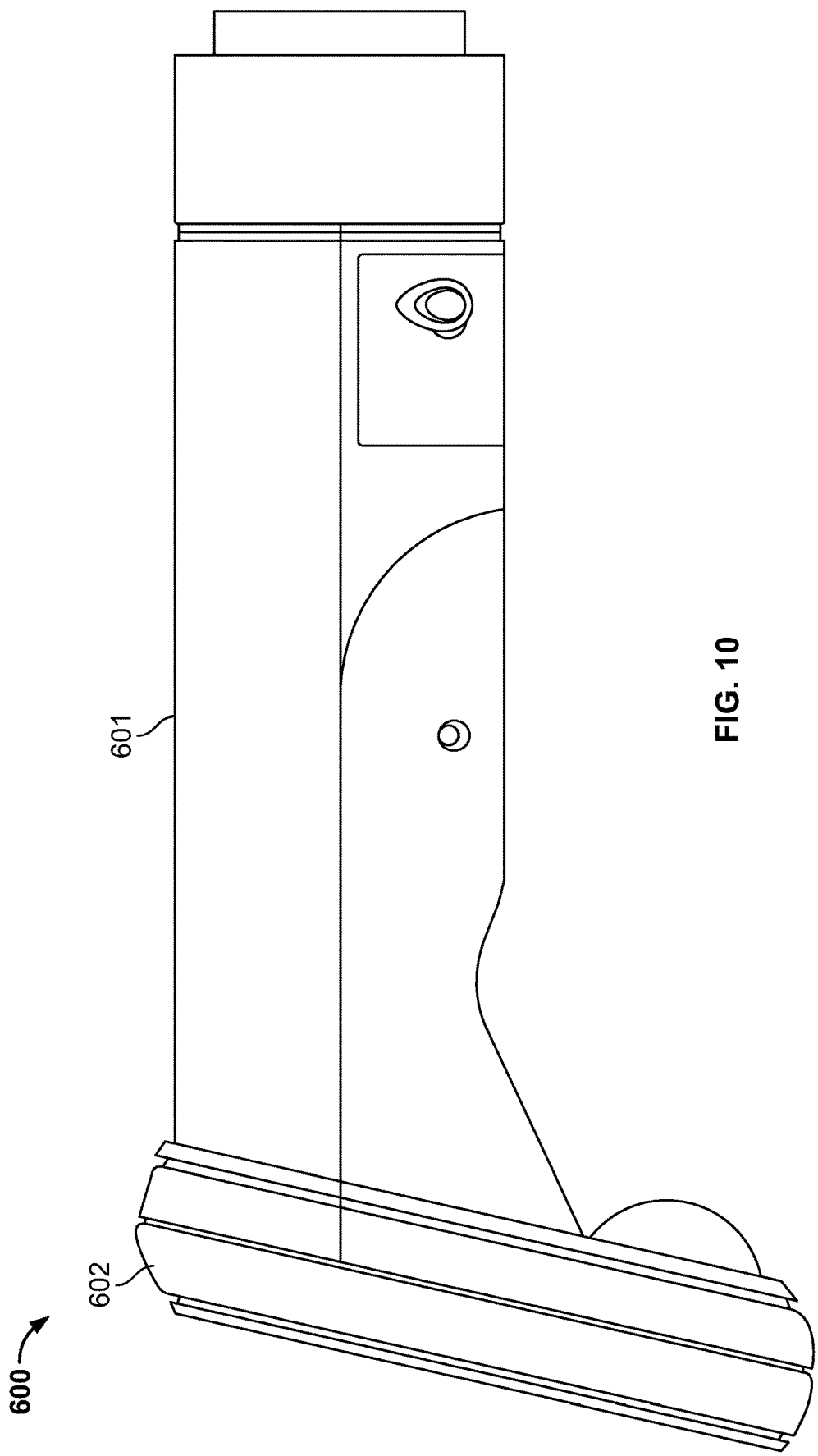
FIG. 10 is another view of the fundus imaging system of FIG. 8.
Figure 11:
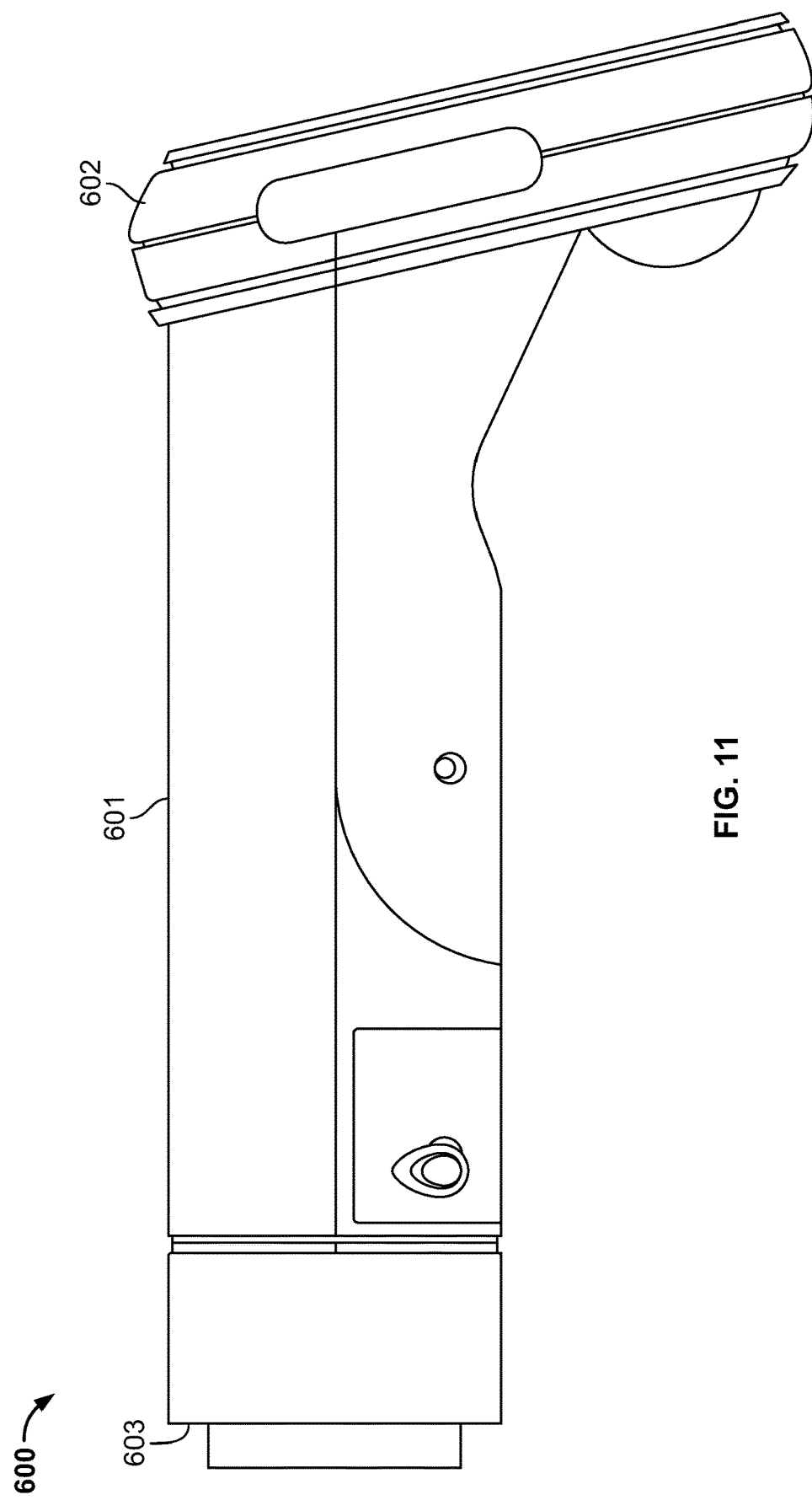
FIG. 11 is another view of the fundus imaging system of FIG. 8.
Figure 12:
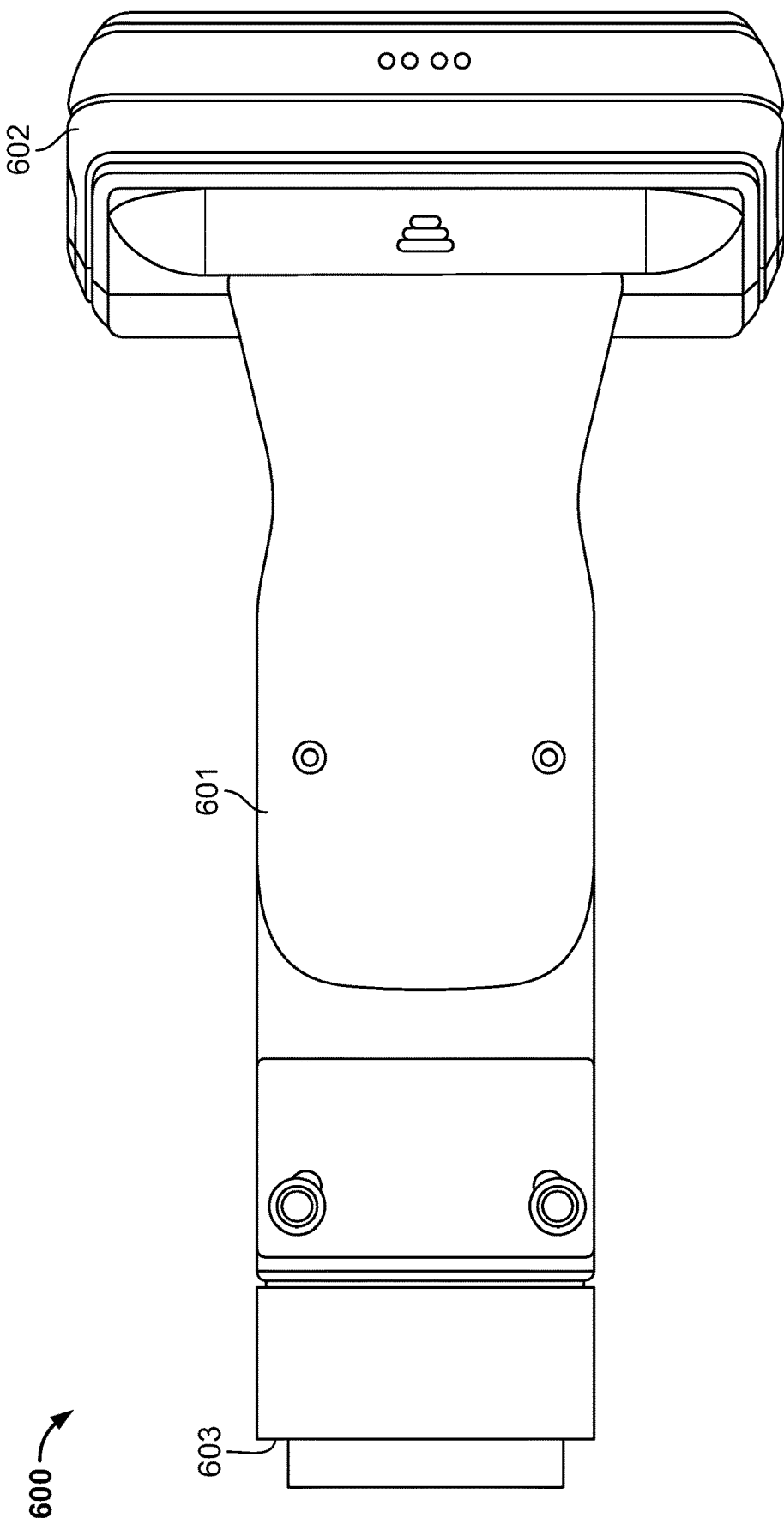
FIG. 12 is another view of the fundus imaging system of FIG. 8.
Figure 13:
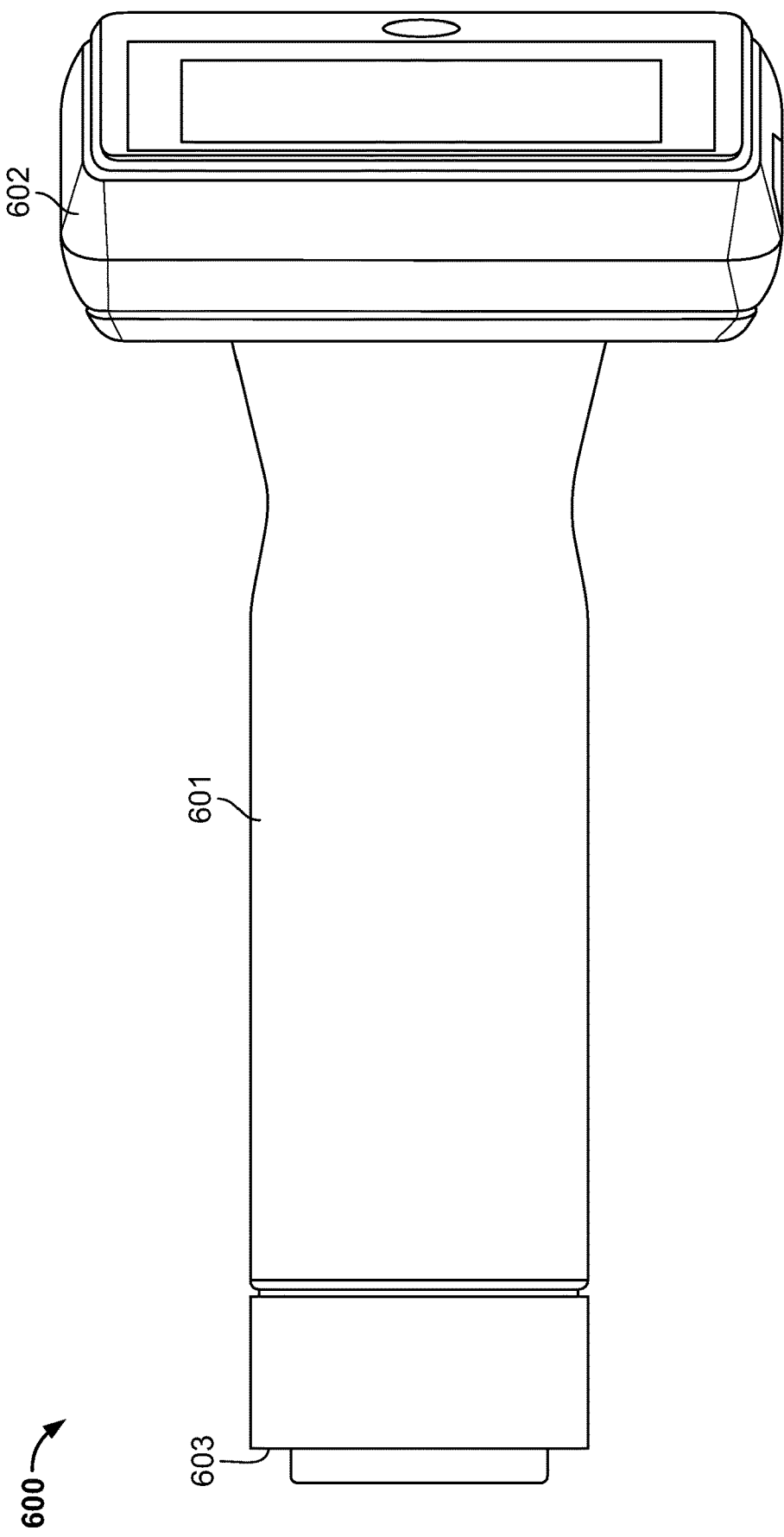
FIG. 13 is another view of the fundus imaging system of FIG. 8.
Figure 15:
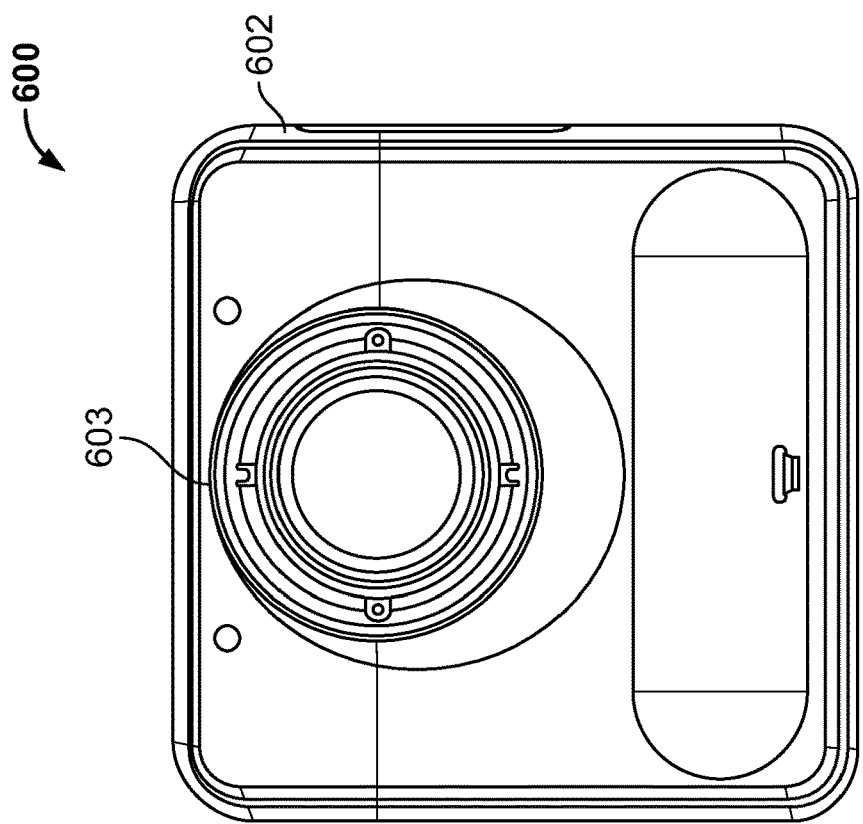
FIG. 15 is another view of the fundus imaging system of FIG. 8.
Figure 14:
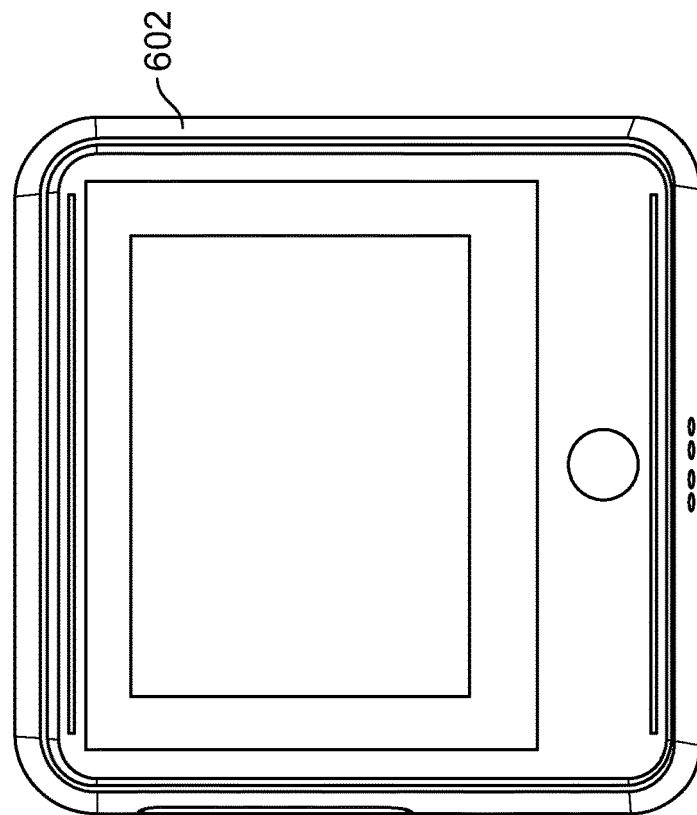
FIG. 14 is another view of the fundus imaging system of FIG. 8.
Figure 16:
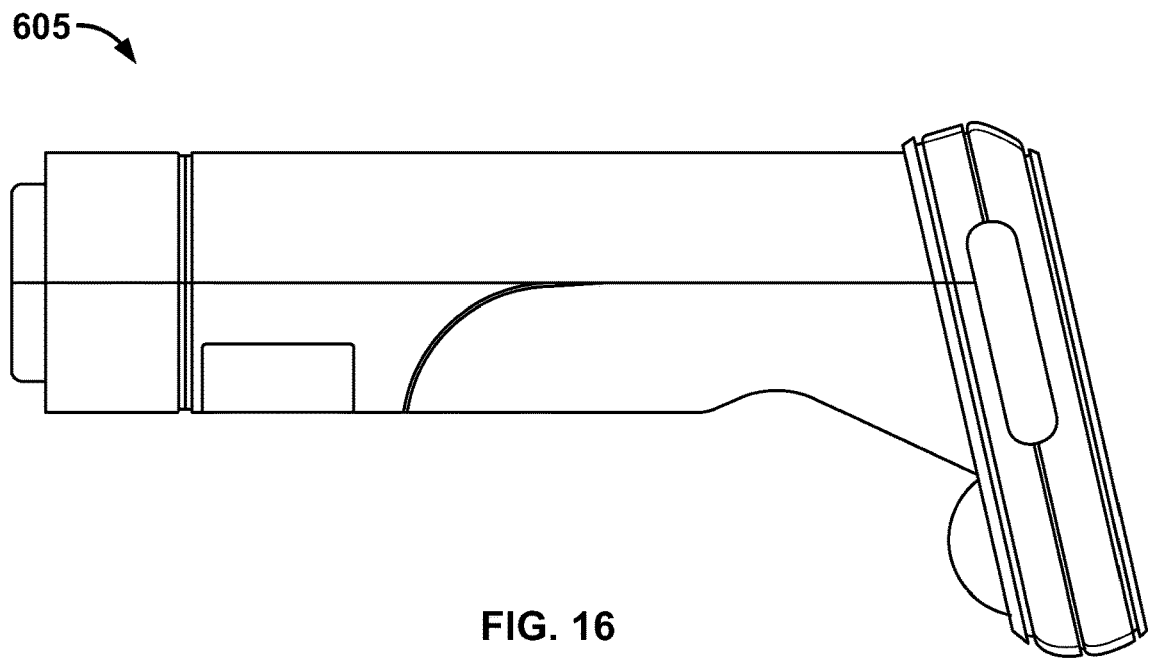
FIG. 16 is another embodiment of an example fundus imaging system.
Figure 17:
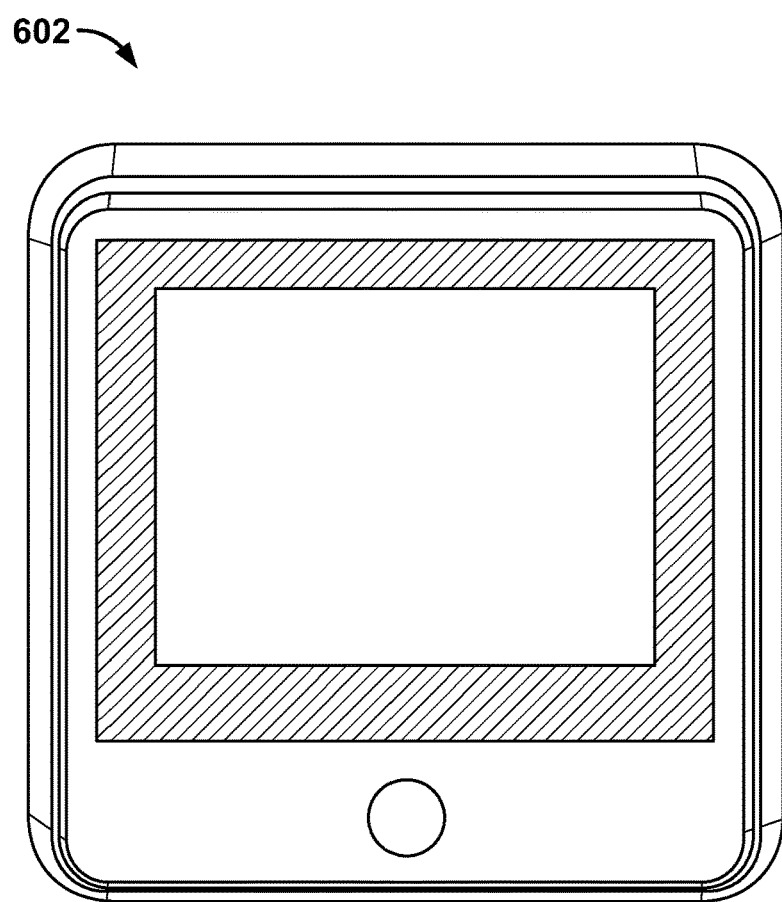
FIG. 17 is another view of the fundus imaging system of FIG. 16.
Figure 18:
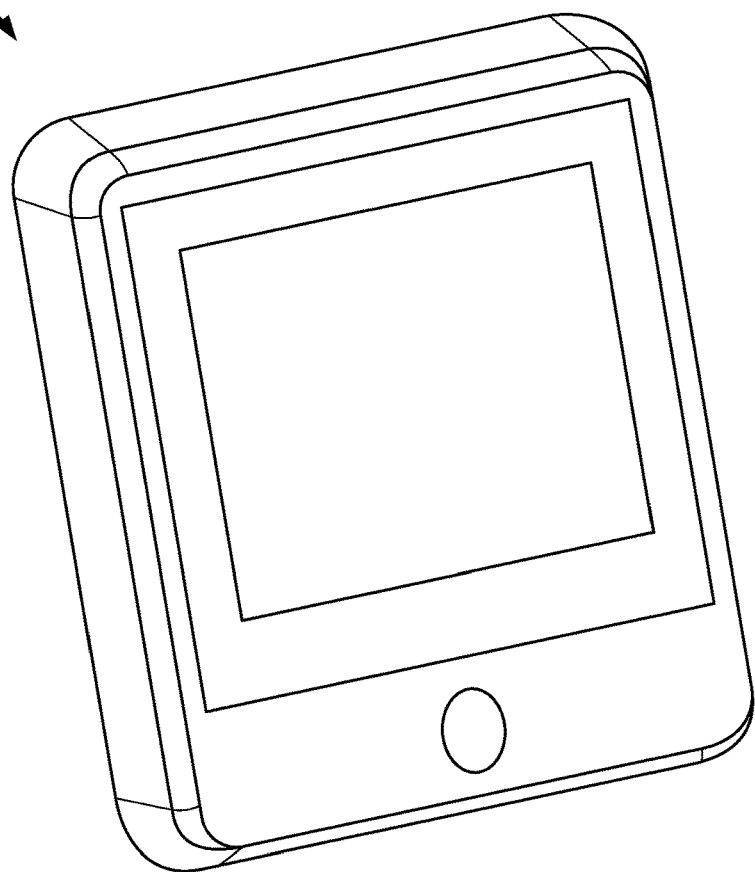
FIG. 18 is another view of the fundus imaging system of FIG. 16.
Figure 19:
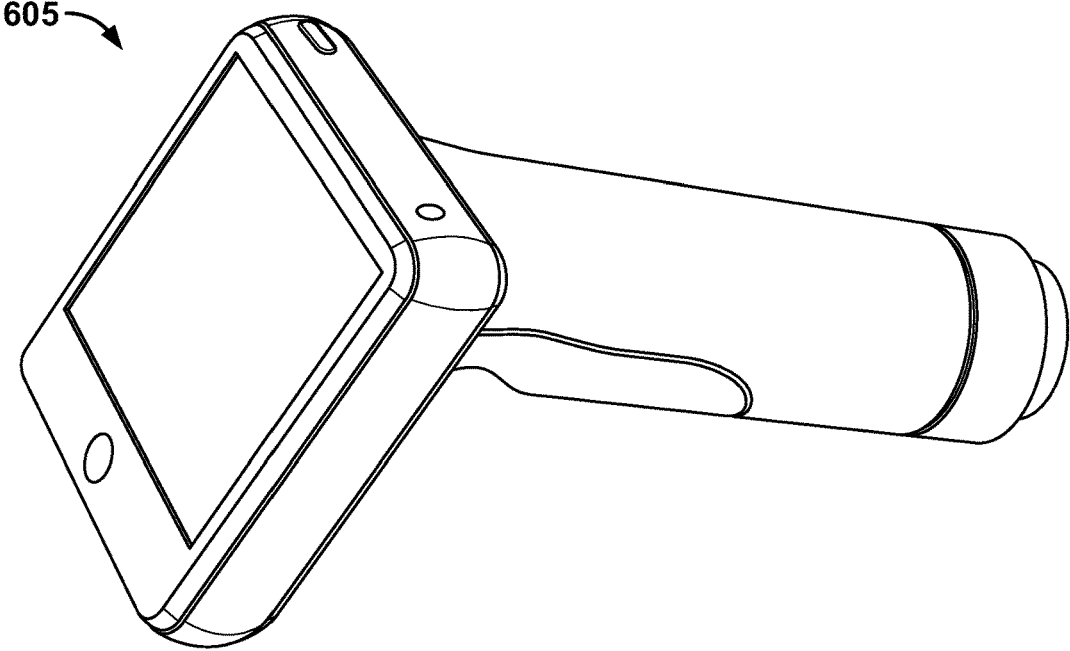
FIG. 19 is another view of the fundus imaging system of FIG. 16.
Figure 20:
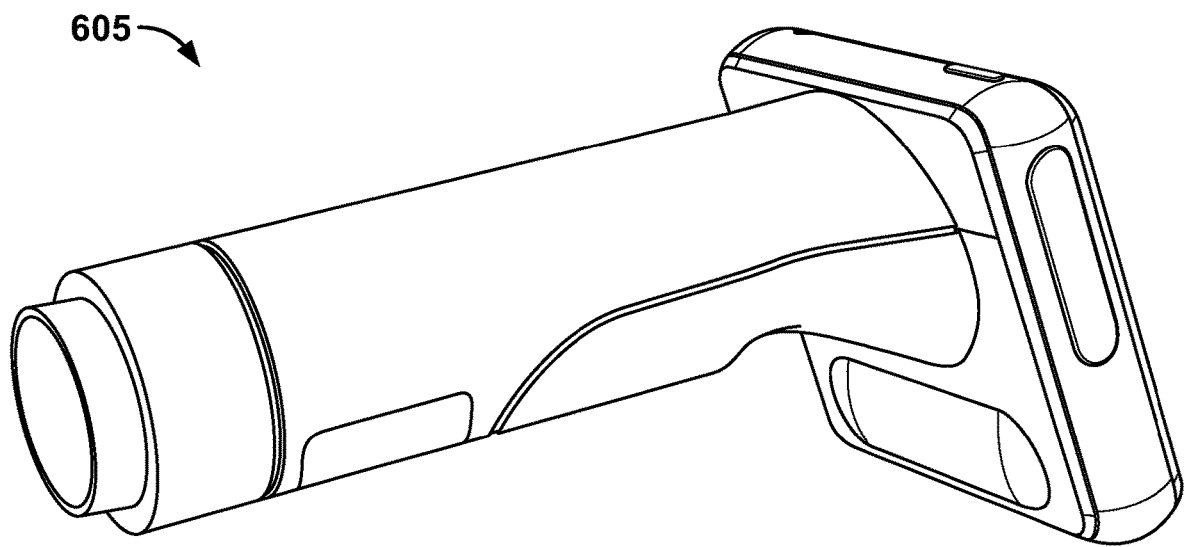
FIG. 20 is another view of the fundus imaging system of FIG. 16.
Figure 21:
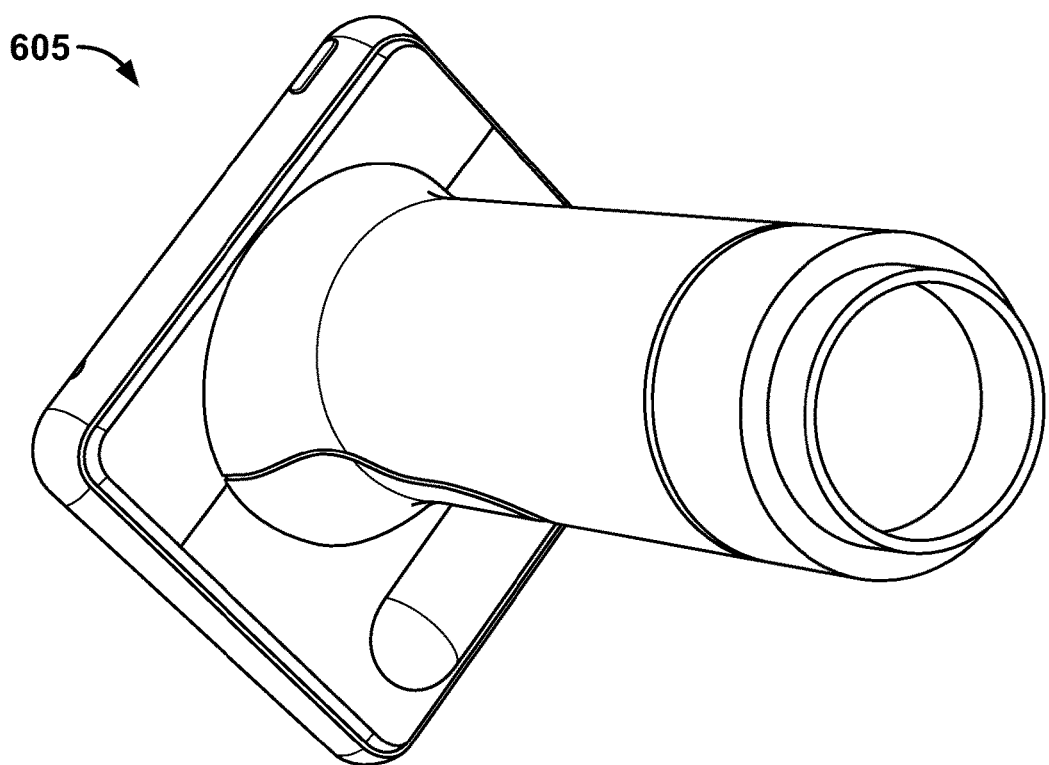
FIG. 21 is another view of the fundus imaging system of FIG. 16.
Figure 22:
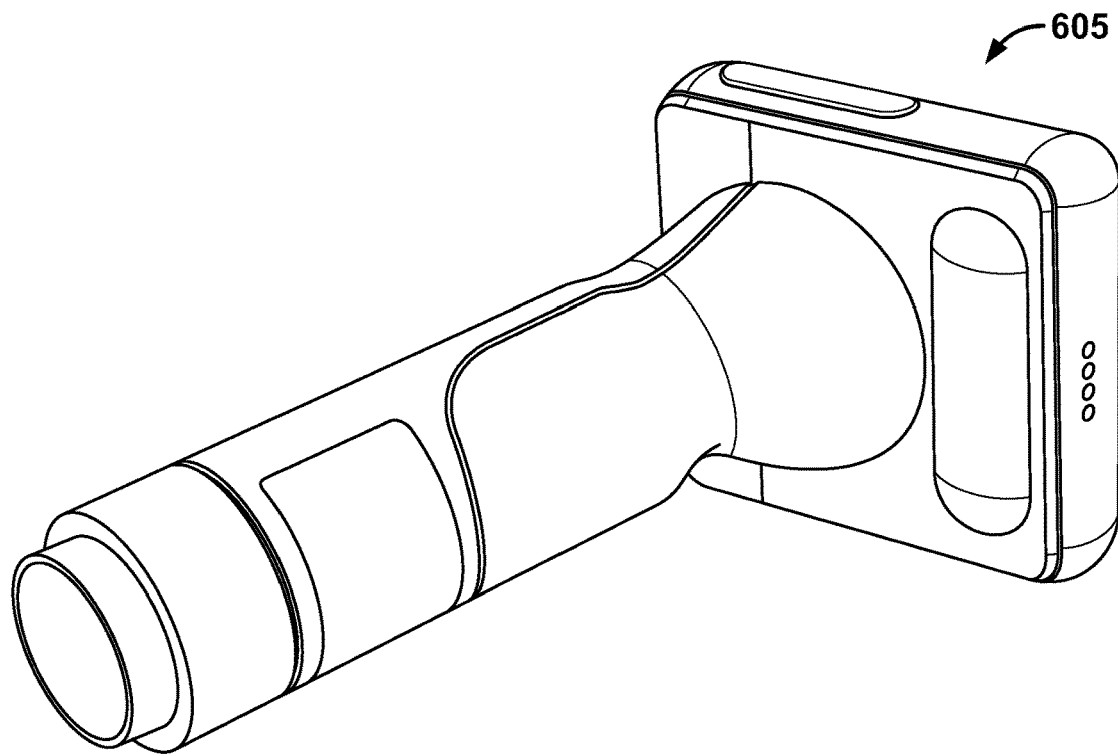
FIG. 22 is another view of the fundus imaging system of FIG. 16.
Figure 23:
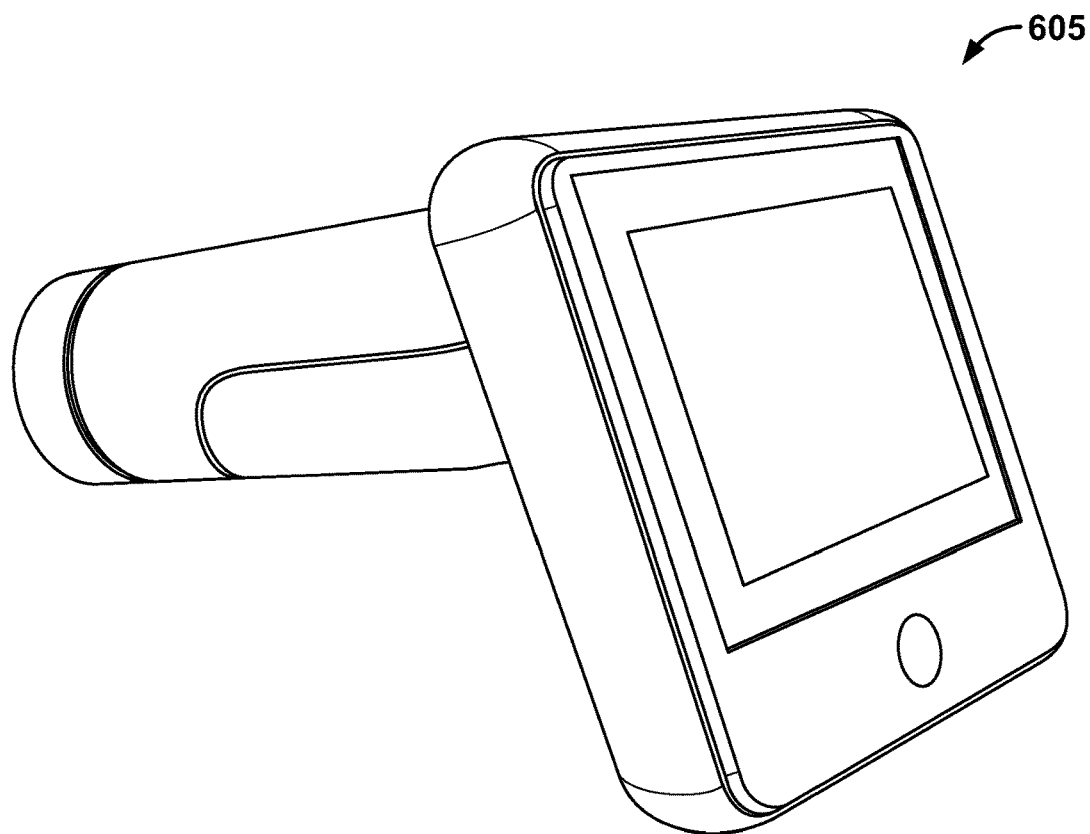
FIG. 23 is another view of the fundus imaging system of FIG. 16.
Figure 24:
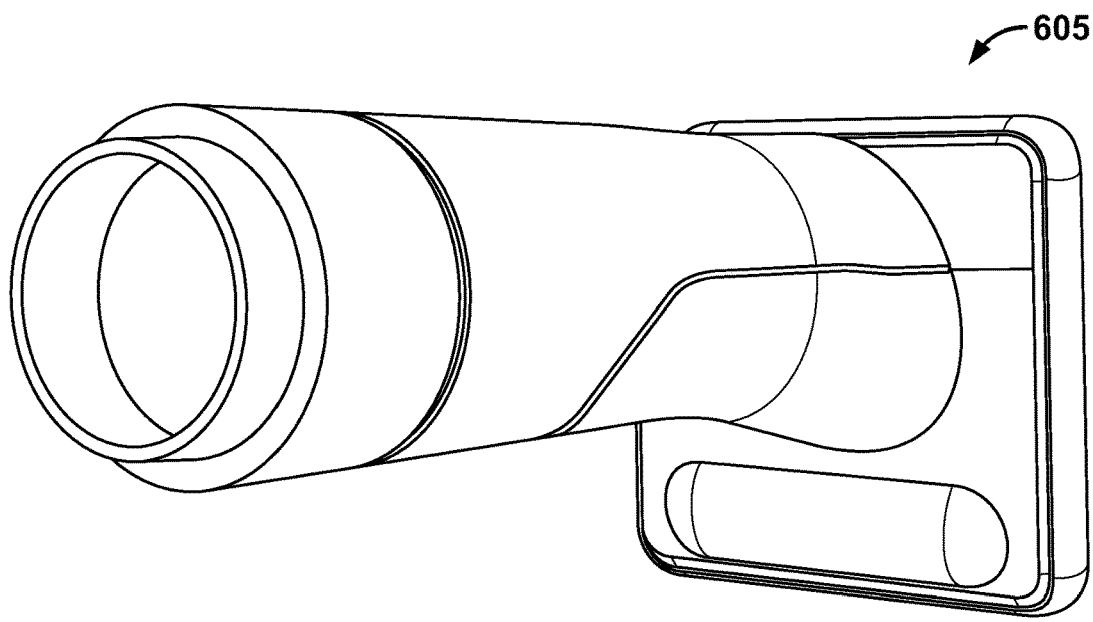
FIG. 24 is another view of the fundus imaging system of FIG. 16.
Figure 25:
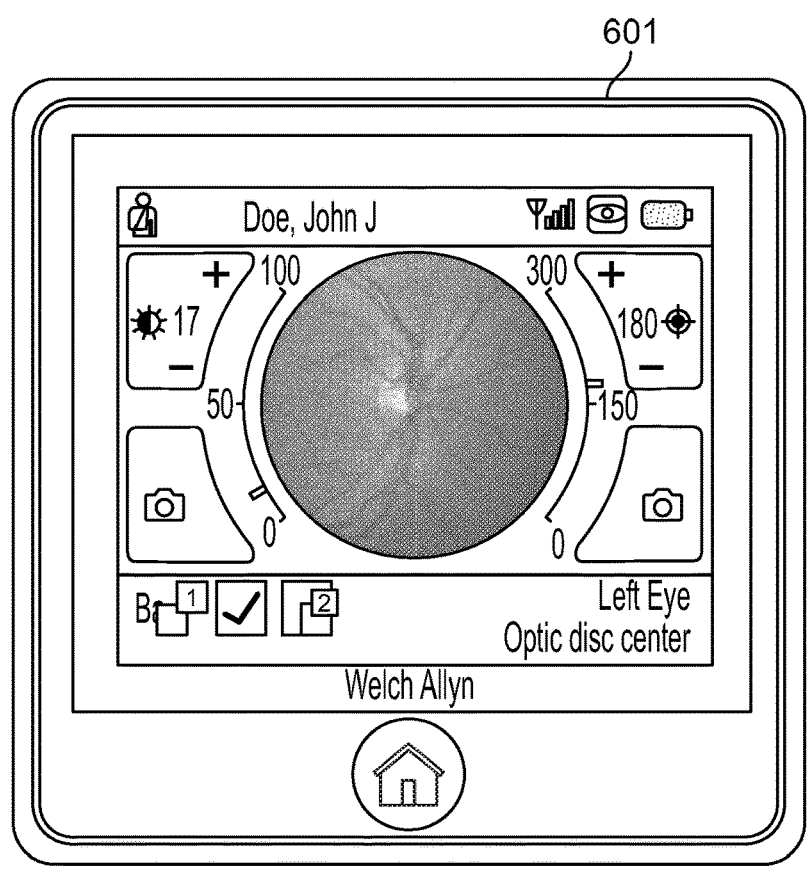
FIG. 25 is another view of the fundus imaging system of FIG. 16.

FIG. 7 is a block diagram illustrating physical components (i.e., hardware) of a computing device 1800 with which embodiments of the disclosure may be practiced. The computing device components described below may be suitable to act as the computing devices described above, such as wireless computing device and/or medical device of FIG. 1. In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 7 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated in FIG. 7 by a removable storage device 1809 and a non-removable storage device 1810.

As stated above, a number of program modules and data files may be stored in the system memory 1804. While executing on the at least one processing unit 1802, the program modules 1806 may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 7 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812 such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices. Examples of suitable communication connections 1816 include, but are not limited to, RF transmitter, receiver, and/or transceiver circuitry; universal serial bus (USB), parallel, and/or serial ports.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5; etc. This same principle applies to ranges reciting only one numerical value. Furthermore, such an interpretation should apply regardless of the breadth of the range or the characteristics being described.

Referring now to FIGS. 8-15, another example fundus imaging system 600 is shown. The embodiment 600 is similar to the fundus imaging system 400 described above.

The fundus imaging system 600 includes a housing 601 that supports a display 602 at a first end and an opposite end 603 configured to engage an eye of the patient. As described herein, the fundus imaging system 600 can be used to implement one or more of the described methods for imaging of the fundus.

Figure 26:
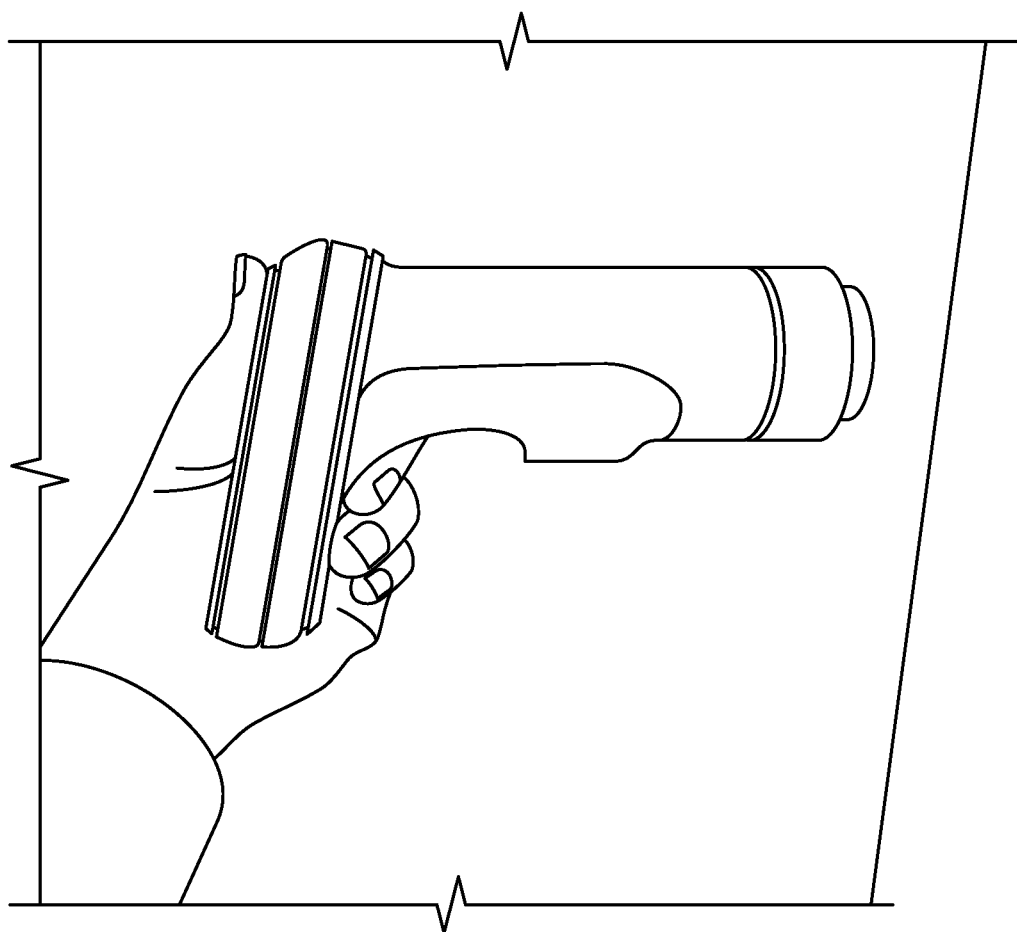
FIG. 26 is another view of the fundus imaging system of FIG. 16.

Yet another embodiment of an example fundus imaging system 605 is shown in FIGS. 16-26. In this example, the body of the fundus imaging system 605 can be formed of two or more materials overmolded upon one another. For example, a first polymeric material can be used to form the main body, and a second, softer polymeric material can be overmolded onto the first material to form bumper and/or grip areas, as depicted in FIG. 26. These overmolded areas provide a softer and slip-resistant surface for easier grasping and holding of the fundus imaging system 605. The multiple gripping surfaces allow the clinician C to decide how best to hold the fundus imaging system 605 in use.

Figure 27A:
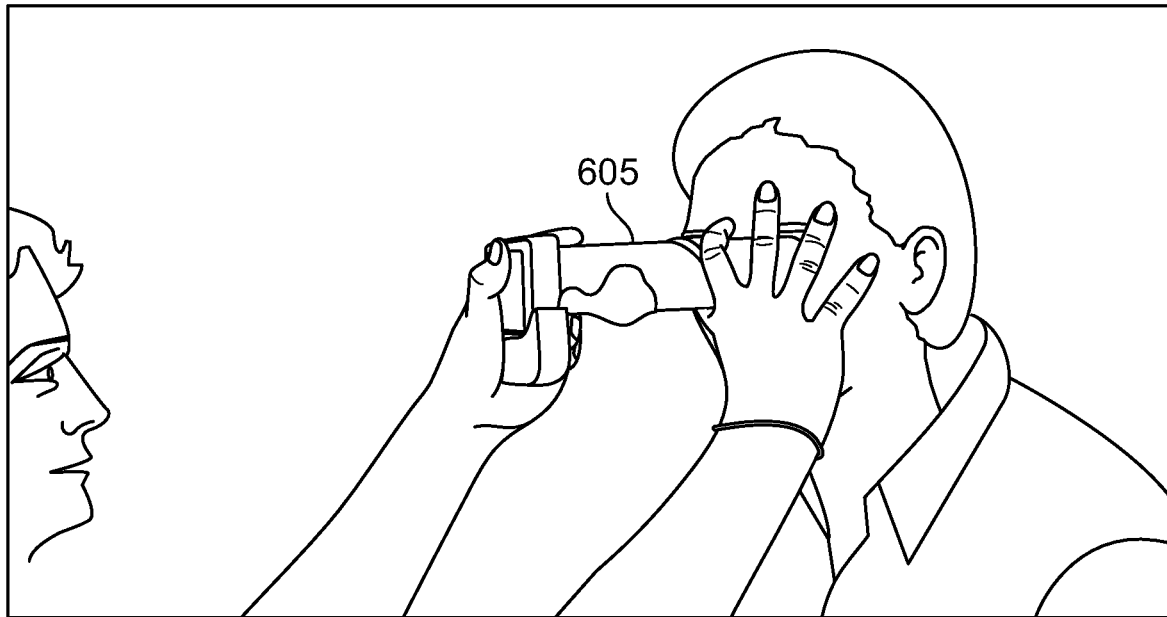
FIGS. 27A and 27B are other views of the fundus imaging system of FIG. 16 in use with a patient.
Figure 27B:
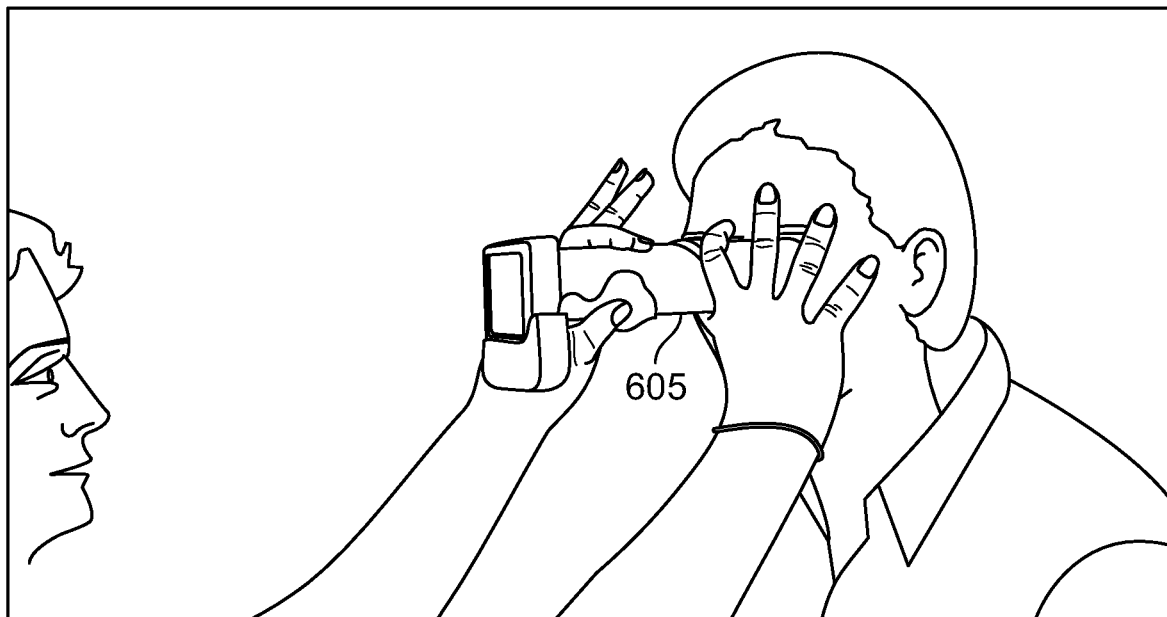
Figure 29:
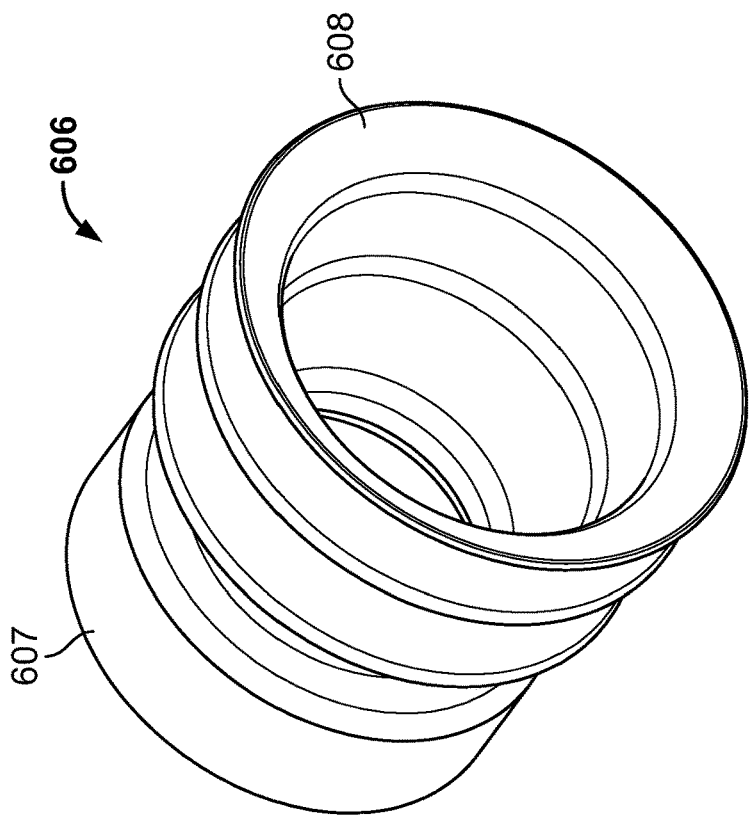
FIG. 29 is another view of the eye cup of FIG. 28.
Figure 28:
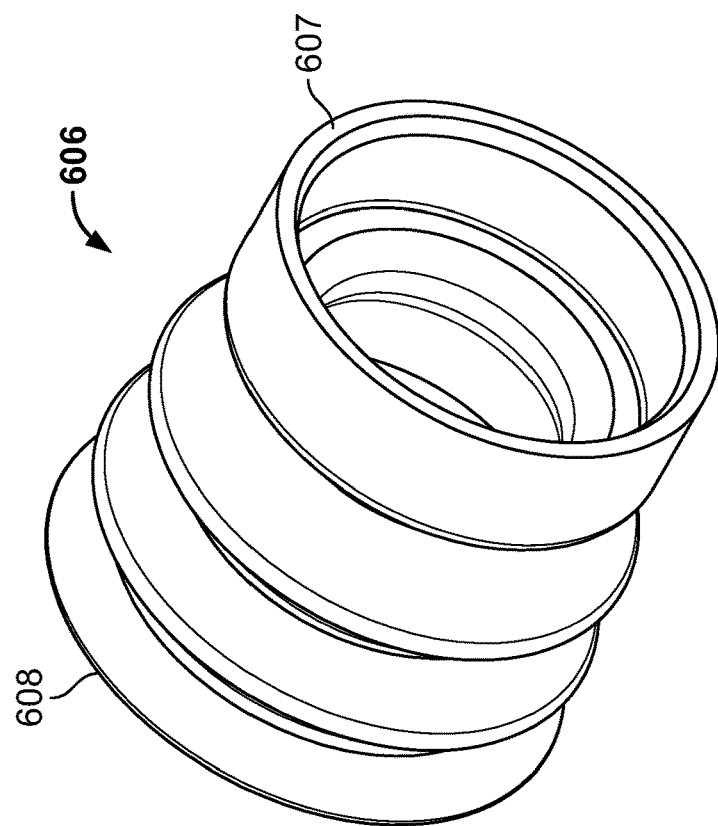
FIG. 28 is an embodiment of an example eye cup for use with the fundus imaging system of FIG. 8.

Referring now to FIGS. 27A and 27B, the fundus imaging system 605 is shown in use on the patient. The fundus imaging system 605 is placed with an end (e.g., opposite end 603) adjacent to or touching the patient's face surrounding the desired eye socket.

Specifically, an end 607 of an example eye cup 606, shown in FIGS. 28-32, is positioned at the end 603 of the fundus imaging system 600 or 605. An opposite end 608 is positioned again the eye socket surrounding the eye for which imaging will occur. In this example, the eye cup 606 is formed of a polymeric material that is flexible in an accordion-like manner. This allows the fundus imaging system 600 or 605 to be moved by the clinician C towards and away from the patient's eye while still maintaining contact with the patient's face. Other configurations are possible.

Figure 33:
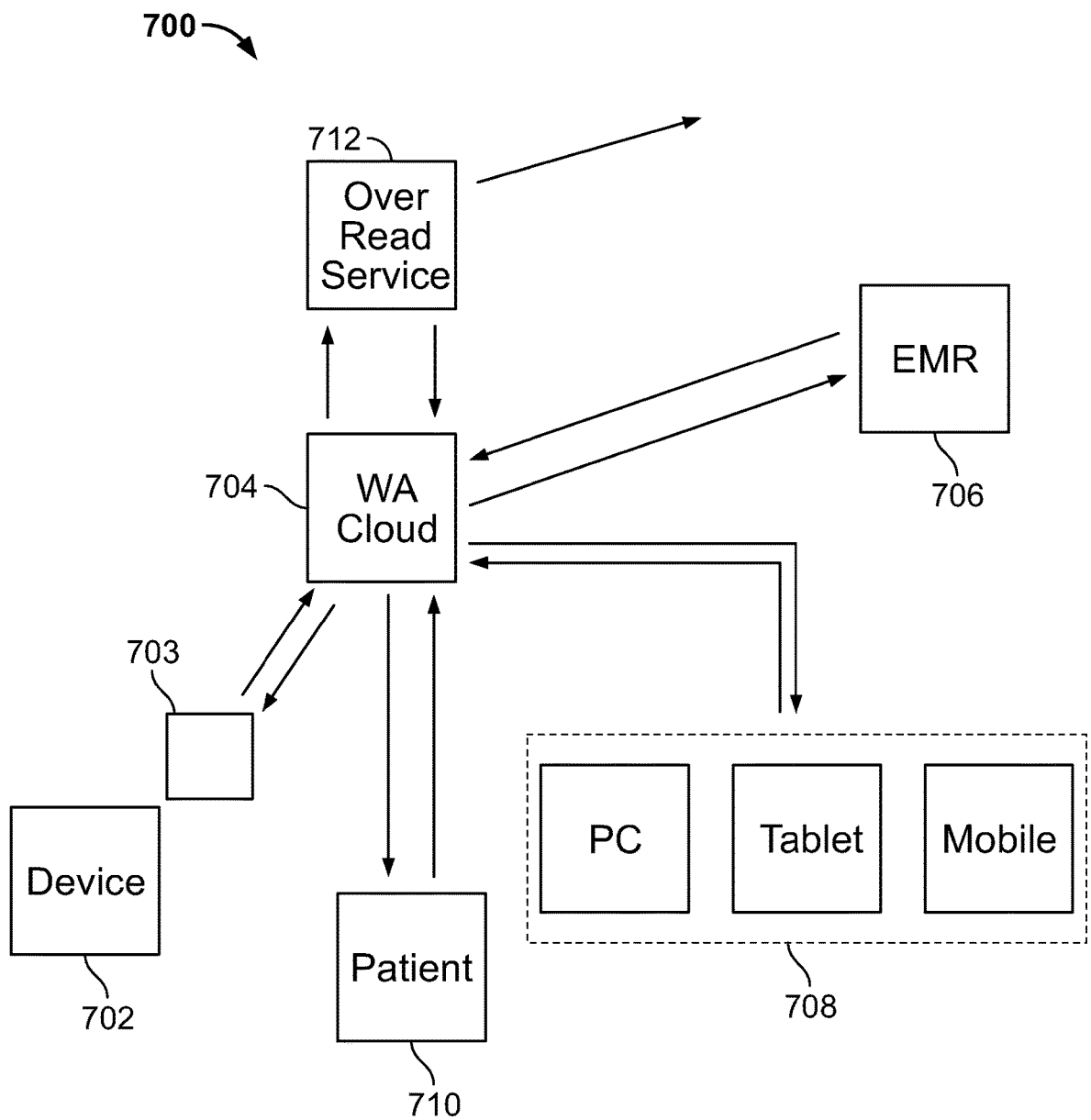
FIG. 33 is another embodiment of an example system for recording and viewing an image of a patient's fundus.

In another example system 700 for recording and viewing an image of a patient's fundus shown in FIG. 33, the system 700 is cloud-based (e.g., includes a plurality of servers with storage accessible from a large network such as the Internet) and allows for communication and storage of fundus images across LANs, WANs, and the Internet. In this example, a device 702, which is identical and/or similar to the systems 600, 605 described above, can be used to capture an image, associate that image with a patient, review the image, and annotate the image as desired.

Upon completion, the image can be uploaded to a cloud system 704 using a batch or more instant configuration. When uploaded, the image can be tagged with device and patient information, such as a barcode associated with the patient and/or a patient picture. The cloud system 704 can be configured to provide patient lists and to accept or reject an image based upon given criteria, such a patient name and quality of image. The cloud system 704 can also be used to provide notifications, such as image availability, to the clinician C and/or patient. In addition, the cloud can forward the image and patient information to an EMR 706 for storage.

In addition, the cloud system 704 can be used to provide a portal to allow for access to images by a device 708 of the clinician C and/or patient device 710 using a computing device such as a personal computing device, tablet, and/or mobile device. This can allow the images to be viewed, manipulated, etc. The cloud system 704 can be used to capture clinician C annotations and diagnoses. In addition, the cloud system 704 can be configured to interface with other third parties, such as insurance companies to allow for billing.

In some examples the systems 600, 605 can be configured to operate in both manual and automatic modes when interfacing with the cloud system 704. In one example, the automatic mode includes one or more scripts that automate certain processes for the systems 600, 605. See FIG. 36 described below. These processes can include automation of image focus and capture (acquisition) and output to the cloud for storage. In the manual mode, the various processes can be manually controlled by the clinician C, such as focus on the fundus, capture of one or more images at desired times, and then uploading of the image(s) to the cloud. See FIG. 37 described below.

A notification scheme is used for charging of the systems 600, 605. In these examples, the systems 600, 605 are wireless and include a rechargeable battery pack, such as a lithium-ion battery or similar battery. In this example, a bi-color LED is used to indicate a status of charging of the battery pack when placed in a charging cradle 703. The LED is left off if charging is not occurring—this is the default state. When the systems 600, 605 are charging (e.g., when plugged into a dock), the LED is illuminated a solid amber to indicate charging of the battery and a solid green when the battery charging is completed. If an error occurs during charging, the LED flashes an amber color. Other configurations are possible.

Different example operating states for the fundus imaging systems 600, 605 are possible. For a clinician that gathers the images from the patient, the systems 600, 605 can be used to select a patient, adjust the eye cap, take an image, determine a quality of the image, and review the status of an image capture process. In addition, various other features, such as adjustment of connectivity (e.g., WiFi) and cleaning of the device can be accomplished. Additional details on some of these processes are provided below.

Further, a physician (sometimes the same individual who captured the images or a different individual, such as an individual located at a remote location) can review the results of the image captures and develop/review a report based upon the same. See FIG. 45 described below.

Example processes are performed in the cloud system 704 based upon each individual or service within the system. For the clinician capturing the images, the cloud system 704 can be used to add new patients, schedule the procedure, and check the status of the procedure. For the physician reviewing the images, the cloud system 704 can be used to check status, review the images, and generate/review a report based upon review of the images. Notifications can also be created and sent to, for example, the clinician or patient.

The systems 600, 605 can be used to transmit scheduling and/or image information to and from the cloud system 704. The EMR 706 is in communication with the cloud system 704 to transmit and store image and diagnoses information for each patient. Other configurations are possible.

An over read service 712 is also shown in FIG. 33. The over read service 712 can interact with the cloud system 704 to provide additional resources for analyzing the images, including reading of images and generating of reports. Other functions of the example system 700 include capture and forwarding of images to the cloud and communication between the cloud and the EMR 706 for storage thereof.

For example, in one embodiment, the device 702 is used to capture one or more fundus images. After capture, the device 702 is returned to the charging cradle 703. Upon placement of the device 702 into the cradle 703, the captured images are automatically transferred to the cloud system 704. This transfer can be automated, so that no further action is required by the user to transfer the images from the device 702 to the cloud system 704.

Upon submission to the cloud system 704, the images can be automatically reviewed for quality. The images can also be automatically forwarded to the over read service 712 for review. One or more clinicians can thereupon review the images and provide feedback from the over read service 712 back to the cloud system 704. At this point, the cloud system 704 can provide notification to the devices 708, 710 regarding the information from the over read service 712.

An example method for using the systems 600, 605 to capture fundus images includes preliminary tasks such as the capturing of patient vitals and education of the patient on the procedure are done. Once this is done, the system 600, 605 is powered on and the patient is selected on the device. The eye cup is then positioned on the patient and one or more images are captured using automated and/or manual processes. The images can then be checked. If accepted, the images are saved and/or uploaded to the cloud. The system 600, 605 can be powered off and returned to its cradle for charging. A physician can thereupon review the images, and the clinician C or patient can be notified of the results.

In an example method for obtaining a good quality image of the fundus using the systems 600, 605, after an image is captured, the clinician can accept or reject the image. If rejected, a script can be executed that provides manual or automated instructions on how to capture a desired image quality. The clinician thereupon gets another opportunity to capture an image and then to accept or reject it. If the image is accepted, automated processes can be used to determine a quality of the image. If accepted, further scripting can occur. If not, the clinician can be prompted to take another image.

An example method is provided to allow for capture of images even when the system 600, 605 loses connectivity with the cloud. In such an instance, automated quality checks may not be provided, and the clinician may be prompted as such. The clinician can then decide whether or not to accept the image without the quality check or to cancel the procedure. In addition, the system 600, 605 can be used to trouble shoot connectivity issues, as described further below.

An example method for allowing the clinician to select the patient on the system 600, 605 includes a work list that is provided that identifies patients based upon one or more given criteria, such as the clinician, location, time of day, etc. The clinician is thereupon able to select the patient and confirms the proper patient has been selected, such as by comparing a code with one worn by the patient for from a picture of the patient. Thereupon, after selection of the patient, one or more images can be captured and stored. The captured images are associated with the selected patient.

In a similar manner, an example method allows the clinician to assure that the proper patient is selected. Upon power-up of the system 600, 605, unique information is sent to the cloud, such as the system's serial number. The could looks-up the serial number and returns a list of patients associated with that system. The clinician can thereupon select the patient from the list or manually enter the patient into the system 600, 605 if the patient is not on the work list.

A user interface allows the user to pick between a selection of patients, examinations, review, and settings. If a patient is selected, the system 600, 605 proceeds with imaging of the fundus using an automated and/or manual process. Icons are used to represent different contexts on the user interfaces of the system 600, 605.

The following example workflows/methods are implemented by the systems 600, 605. Additional details regarding these workflows can also be found with reference to FIGS. 36-44.

An example method for automatic examination and image capture starts when the clinician selects the examination icon on the system 600, 605. Upon initiation, the clinician is presented with an interface that allows for automatic acquisition of the fundus image. This can be accomplished in three stages, including pre acquisition, acquisition, and post-acquisition. During pre-acquisition, the clinician selects the patient and configures the system as desired. During acquisition, the image is captured using automated or manual processes. Finally, post-acquisition, quality checks are performed and the clinician can save the image(s) if desired. See FIG. 36 described further below.

An example method for adjusting certain settings of the system 600, 605 includes, for example, brightness and focus, which can be selected automatically or manually manipulated by the clinician.

An example method for manually acquiring an image is similar to the method described above, except the acquisition of the images is done manually by the clinician. This is accomplished by the clinician manually indicating when an image is to be taken. Upon capture, the image can be verified manually or automatically.

An example method for navigating one or more captured images includes a user interface that is used to scroll through the captured images in a sequence. Upon review, the images can be submitted, if desired.

An example method for selecting a patient from a worklist starts upon selection of the patient icon from the interface for the system 600, 605. A list of patients is presented to the clinician in the worklist. The clinician can select a patient from the list to be presented with additional information about that patient, such as full name, date of birth, and patient ID. If any unsaved images exist, those images are associated with the selected patient. If not, a new examination routine is executed to allow for capture of images to be associated with the selected patient.

An example method allows for the clinician to manually enter new patient information into the system 600, 605. This includes patient name, date of birth, and/or patient ID. Once entered, the patient information can be associated with captured images.

An example method allows the clinician to search for a specific patient using such parameters as patient name, date of birth, and/or patient ID. Once found, the clinician selects the patient for further processing.

An example method for refreshing the patient worklist includes assuming there is connectivity (e.g., to the cloud), the clinician selecting a refresh button to manually refresh the list with the most current patient names. The system 600, 605 is also programmed to periodically refresh the list automatically at given intervals and at other given periods, such as upon startup or shutdown. Other configurations are possible.

An example method allows a clinician to review a patient test on the system 600, 605. Upon selection of a patient, the clinician can review patient summary information (e.g., full name, date of birth, and patient ID) and previous examination summary information, such as items from the examination and image quality scores, which indicate how good the image quality was from those examinations.

An example method for saving images allows, after acquisition, the clinician to review the images in sequence. For each image in the workspace, the image is quality-checked and the status of the image is displayed to the clinician. The clinician uses the user interface to review each acquired image and to save or discard the image.

An example method labeling eye position allows the clinician to select upon five eye positions, including off (default), left eye optic disc centered, left eye macula centered, right eye macula centered, and right eye optic disc centered.

An example method allows for manual adjustment of settings for image acquisition. In this example, the clinician has access to various settings that can be adjusted manually, such as PET and focus and brightness. See FIG. 38 described below.

An example method for adding images includes, once an image is captured, the clinician manually adding the image to a workspace if desired. Once added, the image can be reviewed and stored, if desired. In this example, up to four images can be added to a workspace for review. Other configurations are possible. See FIG. 37 described below.

An example method for entering advanced settings such settings as volume, time, date, etc. can be accessed upon entering of a password or access code by the clinician. In one method, an access code is needed to change certain settings, and an advanced settings code is needed to change other advance settings. Other configurations are possible.

In an example method for selecting network connectivity, a plurality of WiFi networks are shown, and the clinician can select one for connection thereto. Upon successful connection, the system 600, 605 can communicate with the cloud.

In an example method for image inspection, once an image is selected, it is displayed to the clinician for review. The user can discard the image or move forward with image capture, as desired.

In an example method for discard of an image, a number of discards is tallied. If over a threshold amount (e.g., 2, 3, 5, 10, etc.), a warning can be given that further image acquisition could be uncomfortable for the patient.

In an example method for returning to a home screen, a home button is provided on each interface. When selected, the home screen interface is shown, allowing the clinician to make initial selections like patient list, examination, review, and settings.

If the home button is selected when there are unsaved images, the clinician is first prompted to save or discard the images before returning to the home screen. In this example, the method includes displaying a prompt with a save button to allow the clinician to save the images. Once saved, the home screen is displayed.

In an example method for docking the system 600, 605, the system 600, 605 is placed in a charging cradle. Upon connection with the cradle, an icon indicating a USB connection is displayed on the dock and/or the system 600, 605. If acquisition is complete, the screen is turned off and sleep is instituted without a certain time period (e.g., one minute). If acquisition is not complete, the clinician is prompted to complete acquisition.

In an example method for assuring that all items for an examination have been received or overridden, if items are missing, the save button is disabled. However, the clinician can select the override button and, in certain contexts, allow for saving of data without all required items (e.g., a skipped indication) being present.

In an example method for updating software on the system 600, 605, software can be uploaded from a removable storage medium (e.g., SD card) during boot to update the software on the system 600, 605. In other examples, software can be downloaded, such as from the cloud.

In another example for waking the system 600, 605 from sleep, the user can press the home button to wake the system. Upon wake, a login screen can be presented, requiring the clinician to enter an access code to use the system 600, 605.

In some examples a method is provided for training purposes. In this embodiment, training information can be accessed from the home screen. The training can provide user interface information that trains the user on the configuration and use of the system 600, 605.

Figure 34:
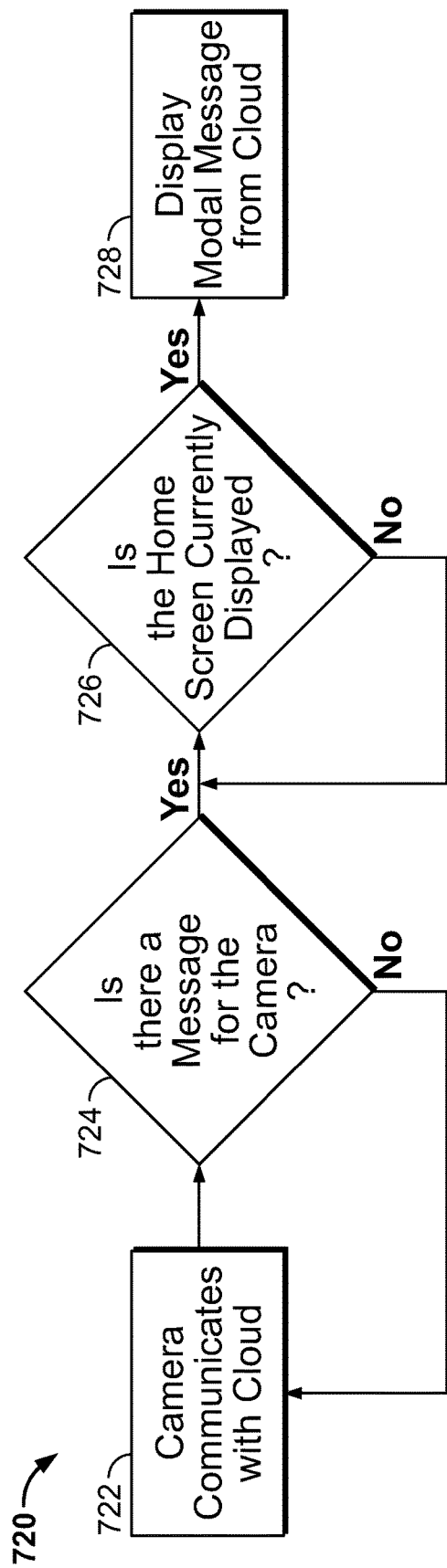
FIG. 34 is an example method for sending messages to an apparatus for recording and viewing an image of a patient's fundus in the system of FIG. 33.
Figure 35:
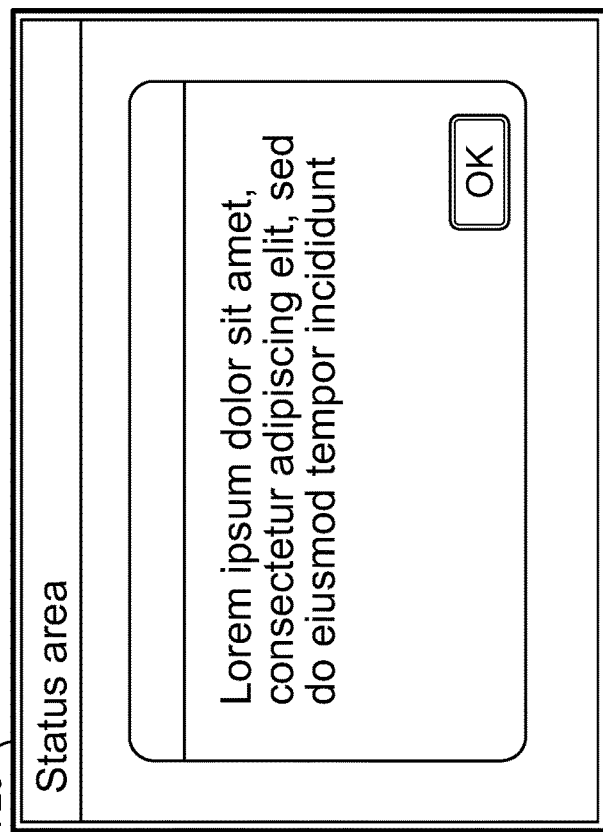
FIG. 35 is an example message from the method of FIG. 34.

Referring now to FIGS. 34-35, in some example, the system 700 allows for messaging to the clinician who is capturing the fundus images. For example, the cloud system 704 and/or the clinicians working as part of the over read service 712 can directly message the clinician capturing the fundus images regarding such as issues as image quality.

For example, FIG. 34 shows a method 720 that allows the over read service to message the clinician obtaining the fundus images with the device 702. Such messages can be addressed using various methods, such as device name, device ID (serial number/MAC address), device IP address, etc. In this example, one or more messages are provided by the over read service 712 to the cloud system 704. At operation 722, the device 702 connects to the cloud system 704 using a known protocol, such as TCP/IP. At operation 724, a determination is made regarding whether or not a message is waiting for the device 702. If so, control is passed to operation 726, and a determination is made regarding whether or not a particular graphical user interface (e.g., a home screen) is being displayed on the device 702. If so, control is passed to operation 728, and a message is presented to the clinician on the graphical user interface.

At FIG. 35, one example of such a message 729 is shown. The message 729 can be displayed so as to get the attention of the clinician operating the device 702, such as by popping up, color, sound, etc. The message 729 can provide information regarding the quality of the images that have been captured by the device 702. For example, if the images are not of a sufficient quality for the over read service 712, the over read service 712 can send a message to the device 702. The clinician C can read the message, as well as information about how to remedy the situation (e.g., the message could provide information such as "Clean a certain part of the lens, etc.).

In addition to the messaging between the device 702 and the cloud system 704 described above, the cloud system 704 can be used to store various information associated with the examination of a given patient. For example, as the fundus images are captured, the clinician C can adjust various settings associated with the device 702, such as brightness, focus, etc. Once a desired set of settings is identified for a particular patient, these settings can be stored in the cloud system 704 (e.g., in a database) and/or the EMR 706 and associated with the patient. When the patient returns for a subsequent examination, the device 702 can be configured to automatically access the settings for the device 702 by downloading the settings from the cloud system 704. In this manner, the device 702 can be automatically configured according to those settings for subsequent capture of the patient's fundus images.

Figure 36:
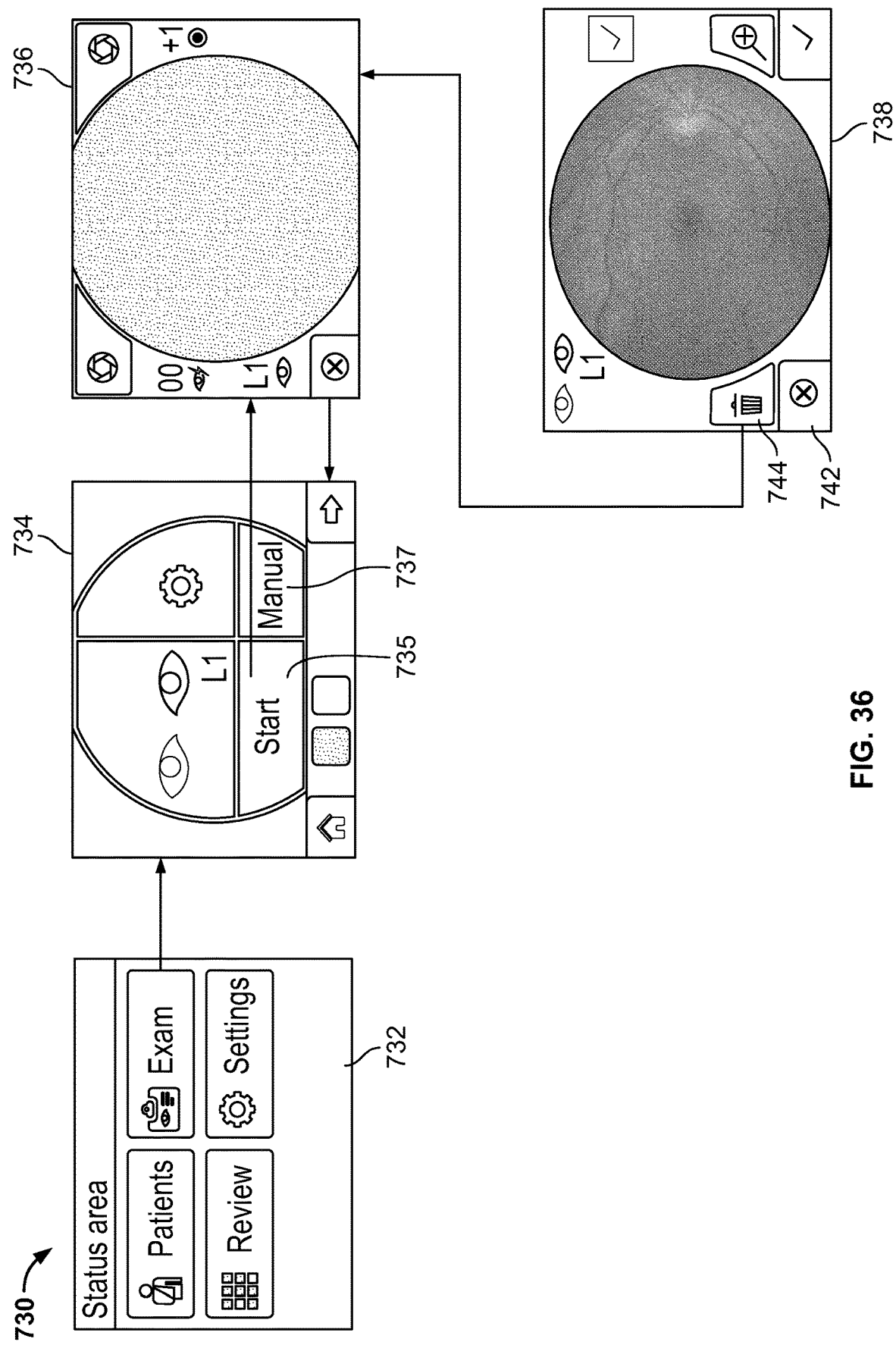
FIG. 36 is an example workflow for automatically capturing fundus images using the system of FIG. 33.

Referring now to FIG. 36, an example workflow 730 for automatically capturing fundus images using the device 702 is shown. The workflow 730 is automatically performed by the device 702 to provide a standardized fundus examination. The workflow 730 includes a selection stage 732, a pre-acquisition stage 734, an acquisition stage 736, and a post-acquisition stage 738.

At the selection stage 732, the clinician C is presented with a menu of options, including an examination icon. The clinician C selects the examination icon to initiate the workflow 730.

Figure 37:
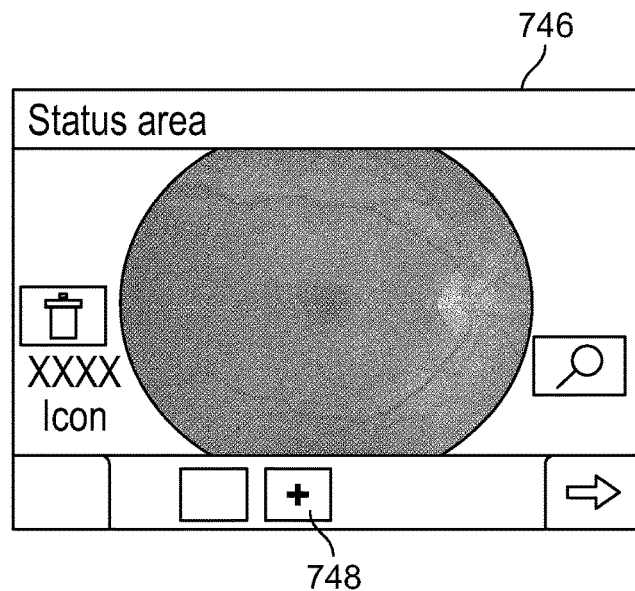
FIG. 37 is an example graphical user interface that allows for images to be added to the system of FIG. 33.
Figure 38:
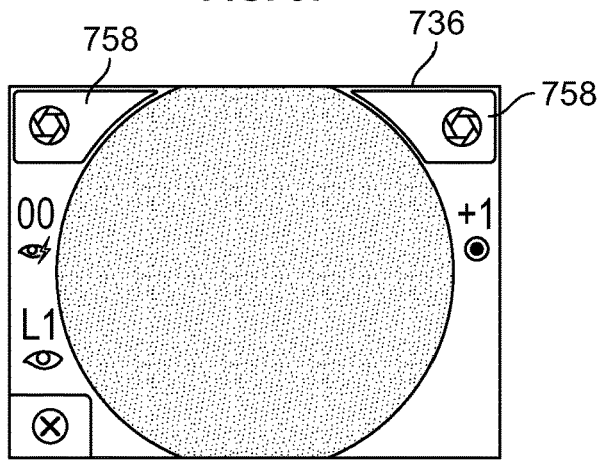
FIG. 38 is an example graphical user interface that allows for the manual capture of images using the system of FIG. 33.

At the pre-acquisition stage 734, the clinician C is presented by the device 702 with options to start the workflow 730 or to perform a manual capture of fundus images (see FIG. 37). The clinician C selects the "Start" button 735 to begin the workflow 730 (or can select the manual capture icon 737 to manually capture images as described further below.

At the acquisition stage 736, the device 702 automatically captures the desired fundus images from the patient P. The image capture can include one or more tones indicating the capture of images, along with automated quality checks on the images. An example of such a process for automating the capture of fundus images is described in U.S. patent application Ser. No. 15/009,988.

Finally, at the post-acquisition stage 738, the clinician C can review the captured images. The clinician C can perform such actions as discarding images and/or adding images, as described further below.

For example, the clinician C can decide to discard one or more of the fundus images. In one example, the clinician C is provided with various options. If one option is selected (e.g., a "Close" icon 742), the device 702 returns to the pre-acquisition stage 734. If another option is selected (e.g., a trash icon 744), the device 702 returns to the acquisition stage 736 to allow for the immediate retake of the fundus image(s). Other configurations are possible.

In another example, clinician C can add images for the patient P. In this example shown in FIG. 37, a user interface includes a control 748 that allows the clinician C to add images by returning the device 702 to the pre-acquisition stage 734. At that point, the device 702 can be used to capture further fundus images that are associated with the patient P.

In addition, other workflows can be performed by the device 702. For example, the workflow 730 can be a default workflow for the device 702, but the device 702 can be configured to perform a modified workflow depending on which over read service 712 is used. For example, a particular over read service 712 may be defined requirements for such parameters as: number of fundus images; type of fundus images (e.g., left, right, macula centered, optic disc centered, etc.); order of capture sequence.

In some examples, the workflow for the device 702 is defined by one or more scripts. The scripts can be downloaded from the cloud system 704 to allow for the modification of the functionality of the device 702. A particular script can be selected by the clinician C to modify the workflow for the device 702. In addition, the device 702 can be programmed to automatically select a script based upon such parameters as clinician C preference, over read service, etc.

In addition to the automated workflow 730, other configurations are possible. For example, as part of the automated capture of fundus images, the clinician C can select to manually capture one or more fundus images. Specifically, during the pre-acquisition stage 734 or the acquisition stage 736, the clinician C can select one of the manual capture icons 737, 758 to have the device 702 capture an image. Other configurations are possible.

Figure 39:
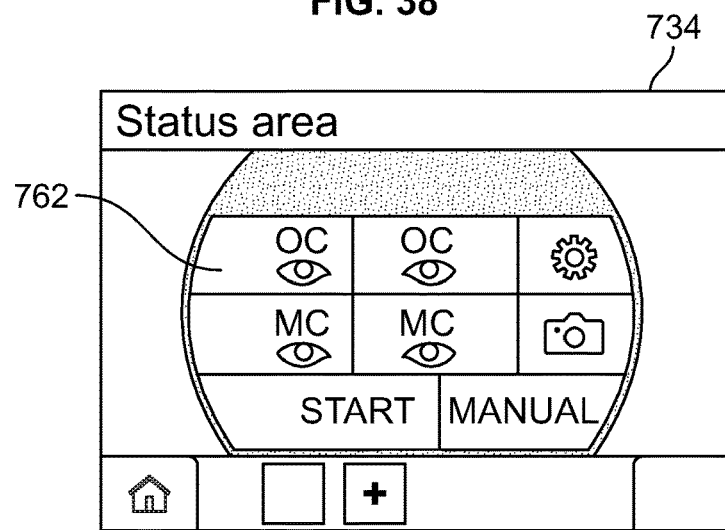
FIG. 39 is an example graphical user interface that allows for pre-selection of an eye position and fixation target using the system of FIG. 33.

Referring now to FIG. 39, in some examples, the pre-acquisition stage 734 allows the user to pre-select an eye position and fixation target before taking fundus image(s). In this example, controls 762 are provided that allow the clinician C to select eye position (e.g., left, right, macula centered, optic disc centered, etc.) before images are either automatically (by selecting "start") and/or manually (by selecting "manual") captured using the device 702.

Figure 40:
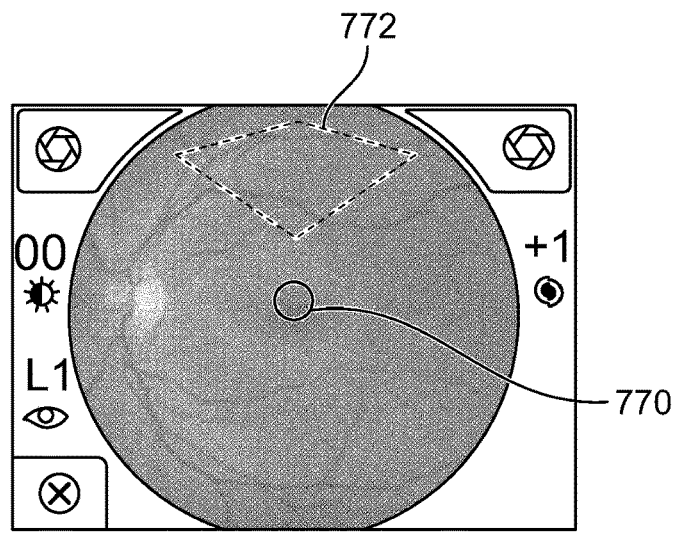
FIG. 40 is an example graphical user interface to assist in assist with aiming during capture of images using the system of FIG. 33.

When manually capturing images, the device 702 is programmed as depicted in FIG. 40 to assist the clinician C with aiming the device 702 for capturing the fundus image(s). In this example, a circular element 770 guides the clinician C with the initial approach of the device 702 to the eye. A diamond element 772 thereupon provides the user with adjustment guidance once the device 702 is in the correct proximity to the patient P's eye. Specifically, when the device 702 is focused in the inner eye, a retina reflection will appear in the view. The clinician C can thereupon use micro adjustments of the barrel of the camera to move the reflection into the diamond element 772. Once in position, the device 702 will automatically trigger a capture of the image.

Figure 41:
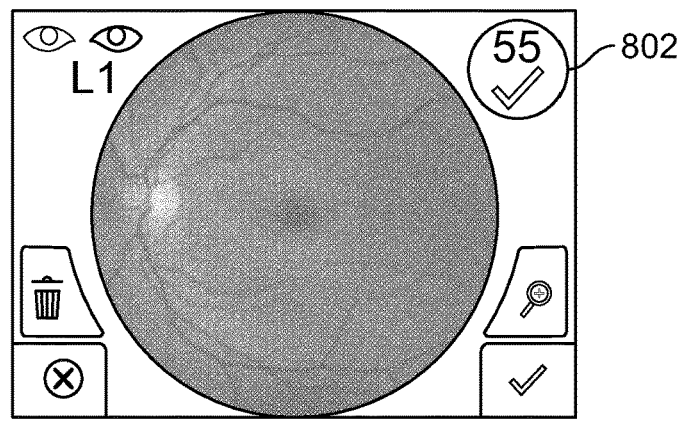
FIG. 41 is an example graphical user interface including an indication of a quality of an image captured using the system of FIG. 33.
Figure 42:
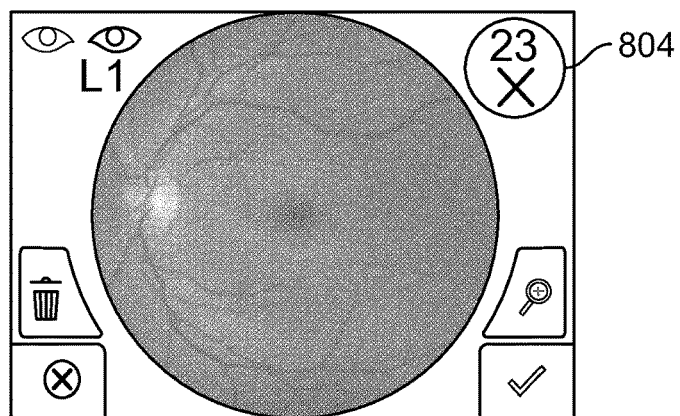
FIG. 42 is another example graphical user interface including an indication of a quality of an image captured using the system of FIG. 33.

Referring now to FIGS. 41-42, the device 702 provides the clinician C with a readily discernable indication of image quality after the image is captured. As shown in FIG. 41, the device 702 provides an indicator 802 that indicates the quality of the captured fundus image. In this example, color (e.g., red is bad, yellow is passable, green is good) is used, along with a signification of quality (e.g., check mark is passable). In addition, the indicator 802 includes a quality score, such as a value ranging from 0 (lowest quality) to 100 (highest quality). In another example of FIG. 42, the red "X" indicates a poor quality image that fails the lowest standards for, for example, the over read service. In such a scenario, the fundus images can be recaptured using the device 702. Other configurations are possible.

Figure 43:
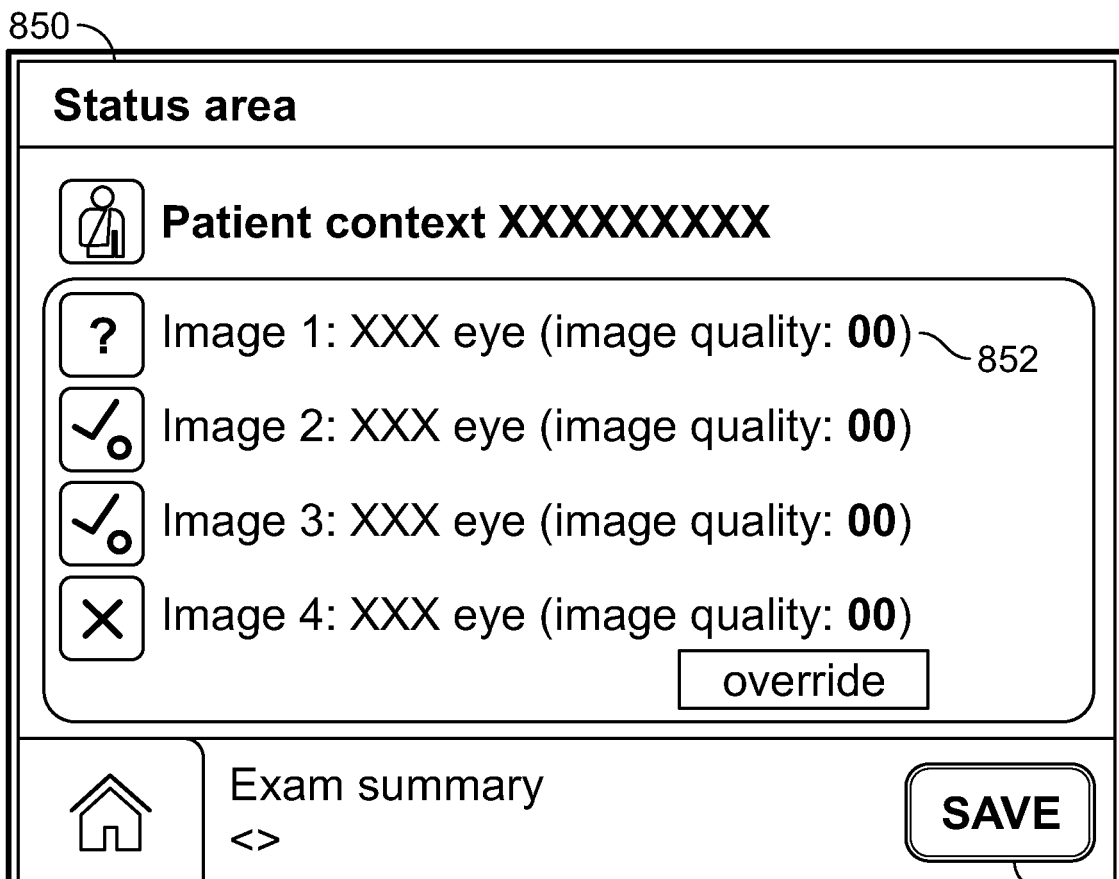
FIG. 43 is an example reporting table listing the images captured using the system of FIG. 33.

Once fundus images have been captures, the device 702 provides a reporting table 850 shown in FIG. 43. This reporting table 850 provides a summary of the images for easy review by the clinician C. In this example, the reporting table 850 includes an entry 852 for each image. This entry 852 provides an indication of the image quality (e.g., using the color, icon, and/or scores described above) and image type (e.g. portion of the image captured). The clinician C can edit contextual information associated with the images, such as the image type. The clinician C can also select one or more of the entries 852 to perform such functions as discard and/or retake certain images. After review is complete, the clinician C can select a save button 854 to save the desired images and/or upload those images to the cloud system 704. Other configurations are possible.

FIGS. 44-52 provide additional embodiments of example systems for recording and viewing an image of a patient's fundus. In these examples, the systems provide for the capture of multiple images of an eye and/or multiple workflows to capture images of an eye.

Figure 44:
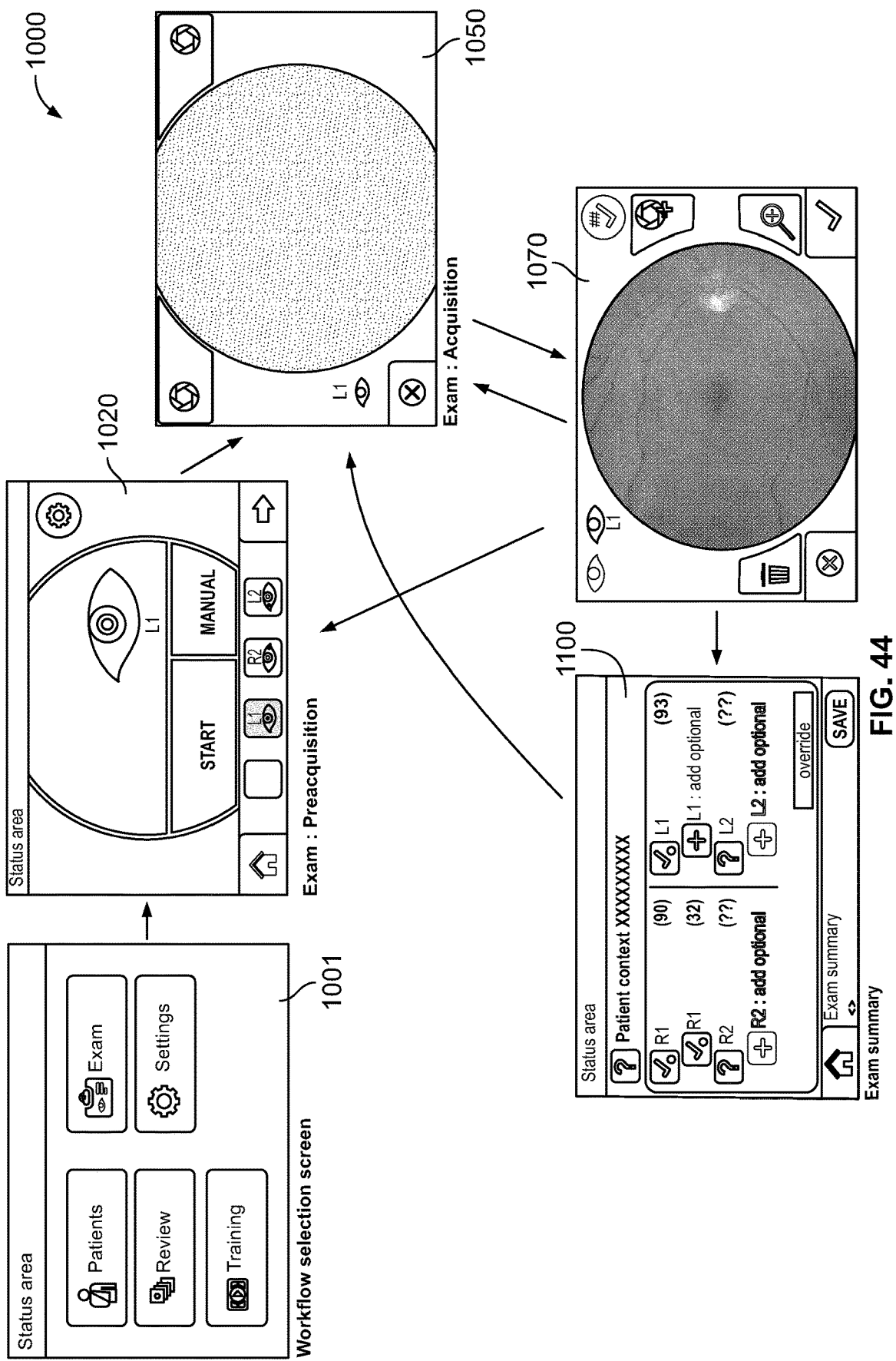
FIG. 44 is an example workflow for capturing fundus images using the system of FIG. 33.

Referring now to FIG. 44, an example workflow 1000 for automatically capturing fundus images using device 702 is shown. The workflow 1000 is performed by device 702 to provide a standardized fundus examination. Workflow 1000 includes a workflow selection interface 1001, a pre-acquisition interface 1020, an acquisition interface 1050, a post-acquisition interface 1070, and an exam summary interface 1100. Other embodiments can include more or fewer interfaces (stages).

At workflow selection stage 1000, the clinician C is provided with various navigational controls. More specifics about workflow selection interface 1001 are described below with reference to FIG. 45. If clinician C selects exam control 1002, device 702 proceeds to initiate a workflow for acquiring fundus images of a patient.

After selecting exam control 1002, device 702 provides pre-acquisition interface 1020 on the display. Generally, pre-acquisition interface 1020 enables the clinician C to indicate: which eye will be imaged, a focus input for the given eye, and whether to proceed automatically or in a manual mode. Other navigational controls, and additional functionality, provided on pre-acquisition interface 1020 are described below in more detail with reference to FIG. 46. When clinician C selects either the start or manual control, device 702 proceeds to the acquisition stage 1050.

At the acquisition stage 1050, device 702 captures a fundus image. As mentioned above, the image capturing may be performed automatically, or if clinician C selected manual control in pre-acquisition stage 1020, clinician C uses controls on acquisition interface 1050 to initiate image capture. Additional details about acquisition interface 1050 are provided with reference to FIG. 47 below.

After device 702 acquires a fundus image, the display of device 702 shows post-acquisition interface 1070. At post-acquisition stage 1070, the clinician C can review the captured image. Additionally, interface 1070 provides an indication of the image quality, the opportunity to delete the captured image, and/or controls to initiate additional image acquisition sequences of the given eye. If the additional image sequence control is selected, device 702 proceeds to capture a second image of the given eye at the previously selected image point focus. In those instances, workflow returns to acquisition stage 1050. Additional details regarding post-acquisition interface 1070 are provided with reference to FIG. 48 below.

After displaying post-acquisition stage 1070, device 702 then displays exam summary interface 1100. Exam summary interface 1100 generally depicts information summarizing which eyes have images captured therefor and at what image point focus. Advantageously, exam summary interface 1100 also provides controls for additional image capture sequence initiation for a particular eye at a particular image point focus. Additional details regarding exam summary interface 1100 are described below with reference to FIG. 49.

Figure 45:
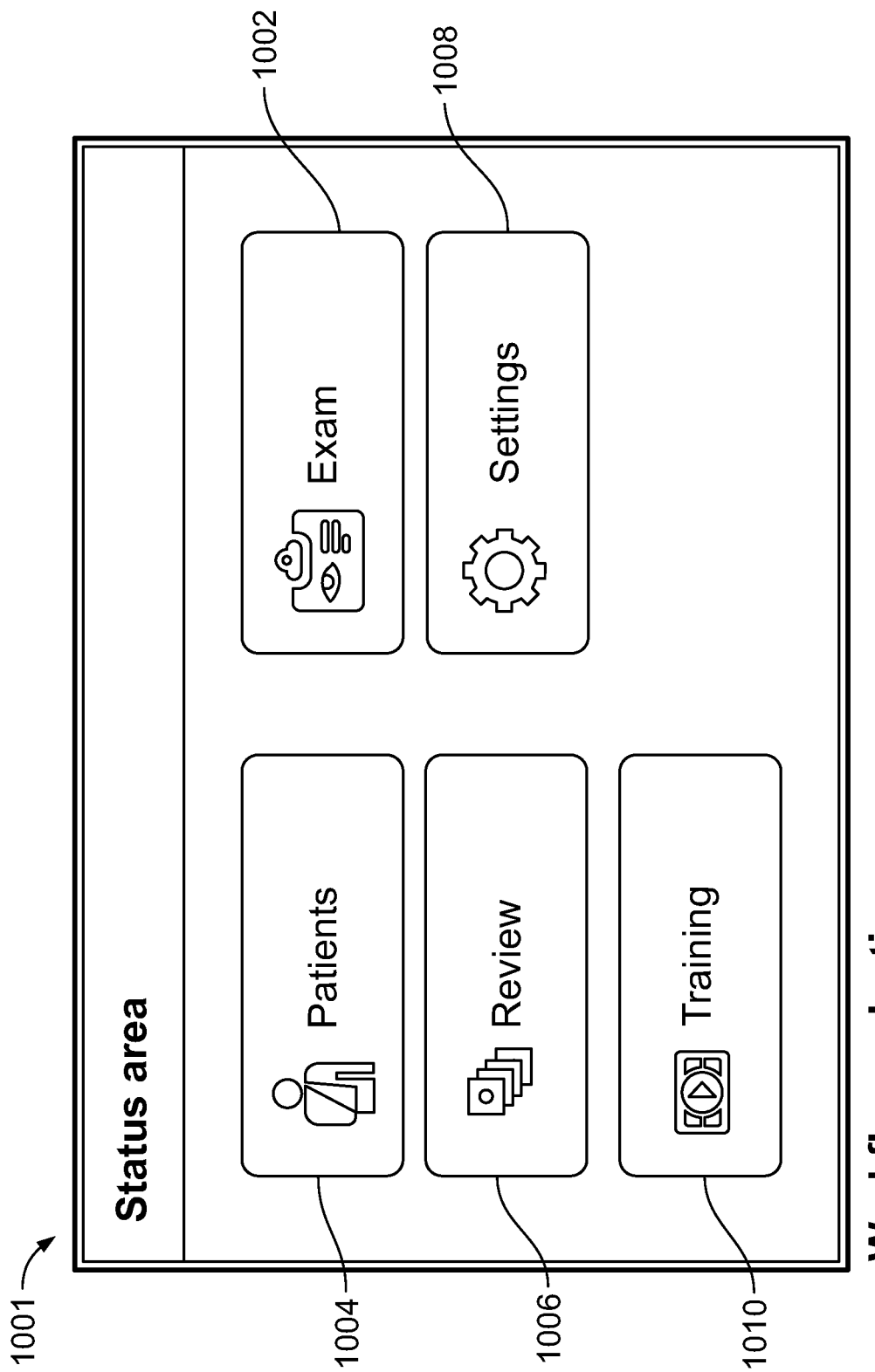
FIG. 45 is an example workflow selection interface shown in the workflow of FIG. 44.

Referring to FIG. 45, workflow selection interface 1001 includes various controls enabling clinician C to navigate about various workflows provided by device 702. As shown, workflow selection interface 1001 includes a patient control 1004, an exam control 1002, a review control 1006, settings control 1008, and training control 1010. Other embodiments can include more or fewer controls.

Exam control 1002 initiates image capture workflow 1000 described above with reference to FIG. 44, and discussed below with reference to FIGS. 50-52. Patients control 1004 enables clinician C to add or edit patient data. Review control 1006 enables clinician C to review previously captured images during a particular session for a particular patient, or for the particular clinician C. Settings control 1008 provides clinician C the ability to modify various device settings 702, such as frame capture rate, display brightness, Wi-Fi network connectivity, and the like. Training control 1010 enables clinician C to review one or more training documents such as videos and/or instructional pamphlets.

Figure 46:
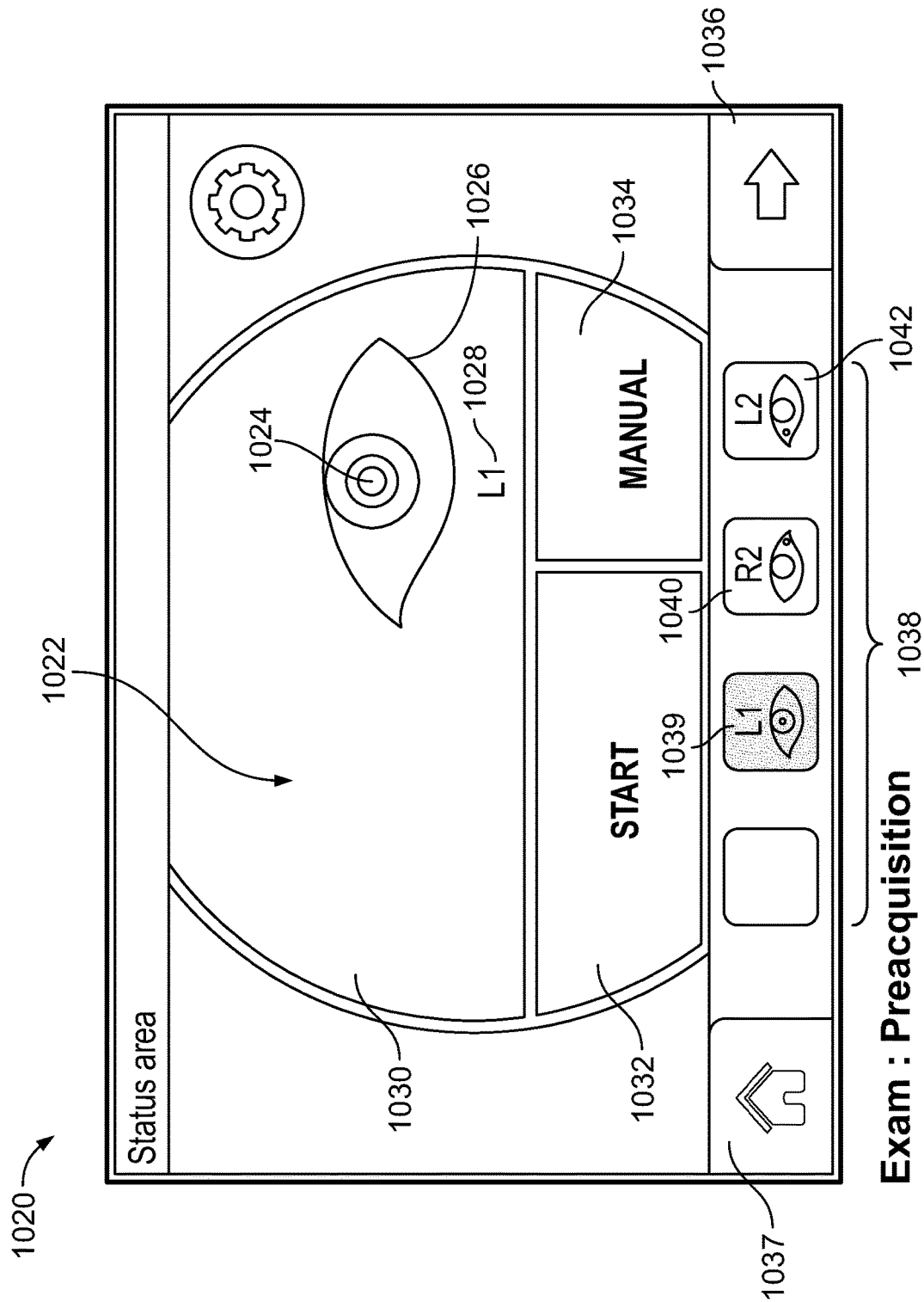
FIG. 46 is an example pre-acquisition interface shown in the workflow of FIG. 44.

Referring now to FIG. 46, pre-acquisition interface 1020 provides controls for clinician C to select which eye to be imaged and at what image point focus. Image point focus is a portion of the fundus that device 702 will focus on during image capture. In the embodiment shown, there are two image point foci that are associated with different prescriptive workflows: optic-disc centered and macula-centered. These are described further below with reference to FIGS. 53-58.

Icons 1039 and 1042 provide an indication of the image point focus. Control 1039 initiates image capture sequence of a patient's left eye that is macula-centered. Control 1042 initiates image capture that has an optic disc-centered focus for the left eye. Display portion 1022 includes a darkened indicator dot 1024 that device 702 will image the left eye in optic disc-centered focus. The eye that will not be imaged is shown grayed out, as in icon 1030.

In display portion 1022, the left eye 1026 is shown and a dot 1024 is shown indicating the focus point for the image. In various embodiments, dot 1024 can be red, green, or other colors. Display portion 1022 also includes an indication 1028 of which eye and which prescriptive workflow will be used for capture. In the interface shown, FIG. 46, this will be the first image at the particular image point focus for the left eye, as indicated L1 in portion 1028. See FIGS. 53-58 for additional details on the positioning of the dot 1024 according to indicate the focal point for optional multiple prescriptive workflows.

The acquisition interface 1020 also includes start control 1032 and manual start control 1034. Start control 1032 initiates an automatic imaging sequence where device 702 does not require clinician C to initiate the actual image capture. In contrast, manual control 1034 initiates an imaging acquisition sequence that requires clinician C to initiate image capture.

Pre-acquisition interface 1020 also includes summary section 1038. Summary section 1038 provides clinician C with a summary of which eyes have been imaged and at what image point focus. Adjacent to summary 1038 are navigational buttons 1036 and 1037. Control 1036 causes device 702 to bring up exam summary interface 1100. Control 1037 causes device 702 to return to a home page. In some instances, the home page can be work flow selection interface 1001.

Figure 47:
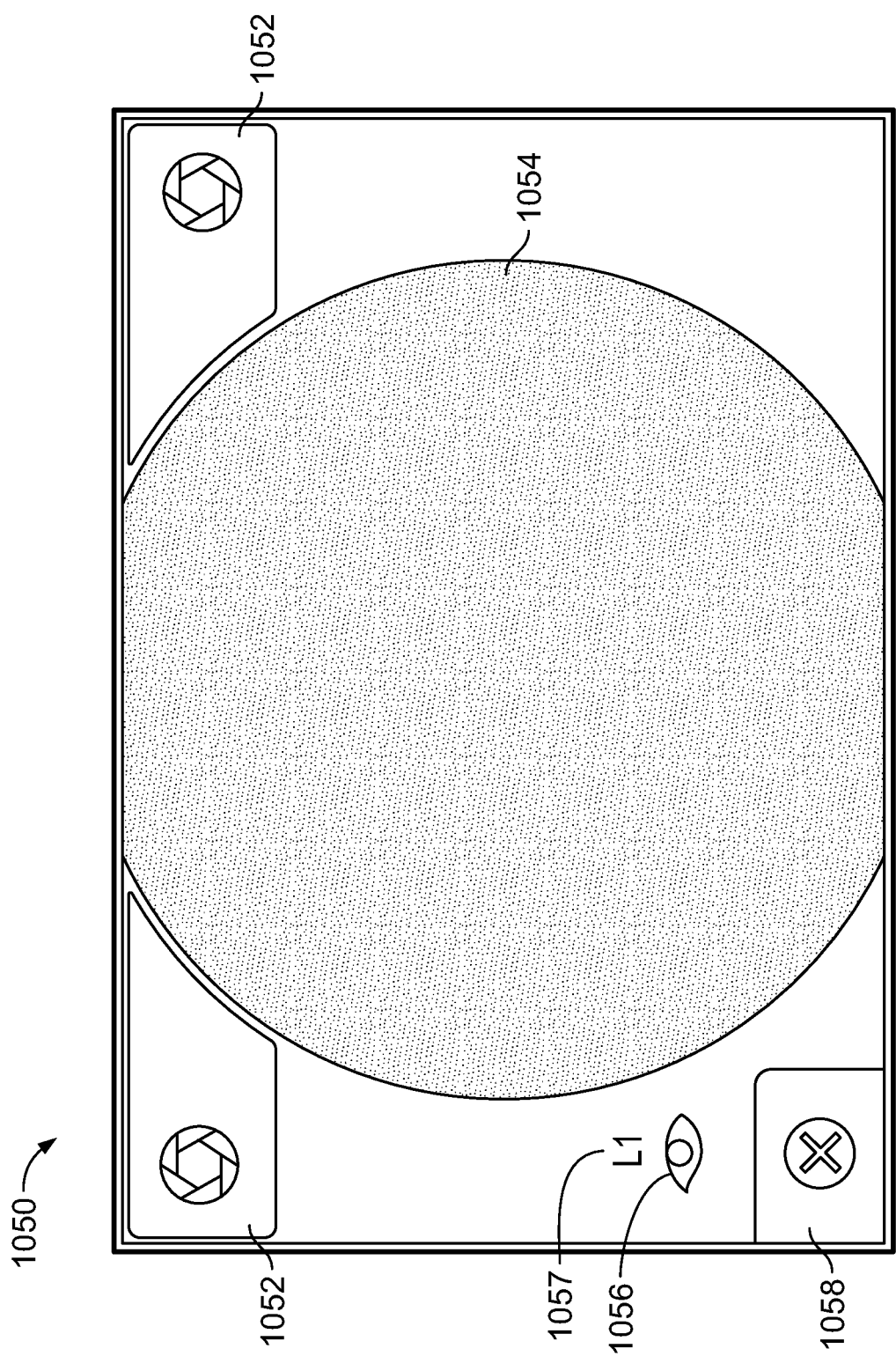
FIG. 47 is an example acquisition interface shown in the workflow of FIG. 44.

Referring now to FIG. 47, the acquisition interface 1050 is shown. Acquisition interface 1050 includes image capture controls 1052. In the embodiment shown, both the upper left and upper right corners of interface 1050 include controls 1052. In most instances, controls 1052 are not provided in an automatic image capture mode.

Acquisition interface 1050 also includes preview portion 1054. Preview portion 1054 enables clinician C to preview what the image sensor array might capture during an image capture. Because there is typically some time delay between selection of control 1052 and actual image capture by the image sensor array, what appears on the previous screen may or may not be the image captured by device 702.

Acquisition interface 1050 also includes indicators 1056 and 1057, which show the image point focus and eye and image capture number for the given eye, respectively. Acquisition interface 1050 also includes control 1058. Control 1058 causes the workflow to return to pre-acquisition interface 1020.

Figure 48:
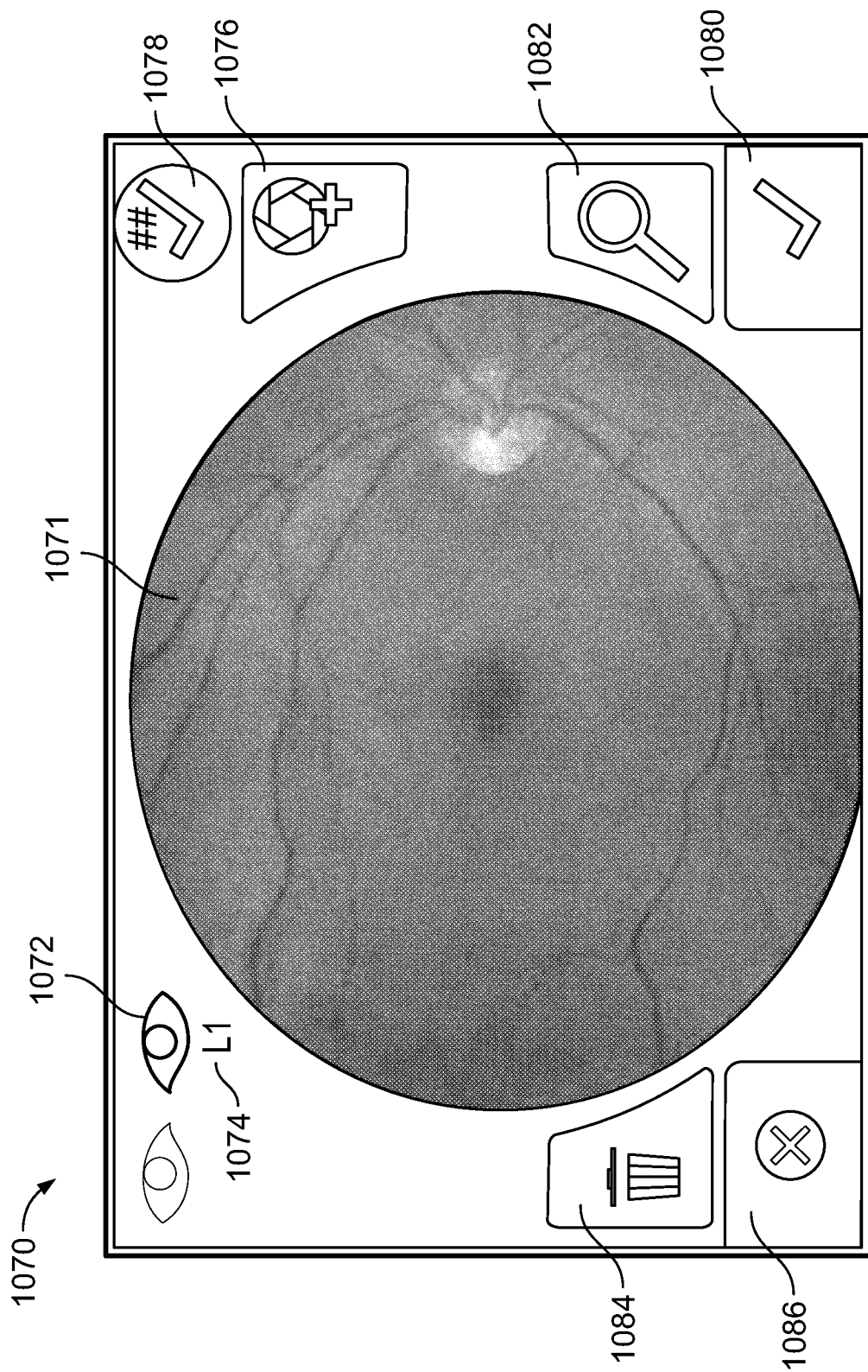
FIG. 48 is an example post-acquisition interface shown in the workflow of FIG. 44.

Referring now to FIG. 48, post-acquisition interface 1070 is provided. Post-acquisition interface 1070 includes image preview 1071, which is a reproduction of the image captured during manual or automatic imaging as provided by device 702 in acquisition sequence 1050. Post-acquisition interface 1070 also includes indicator icons 1072 and 1074, which indicate the eye imaged, the image point focus and number images that have been captured for that particular eye.

Post-acquisition interface 1070 includes additional image capture control 1076. Generally, the example additional image capture control 1076 is a visual indicator that juxtapositions an iris, or shutter, icon and a "+", or add, icon. The additional image capture control 1076 is a control for adding an image.

Specifically, the additional image capture control 1076 causes device 702 to capture another image of a given eye at the image point focus, without requiring any further input from the user (e.g., to select or provide any imaging settings). Selection of additional image capture control 1076 causes device 702 to display acquisition interface 1050 so that an additional image of the eye at the selected focal point can be taken.

After device 702 acquires the fundus image, device 702 analyzes the image for its quality and provides an image quality score on post-acquisition interface 1070. This is indicator 1078. Methods for determining image quality, and other specifics relating thereto, are discussed in more detail above.

Post-acquisition interface 1070 can include various other controls. For example, control 1082 initiates an image inspection workflow, where clinician C can zoom in on various portions of the captured image, navigate about the image, and/or view various parameters relating to the captured image. Control 1080 causes the workflow to proceed to display exam summary interface 1100. Control 1084 discards the captured image and causes the workflow to return to acquisition interface 1050. Control 1086 discards the captured image and causes the workflow to return to pre-acquisition interface 1020.

Figure 49:
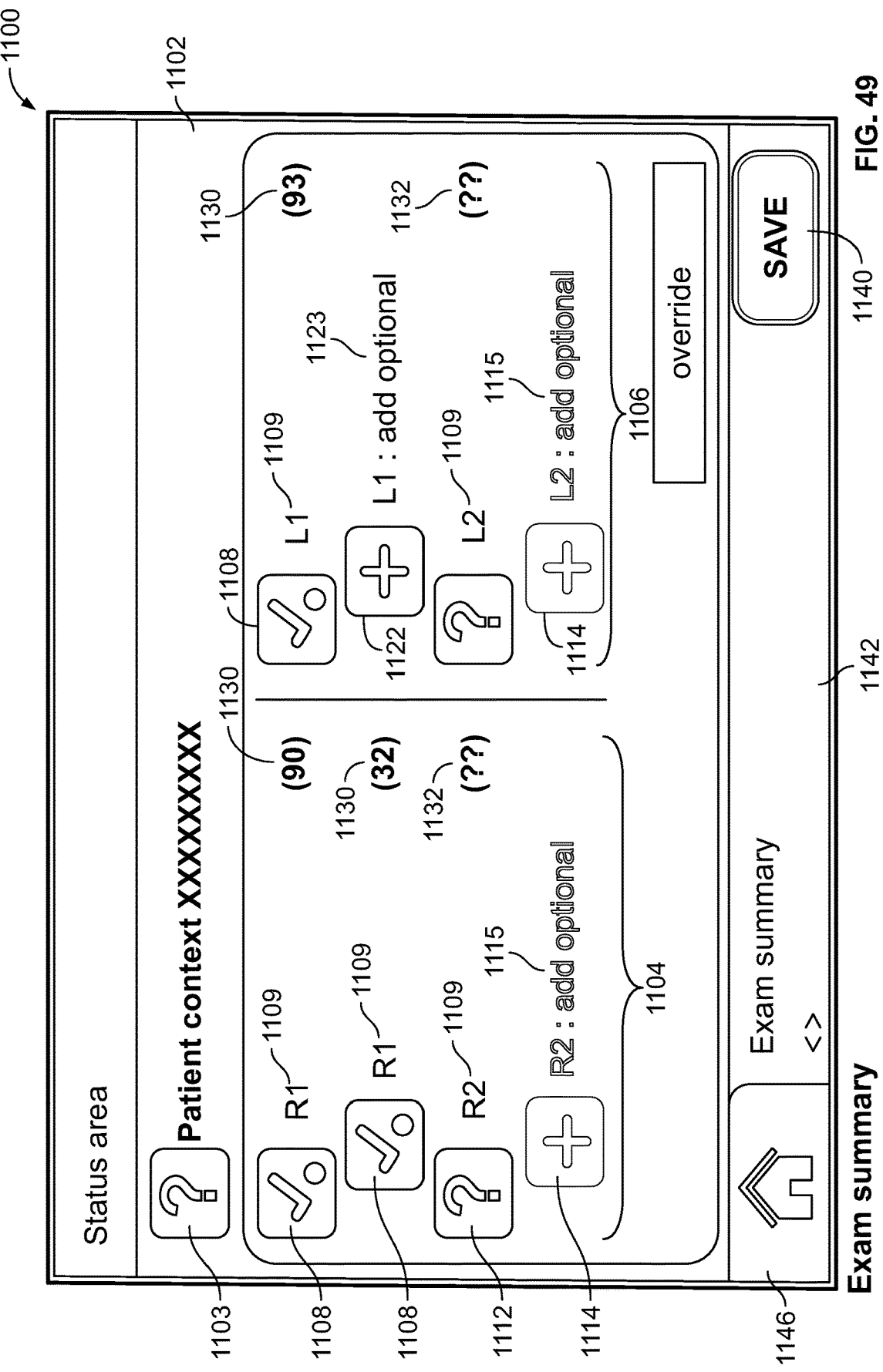
FIG. 49 is an example exam summary interface shown in the workflow of FIG. 44.

Referring now to FIG. 49, exam summary interface 1100 is shown. Exam summary interface 1100 includes patient context pane 1102, which includes icon 1103. Patient context pane 1102 indicates whether there is any patient context for the particular patient whose fundus has just been imaged. Patient context can include patient ID, patient name, and the like. Icon 1103 indicates whether patient context has been acquired. In the embodiment shown, icon 1103 indicates that no patient context has yet been provided and/or acquired.

Exam summary interface 1100 also includes right eye summary pane 1104 and left eye summary pane 1106. Summary panes 1104 and 1106 provide indicators about how many images have been captured for each eye, at what image focus points, and additionally provide controls for initiating additional images to be captured of a particular eye at a given image point focus. Summary regions 1104 and 1106 also include image quality scores 1130. Icons 1112 indicate that no images having been captured that meet the particular number (first or second image), eye, and image point focus. Accordingly, if no image has been captured, there is no image quality, as indicated by question marks 1132.

Icon 1108 provides information about captured images. Icon 1108 indicates whether an image has been captured for that particular eye at the particular image focus point. The second image captured for a given eye at an image point focus is indented from the first image captured for that eye and image point focus. Additionally, icon 1108 can include a graphical representation of the image quality score, such as by providing a green dot, a yellow dot or a red dot. In some embodiments, when the image quality score is below a predetermined threshold, not only is the dot red, but the checkmark in icon 1108 can be shaded lighter than for image quality scores higher than that pre-determined threshold. Icon 1112 indicates that no image has been captured for the particular eye at the given image point focus.

Icon 1109 indicates the eye and optionally the image point focus of the image. Specifically, the "R" indicates images for the right eye, and the "L" indicates images for the left eye.

The image point focus is indicated by the numeral following the R or L. Specifically, the numeral "1" indicates that a first image point focus according to a first prescriptive workflow was used to capture the noted image(s), and the number "2" indicates that a second image point focus according to a second prescriptive workflow was used to capture the noted image(s). For example, "R1" indicates that a right eye image was captured using a first prescriptive workflow dictating a first image point focus. Additional details about the various prescriptive workflows are provided with reference to FIGS. 53-58 described below.

Within the summary interface 1100, the user is provided a set of enhanced user controls (e.g., icon 1122) by which to capture, in an intuitive manner, an optional, secondary image for each eye and imaging point of focus. The visual indicator and control, which indicates "add optional", allows the user to intuitively add one optional image for each eye and imaging point, in addition to one previously captured image for that eye and imaging point. These controls are displayed in a parent-child subordinate relationship with the eye and imaging point that each is associated with, with the optional, secondary image indented below the previously captured image.

For example, the icon 1122 enables the initiation of an additional image capture sequence without requesting any additional parameters for the given image capturing, at the particular eye and image point focus. In other words, by selecting icon 1122 from the summary interface 1100, the user can directly access the prescriptive workflow for capturing a second image (e.g., acquisition interface 1050). This would allow for the addition of an image for the left eye according to the first prescriptive workflow.

Text 1123 provides a summary of this capability. Icon 1114 is shown grayed out because the functionality to add an additional image, at the given image point focus for the given eye, is not necessary because an original image has not yet been captured for that particular eye at that given image point focus. Upon capturing a first image, icon 1114 and text 1115 will become operative controls in interface 1100.

Exam summary interface 1100 also includes controls 1140, 1142, and 1146. Save control 1140 enables clinician C to save the captured images locally and/or on a cloud based server. For instance, save control 1140 can initiate saving of the captured images in the patient's electronic medical record. Exam summary 1142 provides space for clinician C to make any notes about a particular fundus exam. Control 1146 initiates the home screen workflow, as shown in FIG. 45.

Figure 50:
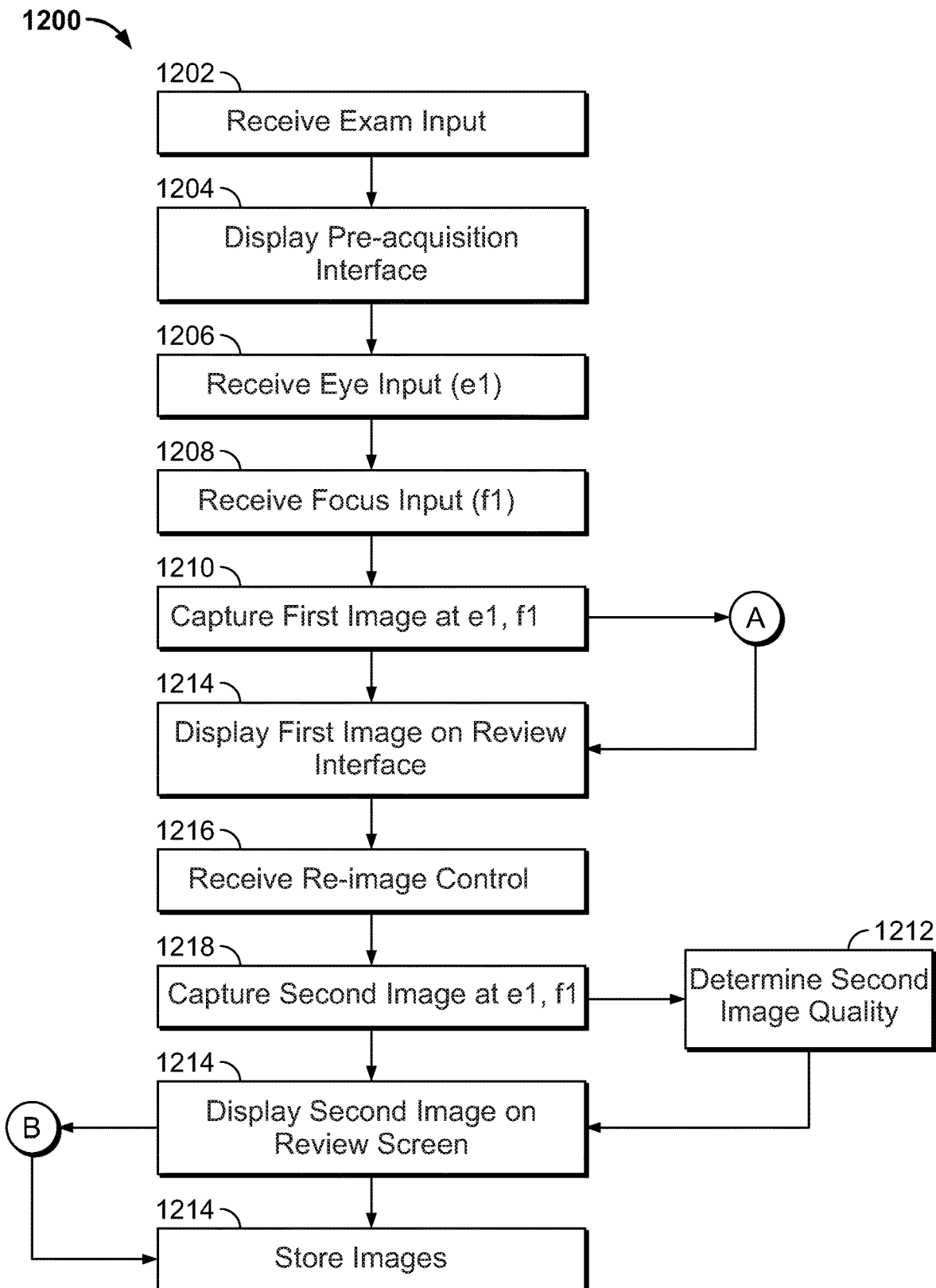
FIG. 50 is an example method of capturing fundus images using the workflow of FIG. 44.
Figure 51:
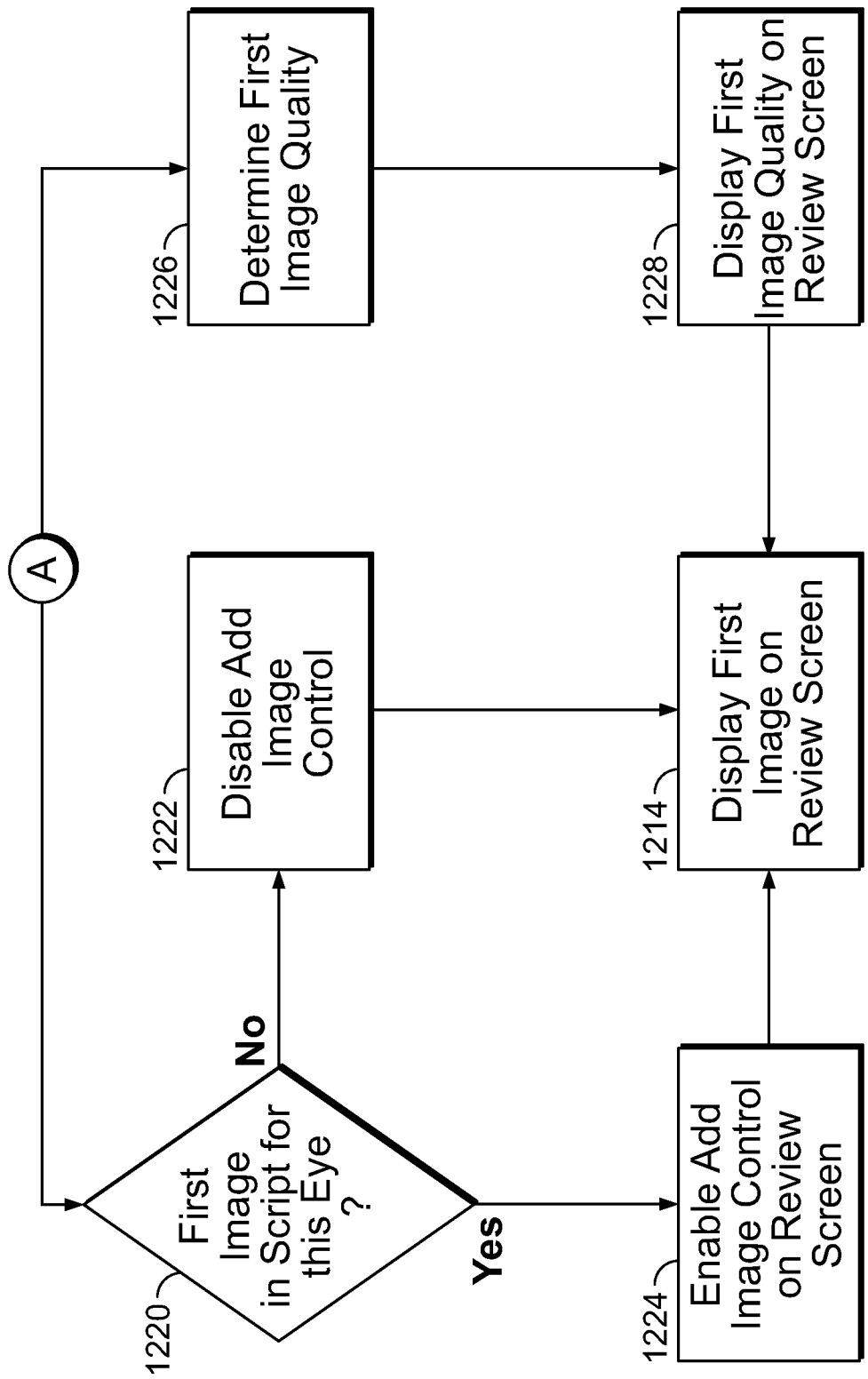
FIG. 51 shows additional operations of the method shown in FIG. 50.
Figure 52:
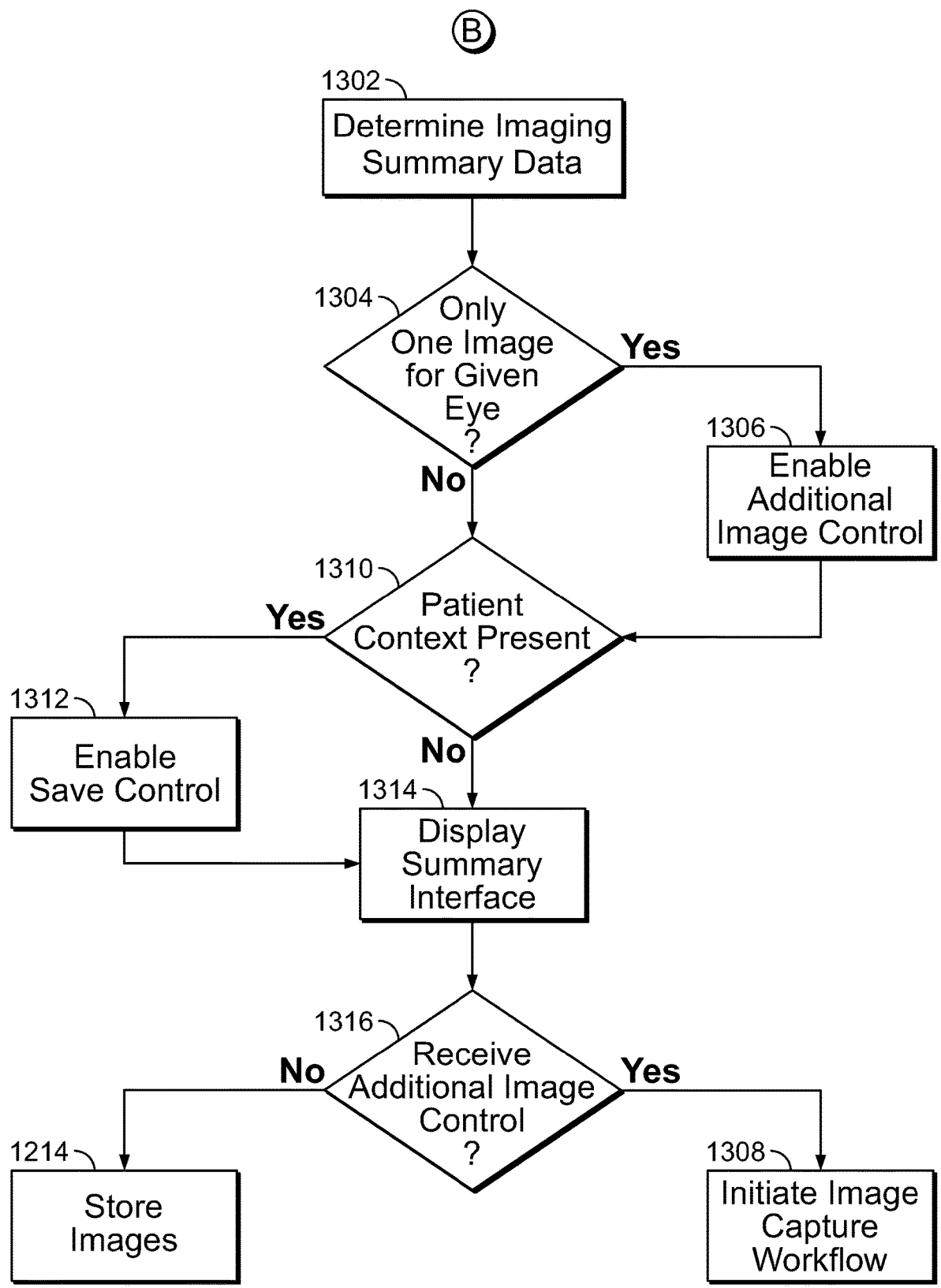
FIG. 52 shows additional operations of the method shown in FIG. 50.

FIGS. 50-52 provide an example method for imaging a fundus of a patient 1200. Example method 1200 parallels, essentially, workflow 1000 described above. Typically, clinician C interacts with device 702 during method 1200. Device 702 performs the steps for operations of example method 1200. Other embodiments of method 1200 can include more or fewer operations.

Example method 1200 begins by receiving exam input (operation 1202). Receiving exam input (operation 1202) includes receiving selection of a control provided on an interface. The control initiates the start of a fundus imaging workflow. As noted above, other controls in addition to exam initiation control can be provided on the initial workflow selection interface.

Next, a pre-acquisition interface is displayed (operation 1204). The pre-acquisition interface includes various controls enabling clinician C to select either the left or the right eye of the patient to image. The pre-acquisition interface can also include controls enabling the clinician to identify a particular image point focus of a portion of the given eye. Additionally, the pre-acquisition interface can display a summary of which images have already been captured and at what image point foci.

Next, device 702 receives eye input (e1) (operation 1206) and receives focus input (f1) (operation 1208). In some instances, eye input and focus input (operations 1206 and 1208) are received simultaneously. For example, a given control on the pre-acquisition interface initiates image capture of the left eye macula-centered. Receiving the eye input (operation 1206) includes receiving a signal regarding which eye is going to be imaged and, in some instances, whether it is the first or the second image captured for that eye. Receiving the focus input (operation 1208) indicates whether the image will be optic disc-focused or macula-focused.

Upon receiving the eye input and focus input (operations 1206 and 1208), and optionally upon receiving selection of a start image capture control (not shown in method 1200), device 702 captures an image at the selected eye input and focus point (e1, f1) (operation 1210). Optionally, example method 1200 continues to display the captured image on a review screen (operation 1214). Example method 1200 can optionally proceed to one or more of the operations shown in FIG. 51.

After capturing the first image at the image point focus for the given eye (operation 1210), determination 1220 and operation 1226 can proceed in parallel or in series. Determination 1220 determines whether this is the first image in the script for the particular eye. If it is not the first image for this eye at the given image point focus, then the add image control is disabled in the review screen (operation 1222). Alternatively, if it is the first image in the script for the given eye at the image point focus, then the add image control on the review screen is enabled (operation 1224).

Additionally, after capturing the image (operation 1210), the image quality of the first image is determined (operation 1226). Example processes and considerations for determining image quality are discussed in more detail above. After determining the first image quality (operation 1226), then the first image quality is displayed on the review screen (operation 1228).

After the image is captured and various attributes are analyzed, the image is displayed on a review screen (operation 1214). An example review screen is shown in FIG. 48 and described in more detail above. If clinician C does not want to capture any more images of a patient's fundus, then a control can be selected to display exam summary 1100, described above.

In some instances, clinician C may want to acquire a second image of the given eye at the image point focus. The next operation in example method 1200 is to receive a re-image control (operation 1216). Notably, re-image control 1076 is provided on the review interface 1070 without leaving the image capture workflow 1000 or the review interface.

Upon receiving selection of the reimage control, the method 1200 proceeds to capture a second image at e1, f1 (operation 1218). The second image captured during operation 1218 is captured at the same image point focus, with the same eye as the first image, and without requiring any additional input from clinician C. Optionally, the image quality of the second captured image is determined (operation 1212).

After capturing the second image at e1, f1 (, the second image is displayed on a review screen (operation 1214). Because this will be the second image for the given eye at the image point focus, the reimage control will be disabled on the review screen.

Upon receiving selection of a proceed control, imaging summary data are determined (operation 1302). Referring to FIG. 52, determining imaging summary data (operation 1302) includes compiling some or all of the data shown in exam summary interface 1100 in FIG. 49 above.

Next, determination 1304 evaluates whether the one image has been captured for the given eye. If only one image has been captured for the given eye, then an additional image control for the summary interface is enabled (operation 1306). If two images have been captured for the given eye at the image point focus, then determination 1310 analyzes whether the patient's context is present. If patient context is present, then save control on the summary interface is enabled (operation 1312). After both determinations 1304 and 1310, the summary interface is provided on the device (operation 1314).

In some instances clinician C may want to capture a second image of a given eye at a given image point focus, particularly if the image quality score is poor, at which point example method 1200 can include receiving an additional image (operation 1316). As mentioned above with respect to FIG. 49, additional image controls can be provided on exam summary interface 1100. Receiving the selection of additional image controls (operation 1316) initiates image capture workflow (operation 1308). Image capture workflow (operation 1308) has been described above with reference to FIGS. 44 through 51. Then the images can be stored (operation 1214) either locally or on a server, which can include an electronic medical record server.

Some or all operations of example method 1200 can repeat for a different eye and/or different image point focus. For example, after completing example method 1200 to capture two images of a patient's left eye optic disc-centered, the operations of example method 1200 repeat to capture one or two images of the patient's right eye optic disc-centered. In the depicted examples, the workflow proceeds to capture images according to the following order: R1, L1, R2, and L2. Although, in other examples, the user could skip certain images and/or modify the workflows to a different desired order.

Referring now to FIGS. 53-58, in some options, multiple prescriptive workflows are provided. Each prescriptive workflow can include a different focal point for the captured image(s). In this embodiment, camera aim indicator icons are provided to communicate to the user where to place the camera, as well as communicating the number of expected required images and/or unique imaging location for each prescribed image. The enhanced camera aim indicator icons can provide, prior to the acquisition process begins, visual representations of left and right eyes, combined with a dot (e.g., colored) to visually indicate, in an intuitive manner, the unique imaging location to be captured for a prescribed image and eye in the digital retinal exam workflow.

Figure 53:
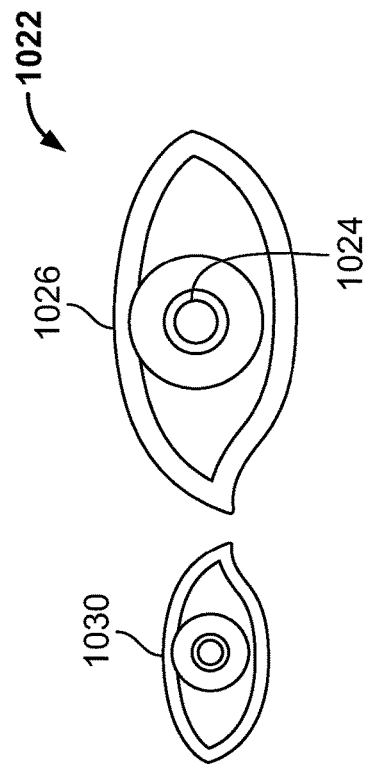
FIG. 53 shows example icons from the display portion of the pre-acquisition interface shown in FIG. 46.
Figure 54:
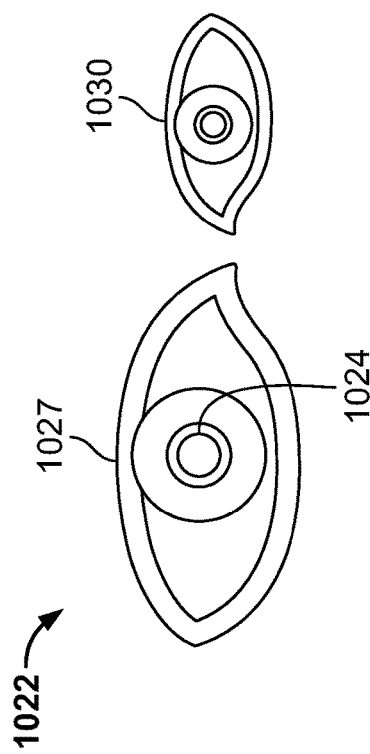
FIG. 54 shows another embodiment of the example icons from the display portion of the pre-acquisition interface shown in FIG. 46.

In this example, FIGS. 53-54 illustrate pre-acquisition interface 1020 (see FIG. 46) that allows for the capture of image of the left eye 1026 and right eye 1027 according to a first prescriptive workflow. This first prescriptive workflow dictates the dot 1024 that device 702 will image the left eye in macula-centered focus. This helps the user understand how the device 702 is focusing each image.

Figure 55:
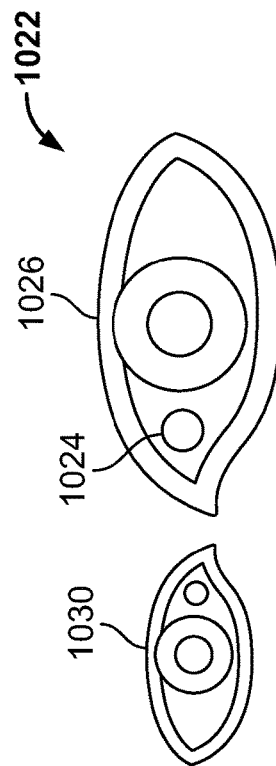
FIG. 55 shows another embodiment of the example icons from the display portion of the pre-acquisition interface shown in FIG. 46.
Figure 57:
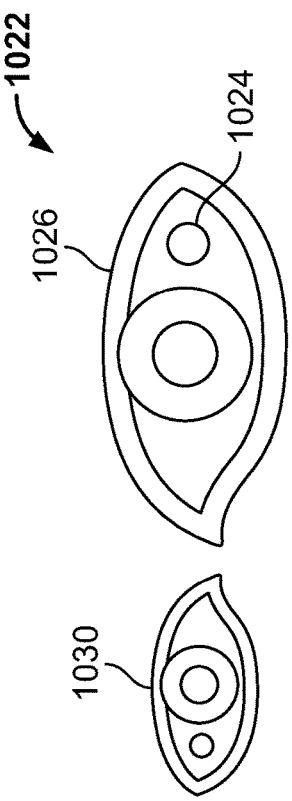
FIG. 57 shows another embodiment of the example icons from the display portion of the pre-acquisition interface shown in FIG. 46.
Figure 56:
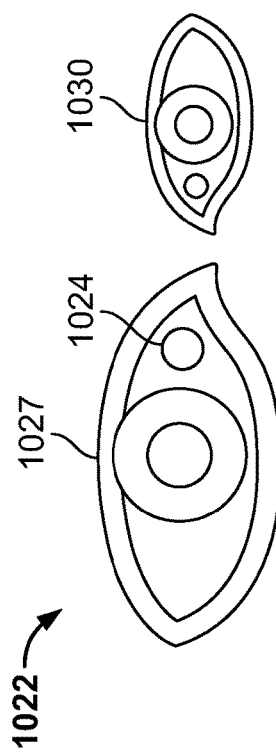
FIG. 56 shows another embodiment of the example icons from the display portion of the pre-acquisition interface shown in FIG. 46.
Figure 58:
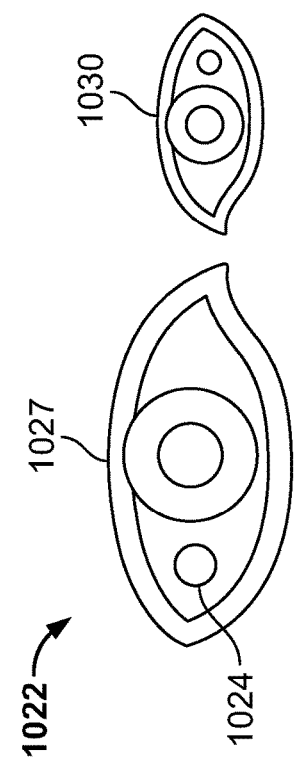
FIG. 58 shows another embodiment of the example icons from the display portion of the pre-acquisition interface shown in FIG. 46.

Similarly, for FIGS. 55-56, the dot 1024 is centered on the optic disc (i.e., optic disc-centered). This again helps the user understand how focus will be performed. For FIGS. 57-58, the dot 1024 is focused on a different area of the eye to provide a different prescriptive workflow. Other configurations are contemplated.

The user can use one or more of the different focuses in accordance with one or more prescriptive workflows to use the device 702 to capture images focused on different portions of the eye. As shown and described above, the images for the different prescriptive workflows can be accomplished in a manner as shown in FIGS. 46-48, and the exam summary interface 1100 of FIG. 49 indicates all of the images captured for the different prescriptive workflows.

In one example, the device 702 can be programmed (during setup of the device) to perform one, two, or more prescriptive workflows to capture images at different focal points. The user can configure the device 702 as desired. In another example, a remote device (e.g., server) can program the device 702 to perform one or more of the prescriptive workflows. For example, a caregiver can annotate a patient record requesting that both optic disc- and macula-centered images be taken for a patient. The server then programs the device 702 (e.g., through communication through a network to the device) to perform the necessary prescriptive workflows to accomplish the capture of the desired images.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A fundus imaging system, comprising:
   a handheld housing;
   a display supported by the handheld housing;
   a camera housed inside the handheld housing; and
   a computing device in communication with the display and the camera, the computing device including at least one processor and a memory storing instructions which, when executed by the at least one processor, cause the system to:
      capture a first image using the camera, the first image being captured at a first image point focus for a given eye;
      provide a control on the display;
      when the control is selected, capture a second image using the camera; and
      display an exam summary interface on the display, the exam summary interface providing a summary of images captured by the camera including an image quality score for each captured image, wherein the image quality score includes a graphical representation of the image quality score, and wherein the image quality score for the second image is indented from the image quality score for the first image.

2. The system of claim 1, wherein selection of the control enables the camera to capture the second image without requesting additional parameters.

3. The system of claim 1, wherein the exam summary interface includes a right eye summary pane and a left eye summary pane.

4. The system of claim 3, wherein the right and left eye summary panes each display a summary of images captured by the camera for each eye of a patient.

5. The system of claim 4, wherein the summary of images includes a left eye optic disc centered image, a left eye macula centered image, a right eye optic disc centered image, and a right eye macula centered image.

6. The system of claim 4, wherein the right and left eye summary panes display controls for capturing additional images at a given image point focus for each eye.

7. The system of claim 1, wherein the second image is captured at the first image point focus for the given eye when an image quality score of the first image is below a predetermined threshold.

8. The system of claim 1, wherein the second image is captured at a second image point focus for the given eye, the second image point focus being different from the first image point focus, and the first and second image point foci including optic disc centered and macula centered foci.

9. The system of claim 1, wherein the second image is captured for another eye of a patient, the second image being captured at the first image point focus, the first image point focus being an optic disc centered focus or a macula centered focus.

10. The system of claim 1, wherein the second image is captured for another eye of a patient, the second image being captured at a second image point focus, and the first and second image point foci include an optic disc centered focus and a macula centered focus.

11. A non-transitory computer readable storage media, including computer readable instructions which when read and executed by a computing device, cause the computing device to:
   capture a first image at a first image point focus for a given eye;
   provide a control on a display;
   when the control is selected, capture a second image; and
   display an exam summary interface on the display, the exam summary interface providing a summary of captured images including an image quality score for each captured image, wherein the image quality score includes a graphical representation of the image quality score, wherein the graphical representation has a first state when the image quality score is below a threshold, and the graphical representation has a second state when the image quality score is above the threshold, and wherein the image quality score for the second image is indented from the image quality score for the first image.

12. The non-transitory computer readable storage media of claim 11, wherein the summary of captured images includes a left eye optic disc centered image, a left eye macula centered image, a right eye optic disc centered image, and a right eye macula centered image.

13. The non-transitory computer readable storage media of claim 11, wherein the second image is captured without requesting additional parameters.

14. The non-transitory computer readable storage media of claim 11, wherein the second image is captured without deleting the first image.

15. The non-transitory computer readable storage media of claim 11, wherein the exam summary interface includes a right eye summary pane and a left eye summary pane, the right and left eye summary panes each display a summary of captured images for each eye of a patient including a left eye optic disc centered image, a left eye macula centered image, a right eye optic disc centered image, and a right eye macula centered image, and the right and left eye summary panes each display controls for capturing additional images at a given image point focus for each eye.

16. A method for imaging a fundus of a patient, the method comprising:
   capturing a first image at a first image point focus for a given eye;
   providing a control on a display;
   when the control is selected, capturing a second image; and displaying an exam summary interface on the display, the exam summary interface providing a summary of captured images including an image point focus and an image quality score for each captured image, wherein the image quality score includes a graphical representation of the image quality score, wherein the graphical representation has a first state when the image quality score is below a threshold, and the graphical representation has a second state when the image quality score is above the threshold, and wherein the image quality score for the second image is indented from the image quality score for the first image.

17. The method of claim 16, wherein the exam summary interface includes a right eye summary pane and a left eye summary pane, the right and left eye summary panes each display a summary of captured images for each eye of a patient including a left eye optic disc centered image, a left eye macula centered image, a right eye optic disc centered image, and a right eye macula centered image, and the right and left eye summary panes each displaying controls for capturing additional images at a given image point focus for each eye.

18. The method of claim 16, wherein the second image is captured at the first image point focus for the given eye when an image quality score of the first image is below a predetermined threshold.

19. The method of claim 16, wherein the second image is captured at a second image point focus for the given eye, the second image point focus being different from the first image point focus, and the first and second image point foci including optic disc centered and macula centered foci.

20. The method of claim 16, wherein the second image is captured for another eye of a patient, the second image being captured at the first image point focus, the first image point focus being an optic disc centered focus or a macula centered focus.

* * * * *